US010851377B2

(12) United States Patent
Fitzgerald

(10) Patent No.: US 10,851,377 B2
(45) Date of Patent: Dec. 1, 2020

(54) METHODS AND COMPOSITIONS FOR TREATING A PROPROTEIN CONVERTASE SUBTILISIN KEXIN (PCSK9) GENE-ASSOCIATED DISORDER

(71) Applicant: Alnylam Pharmaceuticals, Inc., Cambridge, MA (US)

(72) Inventor: Kevin Fitzgerald, Brookline, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/744,689

(22) Filed: Jan. 16, 2020

(65) Prior Publication Data

US 2020/0140871 A1 May 7, 2020

Related U.S. Application Data

(63) Continuation of application No. 15/895,023, filed on Feb. 13, 2018, now abandoned, which is a continuation of application No. PCT/US2016/048666, filed on Aug. 25, 2016.

(60) Provisional application No. 62/209,526, filed on Aug. 25, 2015.

(51) Int. Cl.
| | | |
|---|---|---|
| C12N 15/11 | (2006.01) | |
| C12N 15/113 | (2010.01) | |
| A61K 31/7115 | (2006.01) | |
| A61K 31/713 | (2006.01) | |
| A61P 3/06 | (2006.01) | |
| A61K 9/00 | (2006.01) | |
| A61K 39/395 | (2006.01) | |
| A61K 45/06 | (2006.01) | |

(52) U.S. Cl.
CPC ........ *C12N 15/1137* (2013.01); *A61K 9/0019* (2013.01); *A61K 31/713* (2013.01); *A61K 31/7115* (2013.01); *A61K 39/3955* (2013.01); *A61K 45/06* (2013.01); *A61P 3/06* (2018.01); *C12N 2310/14* (2013.01); *C12N 2310/315* (2013.01); *C12N 2310/321* (2013.01)

(58) Field of Classification Search
None
See application file for complete search history.

(56) References Cited

U.S. PATENT DOCUMENTS

| | | | |
|---|---|---|---|
| 6,054,299 A | 4/2000 | Conrad | |
| 6,271,359 B1 | 8/2001 | Norris et al. | |
| 7,150,970 B2 | 12/2006 | Trask et al. | |
| 7,427,605 B2 | 9/2008 | Davis et al. | |
| 7,491,805 B2 | 2/2009 | Vargeese et al. | |
| 7,507,811 B2 | 3/2009 | Khvorova et al. | |
| 7,511,132 B2 | 3/2009 | Khvorova et al. | |
| 7,514,550 B2 | 4/2009 | Khvorova et al. | |
| 7,521,191 B2 | 4/2009 | Khvorova et al. | |
| 7,541,453 B2 | 6/2009 | Khvorova et al. | |
| 7,550,572 B2 | 6/2009 | Khvorova et al. | |
| 7,569,684 B2 | 8/2009 | Khvorova et al. | |
| 7,576,196 B2 | 8/2009 | Khvorova et al. | |
| 7,576,197 B2 | 8/2009 | Khvorova et al. | |
| 7,579,457 B2 | 8/2009 | Khvorova et al. | |
| 7,579,458 B2 | 8/2009 | Khvorova et al. | |
| 7,582,746 B2 | 9/2009 | Khvorova et al. | |
| 7,582,747 B2 | 9/2009 | Khvorova et al. | |
| 7,589,191 B2 | 9/2009 | Khvorova et al. | |
| 7,592,442 B2 | 9/2009 | Khvorova et al. | |
| 7,592,443 B2 | 9/2009 | Khvorova et al. | |
| 7,592,444 B2 | 9/2009 | Khvorova et al. | |
| 7,595,388 B2 | 9/2009 | Khvorova et al. | |
| 7,595,389 B2 | 9/2009 | Khvorova et al. | |
| 7,598,369 B2 | 10/2009 | Khvorova et al. | |
| 7,598,370 B2 | 10/2009 | Khvorova et al. | |
| 7,605,251 B2 | 10/2009 | Tan et al. | |
| 7,605,252 B2 | 10/2009 | Khvorova et al. | |
| 7,608,706 B2 | 10/2009 | Khvorova et al. | |
| 7,608,707 B2 | 10/2009 | Khvorova et al. | |
| 7,612,196 B2 | 11/2009 | Khvorova et al. | |
| 7,615,541 B2 | 11/2009 | Khvorova et al. | |
| 7,619,081 B2 | 11/2009 | Khvorova et al. | |
| 7,632,938 B2 | 12/2009 | Khvorova et al. | |
| 7,632,939 B2 | 12/2009 | Khvorova et al. | |
| 7,635,770 B2 | 12/2009 | Khvorova et al. | |
| 7,635,771 B2 | 12/2009 | Khvorova et al. | |
| 7,638,621 B2 | 12/2009 | Khvorova et al. | |
| 7,638,622 B2 | 12/2009 | Khvorova et al. | |

(Continued)

FOREIGN PATENT DOCUMENTS

| | | |
|---|---|---|
| WO | WO-2004/045543 A2 | 6/2004 |
| WO | WO-2005/003350 A2 | 1/2005 |

(Continued)

OTHER PUBLICATIONS

Winter et al, Vascular Risk Factors, Cardiovascular Disease, and Restless Legs Syndrome in Women, The American Journal of Medicine, 2013, vol. 126, 3: 220-227 (Year: 2013).*
U.S. Appl. No. 14/650,128, filed Jun. 5, 2015 U.S. Pat. No. 10,125,369, Nov. 13, 2018, US 20160017335, Granted.
U.S. Appl. No. 16/155,965, filed Oct. 10, 2018, Pending.
U.S. Appl. No. 15/895,023, filed Feb. 13, 2018, US 2018/0187198, Allowed.
Positive Results from Alnylam's ALN-PCS Phase I Trial on Severe Hypercholesterolemia (Apr. 21, 2012) Retrieved from <https://www.news-medical.net/news/20120421/Positive-results-from-Alnylame28099s-ALN-PCS-Phase-I-trial-on-severe-hypercholesterolemia.aspx>.
International Search Report and Written Opinion from PCT/US2013/073349, dated Mar. 6, 2014.

(Continued)

*Primary Examiner* — Ekaterina Poliakova-Georgantas
(74) *Attorney, Agent, or Firm* — McCarter & English, LLP; Maria Laccotripe Zacharakis; Deborah L. Nagle

(57) ABSTRACT

The invention relates to methods of inhibiting the expression of a PCSK9 gene in a subject, as well as therapeutic and prophylactic methods for treating subjects having a lipid disorder, such as a hyperlipidemia using RNAi agents, e.g., double-stranded RNAi agents, targeting the PCSK9 gene.

30 Claims, 4 Drawing Sheets

Specification includes a Sequence Listing.

(56) References Cited

U.S. PATENT DOCUMENTS

| | | |
|---|---|---|
| 7,642,349 B2 | 1/2010 | Khvorova et al. |
| 7,645,869 B2 | 1/2010 | Khvorova et al. |
| 7,645,870 B2 | 1/2010 | Khvorova et al. |
| 7,655,788 B2 | 2/2010 | Khvorova et al. |
| 7,655,789 B2 | 2/2010 | Khvorova et al. |
| 7,662,950 B2 | 2/2010 | Khvorova et al. |
| 7,666,853 B2 | 2/2010 | Khvorova et al. |
| 7,674,896 B2 | 3/2010 | Khvorova et al. |
| 7,678,896 B2 | 3/2010 | Khvorova et al. |
| 7,691,997 B2 | 4/2010 | Khvorova et al. |
| 7,691,998 B2 | 4/2010 | Khvorova et al. |
| 7,696,344 B2 | 4/2010 | Khvorova et al. |
| 7,709,629 B2 | 5/2010 | Khvorova et al. |
| 7,718,629 B2 | 5/2010 | Bumcrot et al. |
| 7,737,267 B2 | 6/2010 | Khvorova et al. |
| 7,741,470 B2 | 6/2010 | Khvorova et al. |
| 7,745,610 B2 | 6/2010 | Khvorova et al. |
| 7,745,611 B2 | 6/2010 | Khvorova et al. |
| 7,745,612 B2 | 6/2010 | Khvorova et al. |
| 7,781,575 B2 | 8/2010 | Khvorova et al. |
| 7,795,420 B2 | 9/2010 | Khvorova et al. |
| 7,795,421 B2 | 9/2010 | Khvorova et al. |
| 7,803,933 B2 | 9/2010 | Khvorova et al. |
| 7,807,819 B2 | 10/2010 | Khvorova et al. |
| 7,807,820 B2 | 10/2010 | Khvorova et al. |
| 7,816,512 B2 | 10/2010 | Khvorova et al. |
| 7,820,809 B2 | 10/2010 | Khvorova et al. |
| 7,829,696 B2 | 11/2010 | Khvorova et al. |
| 7,833,989 B2 | 11/2010 | Khvorova et al. |
| 7,833,992 B2 | 11/2010 | Vargeese et al. |
| 7,834,170 B2 | 11/2010 | Khvorova et al. |
| 7,855,186 B2 | 12/2010 | Khvorova et al. |
| 7,893,247 B2 | 2/2011 | Khvorova et al. |
| 7,897,754 B2 | 3/2011 | Khvorova et al. |
| 7,935,813 B2 | 5/2011 | Khvorova et al. |
| 7,951,935 B2 | 5/2011 | Khvorova et al. |
| 7,977,471 B2 | 7/2011 | Khvorova et al. |
| 7,985,854 B2 | 7/2011 | Khvorova et al. |
| 7,999,097 B2 | 8/2011 | Khvorova et al. |
| 8,008,474 B2 | 8/2011 | Khvorova et al. |
| 8,013,145 B2 | 9/2011 | Khvorova et al. |
| 8,022,198 B2 | 9/2011 | Khvorova et al. |
| 8,022,199 B2 | 9/2011 | Khvorova et al. |
| 8,030,474 B2 | 10/2011 | Khvorova et al. |
| 8,030,476 B2 | 10/2011 | Khvorova et al. |
| 8,039,610 B2 | 10/2011 | Khvorova et al. |
| 8,067,576 B2 | 11/2011 | Khvorova et al. |
| 8,071,754 B2 | 12/2011 | Khvorova et al. |
| 8,084,437 B2 | 12/2011 | Freier et al. |
| 8,090,542 B2 | 1/2012 | Khvorova et al. |
| 8,093,222 B2 | 1/2012 | Freier et al. |
| 8,093,370 B2 | 1/2012 | Khvorova et al. |
| 8,106,022 B2 | 1/2012 | Manoharan et al. |
| 8,138,329 B2 | 3/2012 | Khvorova et al. |
| 8,198,427 B1 | 6/2012 | Khvorova et al. |
| 8,202,979 B2 | 6/2012 | McSwiggen et al. |
| 8,217,162 B2 | 7/2012 | Khvorova et al. |
| 8,222,222 B2 | 7/2012 | Tan et al. |
| 8,222,395 B2 | 7/2012 | Khvorova et al. |
| 8,222,396 B2 | 7/2012 | Khvorova et al. |
| 8,232,385 B2 | 7/2012 | Khvorova et al. |
| 8,232,386 B2 | 7/2012 | Khvorova et al. |
| 8,236,942 B2 | 8/2012 | Khvorova et al. |
| 8,247,169 B2 | 8/2012 | Khvorova et al. |
| 8,268,985 B2 | 9/2012 | Khvorova et al. |
| 8,273,866 B2 | 9/2012 | McSwiggen et al. |
| 8,273,869 B2 | 9/2012 | Fitzgerald et al. |
| 8,293,887 B2 | 10/2012 | Khvorova et al. |
| 8,304,528 B2 | 11/2012 | Khvorova et al. |
| 8,314,229 B2 | 11/2012 | Khvorova et al. |
| 8,399,654 B2 | 3/2013 | Khvorova et al. |
| 8,426,579 B2 | 4/2013 | Khvorova et al. |
| 8,445,667 B2 | 5/2013 | Khvorova et al. |
| 8,445,668 B2 | 5/2013 | Khvorova et al. |
| 8,450,467 B2 | 5/2013 | Manoharan et al. |
| 8,461,326 B2 | 6/2013 | Khvorova et al. |
| 8,575,329 B2 | 11/2013 | Khvorova et al. |
| 8,598,139 B2 | 12/2013 | Fitzgerald et al. |
| 8,633,306 B2 | 1/2014 | Khvorova et al. |
| 8,658,784 B2 | 2/2014 | Khvorova et al. |
| 8,658,785 B1 | 2/2014 | Khvorova et al. |
| 8,664,190 B2 | 3/2014 | Freier et al. |
| 8,759,284 B2 | 6/2014 | Imran |
| 8,809,292 B2 | 8/2014 | Tan et al. |
| 8,828,956 B2 | 9/2014 | Manoharan et al. |
| 8,883,998 B2 | 11/2014 | Khvorava et al. |
| 8,907,077 B2 | 12/2014 | Khvorova et al. |
| 8,937,172 B2 | 1/2015 | Khvorova et al. |
| 9,228,186 B2 | 1/2016 | Khvorova et al. |
| 9,260,718 B2 | 2/2016 | Tan et al. |
| 9,370,582 B2 | 6/2016 | Manoharan et al. |
| 9,399,775 B2 | 7/2016 | Rajeev et al. |
| 9,513,606 B1 | 12/2016 | Larsen et al. |
| 9,796,974 B2 | 10/2017 | Rajeev et al. |
| 10,125,369 B2 | 11/2018 | Borodovsky et al. |
| 2004/0001811 A1 | 1/2004 | Kreutzer et al. |
| 2004/0045543 A1 | 3/2004 | Perryman |
| 2004/0248177 A1 | 12/2004 | Abi Fadel et al. |
| 2005/0003350 A1 | 1/2005 | Johnston-Dow et al. |
| 2005/0007854 A1 | 1/2005 | Imondi |
| 2005/0007855 A1 | 1/2005 | Lee et al. |
| 2005/0007859 A1 | 1/2005 | Chung et al. |
| 2005/0014811 A1 | 1/2005 | Clerc et al. |
| 2005/0019453 A1 | 1/2005 | Witkowski |
| 2005/0028649 A1 | 2/2005 | Settanni |
| 2005/0028650 A1 | 2/2005 | Tassano et al. |
| 2005/0032733 A1 | 2/2005 | McSwiggen et al. |
| 2005/0035759 A1 | 2/2005 | Herbert et al. |
| 2005/0040379 A1 | 2/2005 | Hung |
| 2005/0044981 A1 | 3/2005 | Huang |
| 2005/0045032 A1 | 3/2005 | Dasgupta et al. |
| 2005/0045034 A1 | 3/2005 | Paglieri et al. |
| 2005/0045035 A1 | 3/2005 | Siegfried et al. |
| 2005/0045036 A1 | 3/2005 | Vetter et al. |
| 2005/0045037 A1 | 3/2005 | Parisi et al. |
| 2005/0045038 A1 | 3/2005 | Huang |
| 2005/0045039 A1 | 3/2005 | Shellhammer et al. |
| 2005/0045040 A1 | 3/2005 | McCombs |
| 2005/0045041 A1 | 3/2005 | Hechinger et al. |
| 2005/0070497 A1 | 3/2005 | McSwiggen et al. |
| 2005/0079610 A1 | 4/2005 | Polisky et al. |
| 2005/0105995 A1 | 5/2005 | Freet et al. |
| 2005/0119211 A1 | 6/2005 | Chowrira et al. |
| 2005/0119212 A1 | 6/2005 | Haeberli et al. |
| 2005/0124566 A1 | 6/2005 | Robin et al. |
| 2005/0124567 A1 | 6/2005 | McSwiggen et al. |
| 2005/0124568 A1 | 6/2005 | Usman et al. |
| 2005/0124569 A1 | 6/2005 | Guerciolini et al. |
| 2005/0130181 A1 | 6/2005 | McSwiggen |
| 2005/0136436 A1 | 6/2005 | McSwiggen et al. |
| 2005/0137153 A1 | 6/2005 | McSwiggen et al. |
| 2005/0137155 A1 | 6/2005 | McSwiggen et al. |
| 2005/0143333 A1 | 6/2005 | Richards et al. |
| 2005/0153914 A1 | 7/2005 | McSwiggen et al. |
| 2005/0153916 A1 | 7/2005 | McSwiggen et al. |
| 2005/0158735 A1 | 7/2005 | McSwiggen et al. |
| 2005/0159376 A1 | 7/2005 | McSwiggen et al. |
| 2005/0159378 A1 | 7/2005 | McSwiggen et al. |
| 2005/0159379 A1 | 7/2005 | McSwiggen et al. |
| 2005/0159380 A1 | 7/2005 | Guerciolini et al. |
| 2005/0159381 A1 | 7/2005 | McSwiggen et al. |
| 2005/0159382 A1 | 7/2005 | McSwiggen et al. |
| 2005/0164224 A1 | 7/2005 | McSwiggen et al. |
| 2005/0164966 A1 | 7/2005 | McSwiggen et al. |
| 2005/0164967 A1 | 7/2005 | McSwiggen et al. |
| 2005/0164968 A1 | 7/2005 | McSwiggen et al. |
| 2005/0170371 A1 | 8/2005 | McSwiggen et al. |
| 2005/0171040 A1 | 8/2005 | Polisky et al. |
| 2005/0176024 A1 | 8/2005 | McSwiggen et al. |
| 2005/0176025 A1 | 8/2005 | McSwiggen et al. |
| 2005/0176663 A1 | 8/2005 | McSwiggen et al. |
| 2005/0176664 A1 | 8/2005 | Richards et al. |
| 2005/0176665 A1 | 8/2005 | McSwiggen |
| 2005/0176666 A1 | 8/2005 | Richards et al. |

(56) References Cited

U.S. PATENT DOCUMENTS

| | | |
|---|---|---|
| 2005/0182006 A1 | 8/2005 | McSwiggen et al. |
| 2005/0182007 A1 | 8/2005 | McSwiggen et al. |
| 2005/0182008 A1 | 8/2005 | McSwiggen et al. |
| 2005/0182009 A1 | 8/2005 | McSwiggen et al. |
| 2005/0187174 A1 | 8/2005 | Richards et al. |
| 2005/0191618 A1 | 9/2005 | McSwiggen et al. |
| 2005/0196765 A1 | 9/2005 | McSwiggen et al. |
| 2005/0196767 A1 | 9/2005 | McSwiggen et al. |
| 2005/0196781 A1 | 9/2005 | Robin et al. |
| 2005/0203040 A1 | 9/2005 | Richards et al. |
| 2005/0209179 A1 | 9/2005 | McSwiggen et al. |
| 2005/0209180 A1 | 9/2005 | Jadhav et al. |
| 2005/0222064 A1 | 10/2005 | Vargeese et al. |
| 2005/0222066 A1 | 10/2005 | Richards et al. |
| 2005/0227935 A1 | 10/2005 | McSwiggen et al. |
| 2005/0227936 A1 | 10/2005 | McSwiggen et al. |
| 2005/0233344 A1 | 10/2005 | McSwiggen et al. |
| 2005/0233997 A1 | 10/2005 | Richards et al. |
| 2005/0233998 A1 | 10/2005 | Jadhav et al. |
| 2005/0239731 A1 | 10/2005 | McSwiggen et al. |
| 2005/0255487 A1 | 11/2005 | Khvorova et al. |
| 2005/0256068 A1 | 11/2005 | McSwiggen et al. |
| 2005/0260620 A1 | 11/2005 | Christiano et al. |
| 2005/0261219 A1 | 11/2005 | Richards et al. |
| 2005/0267058 A1 | 12/2005 | McSwiggen et al. |
| 2005/0277133 A1 | 12/2005 | McSwiggen |
| 2005/0277608 A1 | 12/2005 | Guerciolini et al. |
| 2005/0282188 A1 | 12/2005 | Haeberli et al. |
| 2005/0287128 A1 | 12/2005 | Guerciolini et al. |
| 2005/0288242 A1 | 12/2005 | McSwiggen |
| 2006/0019913 A1 | 1/2006 | McSwiggen et al. |
| 2006/0019917 A1 | 1/2006 | Guerciolini et al. |
| 2006/0025361 A1 | 2/2006 | McSwiggen et al. |
| 2006/0142225 A1 | 6/2006 | McSwiggen |
| 2006/0142226 A1 | 6/2006 | Polisky et al. |
| 2006/0148743 A1 | 7/2006 | Jadhav et al. |
| 2006/0211642 A1 | 9/2006 | McSwiggen et al. |
| 2006/0216747 A1 | 9/2006 | McSwiggen et al. |
| 2006/0217331 A1 | 9/2006 | Vargeese et al. |
| 2006/0217332 A1 | 9/2006 | Vargeese et al. |
| 2006/0241075 A1 | 10/2006 | McSwiggen |
| 2006/0247194 A1 | 11/2006 | McSwiggen et al. |
| 2006/0270623 A1 | 11/2006 | McSwiggen |
| 2006/0276422 A1 | 12/2006 | Usman et al. |
| 2006/0287267 A1 | 12/2006 | Vaish et al. |
| 2007/0010561 A1 | 1/2007 | Brown et al. |
| 2007/0032441 A1 | 2/2007 | McSwiggen et al. |
| 2007/0039072 A1 | 2/2007 | Khvorova et al. |
| 2007/0042983 A1 | 2/2007 | Haeberli et al. |
| 2007/0042986 A1 | 2/2007 | Trask et al. |
| 2007/0049543 A1 | 3/2007 | McSwiggen et al. |
| 2007/0088155 A1 | 4/2007 | Khvorova et al. |
| 2007/0093437 A1 | 4/2007 | Chowrira et al. |
| 2007/0093653 A1 | 4/2007 | Khvorova et al. |
| 2007/0128641 A1 | 6/2007 | Khvorova et al. |
| 2007/0160980 A1 | 7/2007 | Haeberli et al. |
| 2007/0161596 A1 | 7/2007 | McSwiggen et al. |
| 2007/0173473 A1 | 7/2007 | McSwiggen et al. |
| 2007/0179104 A1 | 8/2007 | McSwiggen |
| 2007/0179286 A1 | 8/2007 | Khvorova et al. |
| 2007/0185043 A1 | 8/2007 | McSwiggen et al. |
| 2007/0185049 A1 | 8/2007 | Jadhav et al. |
| 2007/0185317 A1 | 8/2007 | Khvorova et al. |
| 2007/0213520 A1 | 9/2007 | Khvorova et al. |
| 2007/0213521 A1 | 9/2007 | Khvorova et al. |
| 2007/0219362 A1 | 9/2007 | Khvorova et al. |
| 2007/0232797 A1 | 10/2007 | Khvorova et al. |
| 2007/0238868 A1 | 10/2007 | Khvorova et al. |
| 2007/0244312 A1 | 10/2007 | Khvorova et al. |
| 2007/0249819 A1 | 10/2007 | Khvorova et al. |
| 2007/0255046 A1 | 11/2007 | Khvorova et al. |
| 2007/0255047 A1 | 11/2007 | Khvorova et al. |
| 2007/0255048 A1 | 11/2007 | Khvorova et al. |
| 2007/0255050 A1 | 11/2007 | Khvorova et al. |
| 2007/0255051 A1 | 11/2007 | Khvorova et al. |
| 2007/0255052 A1 | 11/2007 | Khvorova et al. |
| 2007/0260047 A1 | 11/2007 | Khvorova et al. |
| 2007/0260048 A1 | 11/2007 | Khvorova et al. |
| 2007/0260049 A1 | 11/2007 | Khvorova et al. |
| 2007/0260050 A1 | 11/2007 | Khvorova et al. |
| 2007/0260051 A1 | 11/2007 | Khvorova et al. |
| 2007/0260052 A1 | 11/2007 | Khvorova et al. |
| 2007/0265437 A1 | 11/2007 | Khvorova et al. |
| 2007/0270579 A1 | 11/2007 | Jadhav et al. |
| 2007/0276135 A1 | 11/2007 | Khvorova et al. |
| 2007/0287833 A1 | 12/2007 | Khvorova et al. |
| 2007/0293664 A1 | 12/2007 | Khvorova et al. |
| 2007/0299253 A1 | 12/2007 | Khvorova et al. |
| 2008/0015114 A1 | 1/2008 | Khvorova et al. |
| 2008/0027215 A1 | 1/2008 | Khvorova et al. |
| 2008/0027216 A1 | 1/2008 | Khvorova et al. |
| 2008/0033156 A1 | 2/2008 | Vargeese et al. |
| 2008/0039617 A1 | 2/2008 | Khvorova et al. |
| 2008/0045703 A1 | 2/2008 | Khvorova et al. |
| 2008/0066776 A1 | 3/2008 | Chodorow et al. |
| 2008/0071073 A1 | 3/2008 | Khvorova et al. |
| 2008/0076908 A1 | 3/2008 | Khvorova et al. |
| 2008/0081904 A1 | 4/2008 | Khvorova et al. |
| 2008/0085997 A1 | 4/2008 | Khvorova et al. |
| 2008/0086002 A1 | 4/2008 | Khvorova et al. |
| 2008/0091001 A1 | 4/2008 | Khvorova et al. |
| 2008/0091002 A1 | 4/2008 | Khvorova et al. |
| 2008/0091003 A1 | 4/2008 | Khvorova et al. |
| 2008/0091004 A1 | 4/2008 | Khvorova et al. |
| 2008/0097089 A1 | 4/2008 | Khvorova et al. |
| 2008/0097091 A1 | 4/2008 | Khvorova et al. |
| 2008/0097092 A1 | 4/2008 | Khvorova et al. |
| 2008/0108802 A1 | 5/2008 | Khvorova et al. |
| 2008/0108803 A1 | 5/2008 | Khvorova et al. |
| 2008/0113371 A1 | 5/2008 | Khvorova et al. |
| 2008/0113372 A1 | 5/2008 | Khvorova et al. |
| 2008/0113374 A1 | 5/2008 | Khvorova et al. |
| 2008/0114162 A1 | 5/2008 | Khvorova et al. |
| 2008/0161256 A1 | 7/2008 | Morrisey et al. |
| 2008/0161547 A1 | 7/2008 | Khvorova et al. |
| 2008/0188430 A1 | 8/2008 | Usman et al. |
| 2008/0188648 A1 | 8/2008 | Khvorova et al. |
| 2008/0207884 A1 | 8/2008 | Khvorova et al. |
| 2008/0221316 A1 | 9/2008 | Khvorova et al. |
| 2008/0221317 A1 | 9/2008 | Khvorova et al. |
| 2008/0249040 A1 | 10/2008 | McSwiggen et al. |
| 2008/0249294 A1 | 10/2008 | Haeberli et al. |
| 2008/0268457 A1 | 10/2008 | Khvorova et al. |
| 2008/0293595 A1 | 11/2008 | Khvorova et al. |
| 2008/0300395 A1 | 12/2008 | Khvorova et al. |
| 2008/0306015 A1 | 12/2008 | Khvorova et al. |
| 2009/0005547 A1 | 1/2009 | Khvorova et al. |
| 2009/0005548 A1 | 1/2009 | Khvorova et al. |
| 2009/0023907 A1 | 1/2009 | Khvorova et al. |
| 2009/0023908 A1 | 1/2009 | Khvorova et al. |
| 2009/0030190 A1 | 1/2009 | Khvorova et al. |
| 2009/0043084 A1 | 2/2009 | Khvorova et al. |
| 2009/0093431 A1 | 4/2009 | McSwiggen et al. |
| 2009/0093435 A1 | 4/2009 | McSwiggen et al. |
| 2009/0093436 A1 | 4/2009 | McSwiggen et al. |
| 2009/0093437 A1 | 4/2009 | McSwiggen et al. |
| 2009/0093438 A1 | 4/2009 | McSwiggen et al. |
| 2009/0093439 A1 | 4/2009 | McSwiggen et al. |
| 2009/0099115 A1 | 4/2009 | McSwiggen et al. |
| 2009/0099116 A1 | 4/2009 | McSwiggen et al. |
| 2009/0099117 A1 | 4/2009 | McSwiggen et al. |
| 2009/0099118 A1 | 4/2009 | McSwiggen et al. |
| 2009/0099119 A1 | 4/2009 | McSwiggen et al. |
| 2009/0099121 A1 | 4/2009 | McSwiggen et al. |
| 2009/0105178 A1 | 4/2009 | McSwiggen et al. |
| 2009/0137507 A1 | 5/2009 | McSwiggen et al. |
| 2009/0137508 A1 | 5/2009 | McSwiggen et al. |
| 2009/0137509 A1 | 5/2009 | McSwiggen et al. |
| 2009/0137510 A1 | 5/2009 | McSwiggen et al. |
| 2009/0137511 A1 | 5/2009 | McSwiggen et al. |
| 2009/0137512 A1 | 5/2009 | McSwiggen et al. |
| 2009/0137513 A1 | 5/2009 | McSwiggen et al. |
| 2009/0143324 A1 | 6/2009 | McSwiggen et al. |
| 2009/0143325 A1 | 6/2009 | McSwiggen et al. |

(56) References Cited

U.S. PATENT DOCUMENTS

| | | |
|---|---|---|
| 2009/0149408 A1 | 6/2009 | McSwiggen et al. |
| 2009/0156533 A1 | 6/2009 | McSwiggen et al. |
| 2009/0163701 A1 | 6/2009 | Khvorova et al. |
| 2009/0182134 A1 | 7/2009 | Khvorova et al. |
| 2009/0190918 A1 | 7/2009 | Chang |
| 2009/0192105 A1 | 7/2009 | McSwiggen et al. |
| 2009/0227780 A1 | 9/2009 | Khvorova et al. |
| 2009/0239931 A1 | 9/2009 | McSwiggen et al. |
| 2009/0253772 A1 | 10/2009 | McSwiggen et al. |
| 2009/0253773 A1 | 10/2009 | McSwiggen et al. |
| 2009/0253774 A1 | 10/2009 | McSwiggen et al. |
| 2009/0264504 A1 | 10/2009 | McSwiggen et al. |
| 2009/0275640 A1 | 11/2009 | Khvorova et al. |
| 2009/0281164 A1 | 11/2009 | McSwiggen et al. |
| 2009/0291497 A1 | 11/2009 | Khvorova et al. |
| 2009/0299045 A1 | 12/2009 | Richards et al. |
| 2009/0306182 A1 | 12/2009 | McSwiggen et al. |
| 2009/0306184 A1 | 12/2009 | McSwiggen et al. |
| 2010/0004141 A1 | 1/2010 | Khvorova et al. |
| 2010/0004142 A1 | 1/2010 | Khvorova et al. |
| 2010/0010066 A1 | 1/2010 | Fitzgerald et al. |
| 2010/0056395 A1 | 3/2010 | Khvorova et al. |
| 2010/0093835 A1 | 4/2010 | McSwiggen et al. |
| 2010/0099578 A1 | 4/2010 | Khvorova et al. |
| 2010/0099743 A1 | 4/2010 | McSwiggen et al. |
| 2010/0099744 A1 | 4/2010 | McSwiggen et al. |
| 2010/0113307 A1 | 5/2010 | Khvorova et al. |
| 2010/0113564 A1 | 5/2010 | McSwiggen et al. |
| 2010/0130592 A1 | 5/2010 | McSwiggen et al. |
| 2010/0144834 A1 | 6/2010 | Freier et al. |
| 2010/0144842 A1 | 6/2010 | McSwiggen et al. |
| 2010/0144851 A1 | 6/2010 | McSwiggen et al. |
| 2010/0145038 A1 | 6/2010 | McSwiggen et al. |
| 2010/0145039 A1 | 6/2010 | Khvorova et al. |
| 2010/0148013 A1 | 6/2010 | Bhotika et al. |
| 2010/0152064 A1 | 6/2010 | Khvorova et al. |
| 2010/0173976 A1 | 7/2010 | McSwiggen et al. |
| 2010/0184824 A1 | 7/2010 | McSwiggen et al. |
| 2010/0184825 A1 | 7/2010 | McSwiggen et al. |
| 2010/0227911 A1 | 9/2010 | McSwiggen et al. |
| 2010/0227912 A1 | 9/2010 | McSwiggen et al. |
| 2010/0228018 A1 | 9/2010 | McSwiggen et al. |
| 2010/0240730 A1 | 9/2010 | Beigelman et al. |
| 2010/0248990 A1 | 9/2010 | Khvorova et al. |
| 2010/0267587 A1 | 10/2010 | Khvorova et al. |
| 2010/0311812 A1 | 12/2010 | McSwiggen et al. |
| 2010/0317716 A1 | 12/2010 | McSwiggen et al. |
| 2010/0317717 A1 | 12/2010 | McSwiggen et al. |
| 2010/0331214 A1 | 12/2010 | Khvorova et al. |
| 2011/0015251 A1 | 1/2011 | McSwiggen et al. |
| 2011/0105363 A1 | 5/2011 | Khvorova et al. |
| 2011/0160281 A1 | 6/2011 | McSwiggen et al. |
| 2011/0313024 A1 | 12/2011 | Beigelman et al. |
| 2011/0319297 A1 | 12/2011 | Khvorova et al. |
| 2011/0319474 A1 | 12/2011 | Khvorova et al. |
| 2012/0004403 A1 | 1/2012 | Beigelman et al. |
| 2012/0015850 A1 | 1/2012 | Khvorova et al. |
| 2012/0058693 A1 | 3/2012 | Baldwin |
| 2012/0135892 A1 | 5/2012 | Khvorova et al. |
| 2012/0252873 A1 | 10/2012 | Khvorova et al. |
| 2012/0258888 A1 | 10/2012 | Khvorova et al. |
| 2012/0258889 A1 | 10/2012 | Khvorova et al. |
| 2012/0270751 A1 | 10/2012 | Khvorova et al. |
| 2012/0283311 A1 | 11/2012 | Khvorova et al. |
| 2013/0023446 A1 | 1/2013 | Khvorova et al. |
| 2013/0059760 A1 | 3/2013 | Khvorova et al. |
| 2013/0074974 A1 | 3/2013 | Murchie |
| 2013/0225447 A1 | 8/2013 | Khvorova et al. |
| 2013/0225667 A1 | 8/2013 | Khvorova et al. |
| 2013/0289094 A1 | 10/2013 | Hinkle et al. |
| 2014/0121263 A1 | 5/2014 | Fitzgerald et al. |
| 2014/0148362 A1 | 5/2014 | Khvorova et al. |
| 2014/0194492 A1 | 7/2014 | Freier et al. |
| 2014/0288158 A1 | 9/2014 | Rajeev et al. |
| 2015/0167005 A1 | 6/2015 | Freier et al. |
| 2016/0017335 A1 | 1/2016 | Borodovsky et al. |
| 2016/0152973 A1 | 6/2016 | Jadhav |
| 2016/0193242 A1 | 7/2016 | Khvorova et al. |
| 2016/0194646 A1 | 7/2016 | Khvorova et al. |
| 2016/0201058 A1 | 7/2016 | Khvorova et al. |
| 2016/0201065 A1 | 7/2016 | Khvorova et al. |
| 2016/0272975 A1 | 9/2016 | Jadhav |
| 2016/0348117 A1 | 12/2016 | Tan et al. |
| 2016/0354404 A1 | 12/2016 | Hinkle et al. |
| 2016/0355817 A1 | 12/2016 | Rajeev et al. |
| 2016/0369276 A1 | 12/2016 | Khvorova et al. |
| 2016/0369278 A1 | 12/2016 | Khvorova et al. |
| 2016/0369284 A1 | 12/2016 | Khvorova et al. |
| 2017/0000815 A1 | 1/2017 | Fitzgerald et al. |
| 2017/0035340 A1 | 2/2017 | Kim et al. |
| 2018/0008724 A1 | 1/2018 | Rajeev et al. |
| 2018/0104360 A1 | 4/2018 | Wijngaard et al. |

FOREIGN PATENT DOCUMENTS

| | | | |
|---|---|---|---|
| WO | WO-2005/007854 A2 | 1/2005 | |
| WO | WO-2005/007855 A2 | 1/2005 | |
| WO | WO-2005/007859 A2 | 1/2005 | |
| WO | WO-2005/014811 A2 | 2/2005 | |
| WO | WO-2005/028649 A1 | 3/2005 | |
| WO | WO-2005/028650 A2 | 3/2005 | |
| WO | WO-2005/035759 A2 | 4/2005 | |
| WO | WO-2005/040379 A2 | 5/2005 | |
| WO | WO-2005/044981 A2 | 5/2005 | |
| WO | WO-2005/045032 A2 | 5/2005 | |
| WO | WO-2005/045034 A2 | 5/2005 | |
| WO | WO-2005/045035 A2 | 5/2005 | |
| WO | WO-2005/045036 A2 | 5/2005 | |
| WO | WO-2005/045037 A2 | 5/2005 | |
| WO | WO-2005/045038 A2 | 5/2005 | |
| WO | WO-2005/045039 A2 | 5/2005 | |
| WO | WO-2005/045040 A2 | 5/2005 | |
| WO | WO-2005/045041 A2 | 5/2005 | |
| WO | WO-2005/105995 A2 | 11/2005 | |
| WO | WO-2008/011431 A2 | 1/2008 | |
| WO | WO-2010/148013 A2 | 12/2010 | |
| WO | WO-2012/058693 A2 | 5/2012 | |
| WO | WO-2014089313 A1 * | 6/2014 | ........... A61K 47/549 |
| WO | WO-2017/035340 A1 | 3/2017 | |

OTHER PUBLICATIONS

Kevin Fitzgerald: "A Subcutaneous, Potent and Durable RNAi Platform Targeting Metabolic Diseases, Genes PCSK9, ApoCI II and ANGPL T3", Mar. 1, 2014 (Mar. 1, 2014), XP055314837, Retrieved from the Internet: URL:http://www.alnylam.com/web/assets/ALNY-CardioMetabolicPrograms-ATVB-May2014.pdf.

RNAi Roundtable: ALN-PCSsc for the Treatment of Hypercholesterolemia, Jan. 1, 2014 (Jan. 1, 2014), XP055314824, Retrieved from the Internet: URL:http://www.alnylam.com/web/assets/RNALRoundtable_PCSsC_081414.pdf.

Anna Borodovsky: "Abstract 11936: Development of Monthly to Quarterly Subcutaneous Administration of RNAi Therapeutics Targeting the Metabolic Diseases Genes PCSK9, and ANGPTL3 | Circulation", Nov. 25, 2014 (Nov. 25, 2014), XP055314834, Retrieved from the Internet: URL:http://circ.ahajournals.org/contentl130/Suppl_2/A11936 [retrieved on Oct. 28, 2016].

Kevin Fitzgerald et al: "Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial" <https://worldwide.espacenet.com/nplReferenceDetails/biblio?FT=E&DB=&locale=en_EP&CC=XP&NR=055314131&KC=>, Oct. 3, 2013 (Oct. 3, 2013), XP055314131, Retrieved from the Internet: URL:http://ac.els-cdn.com/S0140673613619145/1-s2.0-S0140673613619145-main.pdf_tid=934e5128-9b71-11 e6-bOc6-00000aacb35d&acdnat=1477482458_13f4512706bdde225e2895b7dd2029d6 [retrieved on Oct. 26, 2016].

Kevin Fitzgerald et al: "A Subcutaneously Administered Investigational RNAi Therapeutic (ALN-PCSsc), Targeting PCSK9 for the

(56) References Cited

OTHER PUBLICATIONS

Treatment of Hypercholesterolemia: Initial Phase 1: Study Results", Aug. 30, 2015 (Aug. 30, 2015), XP055314809, Retrieved from the Internet: URL:http://www.alnylam.com/web/assets/ALN-PCSsc-Phase-1_Presentation_0830201. [retrieved on Oct. 28, 2016] ; -& Anonymous: "Positive Initial Clinical Data from Phase 1 1 with ALN-PCSsc—Alnylam", Aug. 30, 2015 (Aug. 30, 2015), XP55314896, Retrieved from the Internet: URL:http://www.alnylam.com/capeliaipresentations/positive-initial-phase-1-data-aln-pcsesc20151 [retrieved on Oct. 28, 2016].

Kevin Fitzgerald et al: "ALN-PCSsc, an RNAi Investigational Agent That Inhibits PCS Synthesis With the Potential for Effective Bi-Annual Dosing: Interim Results", Nov. 11, 2015 (Nov. 11, 2015), XP055314803, Retrieved from the Internet: URL:http://www.alnylam.com/web/assets/AHA_PCS-Ph-1_111115.pdf [retrieved on Oct. 28, 2016] ; -& Anonymous: "New Clinical Data from Phase 1 Trial with} PCSsc Confirms Potential for Bi-Annual Dosing—Alnylam", Nov. 11, 2015 (Nov. 11, 2015), XP55314805, Retrieved from the Internet: U R L :http://www.alnylam.com/capellalpresentations/data-from-phase-1-trial-with-al n-pc~confirms-potential-for-bi-annual-dosingl [retrieved on Oct. 28, 2016].

International Search Report and Written Opinion from PCT/US2016/048666 dated Nov. 16, 2016.

Extended European Search Report from EP 17195917.4 dated Mar. 15, 2018.

Graham et al., "Antisense inhibition of proprotein convertase subtilism/kexin type 9 reduces serum LDL in hyperlipidemic mice." Journal of Lipid Research, 2007 vol. 48, pp. 763-767.

GenBank Accession No. NM_174936. Homo sapiens proportein convertase subtilism/kexin type 9 (PCSK9), mRNA. Sep. 2007, see nucleotide sequence.

Basak, "Inhibitors of proprotein convertases", Journal of Molecular Medicine, 2005 vol. 83, pp. 844, 855.

Elbashir et al., "Functional anatomy of siRNAs for mediating efficient RNAi in *Drosophila melanogaster* embryo lysate", The Embo Journal, 2001 vol. 20, pp. 6877-6888.

Lu et al., "Delivering siRNA in vivo for functional genomics and novel therapeutics", in RNA Interference Technology (Cambridge, Appasani, ed.) pp. 303-317 (2005).

Samarsky et al., "RNAi in drug development: Practical considerations" in RNA Interference Technology (Cambridge, Appasani, ed.) pp. 384-395 (2005).

Downward, "Science, medicine, and the future", RNA interference. BMJ, 2004 vol. 328, pp. 1245-1248.

Benjannet et al. "NARC-1/PCSK9 and its natural mutants: zymogen cleavage and effects on the low density lipoprotein (LDL) receptor and LDL cholesterol", Journal of Biological Chemistry, American Society of Biochemical Biologists, Birmingham, US, vol. 279, No. 47, Nov. 19, 2004 (Nov. 19, 2004), pp. 48865-48875, XP002480952, ISSN: 0021-9258 [retrieved Sep. 9, 2004].

Harborth et al. "Sequence, chemical, and structural variation of small interfering RNAs and short hairpin RNAs and the effect on mammalian gene silencing", Antisense & Nucleic Acid Drug Development, Mary Ann Liebert, Inc., New York, US, vol. 13, No. 2, Apr. 1, 2003 (Apr. 1, 2003), pp. 83-105, XP002284355, ISSN: 1087-2906.

Reynolds et al., "Rational siRNA design for RNA interference," Nature Biotechnology, vol. 22, pp. 326-330, 2004.

\* cited by examiner

METHODS AND COMPOSITIONS FOR TREATING A PROPROTEIN CONVERTASE SUBTILISIN KEXIN (PCSK9) GENE-ASSOCIATED DISORDER

RELATED APPLICATIONS

This application is a continuation of U.S. patent application Ser. No. 15/895,023, filed on Feb. 13, 2018, which is a 35 § U.S.C. 111(a) continuation application which claims the benefit of priority to PCT/US2016/048666, filed on Aug. 25, 2016, which claims the benefit of priority to U.S. Provisional Patent Application No. 62/209,526, filed on Aug. 25, 2015. The entire contents of each of the foregoing patent applications are incorporated herein by reference.

This application is related to U.S. Provisional Application No. 61/733,518, filed on Dec. 5, 2012; U.S. Provisional Application No. 61/793,530, filed on Mar. 15, 2013; U.S. Provisional Application No. 61/886,916, filed on Oct. 4, 2013; U.S. Provisional Application No. 61/892,188, filed on Oct. 17, 2013; PCT Application No. PCT/US2013/073349, filed on Dec. 5, 2013; U.S. patent application Ser. No. 14/650,128, filed on Jun. 5, 2015, now U.S. Pat. No. 10,125,369, issued on Nov. 13, 2018, and U.S. patent application Ser. No. 16/155,965, filed on Oct. 10, 2018. The entire contents of each of the foregoing patent applications are hereby incorporated herein by reference.

SEQUENCE LISTING

The instant application contains a Sequence Listing which has been submitted electronically in ASCII format and is hereby incorporated by reference in its entirety. Said ASCII copy, created on Dec. 20, 2019, is named 121301_04404_SL.txt and is 188,270 bytes in size.

BACKGROUND OF THE INVENTION

Proprotein convertase subtilisin kexin 9 (PCSK9) is a member of the subtilisin serine protease family. The other eight mammalian subtilisin proteases, PCSK1-PCSK8 (also called PC1/3, PC2, furin, PC4, PC5/6, PACE4, PC7, and S1P/SKI-1) are proprotein convertases that process a wide variety of proteins in the secretory pathway and play roles in diverse biological processes (Bergeron, F. (2000) *J. Mol. Endocrinol.* 24, 1-22, Gensberg, K., (1998) *Semin. Cell Dev. Biol.* 9, 11-17, Seidah, N. G. (1999) *Brain Res.* 848, 45-62, Taylor, N. A., (2003) *FASEB J.* 17, 1215-1227, and Zhou, A., (1999) *J. Biol. Chem.* 274, 20745-20748).

PCSK9 has been proposed to play a role in cholesterol metabolism. PCSK9 mRNA expression is down-regulated by dietary cholesterol feeding in mice (Maxwell, K. N., (2003) *J. Lipid Res.* 44, 2109-2119), up-regulated by statins in HepG2 cells (Dubuc, G., (2004) *Arterioscler. Thromb. Vasc. Biol.* 24, 1454-1459), and up-regulated in sterol regulatory element binding protein (SREBP) transgenic mice (Horton, J. D., (2003) *Proc. Natl. Acad. Sci. USA* 100, 12027-12032), similar to the cholesterol biosynthetic enzymes and the low-density lipoprotein receptor (LDLR). Furthermore, PCSK9 missense mutations have been found to be associated with a form of autosomal dominant hypercholesterolemia (Hchola3) (Abifadel, M., et al. (2003) *Nat. Genet.* 34, 154-156, Timms, K. M., (2004) *Hum. Genet.* 114, 349-353, Leren, T. P. (2004) *Clin. Genet.* 65, 419-422). PCSK9 may also play a role in determining LDL cholesterol levels in the general population, because single-nucleotide polymorphisms (SNPs) have been associated with cholesterol levels in a Japanese population (Shioji, K., (2004) *J. Hum. Genet.* 49, 109-114).

Autosomal dominant hypercholesterolemias (ADHs) are monogenic diseases in which patients exhibit elevated total and LDL cholesterol levels, tendon xanthomas, and premature atherosclerosis (Rader, D. J., (2003) *J. Clin. Invest.* 111, 1795-1803). The pathogenesis of ADHs and a recessive form, autosomal recessive hypercholesterolemia (ARH) (Cohen, J. C., (2003) *Curr. Opin. Lipidol.* 14, 121-127), is due to defects in LDL uptake by the liver. ADH may be caused by LDLR mutations, which prevent LDL uptake, or by mutations in the protein on LDL, apolipoprotein B, which binds to the LDLR. ARH is caused by mutations in the ARH protein that are necessary for endocytosis of the LDLR-LDL complex via its interaction with clathrin. Therefore, if PCSK9 mutations are causative in Hchola3 families, it seems likely that PCSK9 plays a role in receptor-mediated LDL uptake.

Overexpression studies point to a role for PCSK9 in controlling LDLR levels and, hence, LDL uptake by the liver (Maxwell, K. N. (2004) *Proc. Natl. Acad. Sci. USA* 101, 7100-7105, Benjannet, S., et al. (2004) *J. Biol. Chem.* 279, 48865-48875, Park, S. W., (2004) *J. Biol. Chem.* 279, 50630-50638). Adenoviral-mediated overexpression of mouse or human PCSK9 for 3 or 4 days in mice results in elevated total and LDL cholesterol levels; this effect is not seen in LDLR knockout animals (Maxwell, K. N. (2004) *Proc. Natl. Acad. Sci. USA* 101, 7100-7105, Benjannet, S., et al. (2004) *J. Biol. Chem.* 279, 48865-48875, Park, S. W., (2004) *J. Biol. Chem.* 279, 50630-50638). In addition, PCSK9 overexpression results in a severe reduction in hepatic LDLR protein, without affecting LDLR mRNA levels, SREBP protein levels, or SREBP protein nuclear to cytoplasmic ratio.

While hypercholesterolemia itself is asymptomatic, long-standing elevation of serum cholesterol can lead to atherosclerosis. Over a period of decades, chronically elevated serum cholesterol contributes to formation of atheromatous plaques in the arteries which can lead to progressive stenosis or even complete occlusion of the involved arteries. In addition, smaller plaques may rupture and cause a clot to form and obstruct blood flow resulting in, for example, myocardial infarction and/or stroke. If the formation of the stenosis or occlusion is gradual, blood supply to the tissues and organs slowly diminishes until organ function becomes impaired.

Accordingly, there is a need in the art for effective treatments for PCSK9-associated diseases, such as a hyperlipidemia, e.g., hypercholesterolemia.

SUMMARY OF THE INVENTION

The present invention is based, at least in part, on the surprising discovery that a single dose of a double-stranded RNAi agent comprising chemical modifications shows an exceptional potency and durability to inhibit expression of PCSK9. Specifically, a single fixed dose, e.g., a fixed dose of about 300 mg to about 500 mg, of RNAi agents targeting a human PCSK9 gene, e.g., nucleotides 3544-3623 of a human PCSK9 gene (nucleotides 3544-3623 of SEQ ID NO:1), e.g., nucleotides 3601-3623 of SEQ ID NO:1, including a GalNAc ligand are shown herein to be exceptionally effective and durable in silencing the activity of a PCSK9 gene.

Accordingly, the present invention provides methods for inhibiting expression of a PCSK9 gene in a subject and methods for treating a subject having a disorder that would benefit from inhibiting or reducing the expression of a PCSK9 gene, e.g., a disorder mediated by PCSK9 expression, such as a hyperlipidemia, e.g., hypercholesterolemia, using iRNA compositions which effect the RNA-induced silencing complex (RISC)-mediated cleavage of RNA transcripts of a PCSK9 gene.

In one aspect, the methods of the present invention for inhibiting expression of a PCSK9 gene in a subject and methods for treating a subject having a disorder that would benefit from inhibiting or reducing the expression of a PCSK9 gene, e.g., a disorder mediated by PCSK9 expression, such as a hyperlipidemia, e.g., hypercholesterolemia, include administering to a subject a fixed dose of about 25 mg to about 800 mg of a double-stranded ribonucleic acid (RNAi) agent, wherein the double-stranded RNAi agent comprises a sense strand and an antisense strand forming a double stranded region, wherein the sense strand comprises at least 15 contiguous nucleotides differing by no more than 3 nucleotides from the nucleotide sequence of SEQ ID NO:1 and the antisense strand comprises at least 15 contiguous nucleotides differing by no more than 3 nucleotides from the nucleotide sequence of SEQ ID NO:2, wherein substantially all of the nucleotides of the sense strand and substantially all of the nucleotides of the antisense strand are modified nucleotides, and wherein the sense strand is conjugated to a ligand attached at the 3'-terminus.

In one aspect, the present invention provides methods of inhibiting the expression of a PCSK9 gene in a subject. The methods include comprising administering to the subject a fixed dose of about 25 mg to about 800 mg of a double-stranded ribonucleic acid (RNAi) agent, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby inhibiting the expression of the PCSK9 gene in the subject.

In another aspect, the present invention provides methods of decreasing the level of low density lipoprotein (LDLc) in a subject, comprising administering to the subject a fixed dose of about 25 mg to about 800 mg of a double-stranded ribonucleic acid (RNAi) agent, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby decreasing the level of LDLc in the subject.

In another aspect, the present invention provides methods of treating a subject having a disorder that would benefit from reduction in PCSK9 expression. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1 thereby treating the subject having a disorder that would benefit from reduction in PCSK9 expression.

In yet another aspect, the present invention provides methods of treating a subject having hyperlipidemia. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby treating the subject having hypercholesterolemia.

The fixed dose may administered to the subject at an interval of once a week, once every two weeks, once a month, once a quarter, or bianually.

In one embodiment, the subject is administered a fixed dose of about 25 mg to about 50 mg once a week. In another embodiment, the subject is administered a fixed dose of about 50 mg to about 100 mg once every two weeks. In another embodiment, the subject is administered a fixed dose of about 100 mg to about 200 mg once a month. In yet another embodiment, the subject is administered a fixed dose of about 300 mg to about 800 mg once a quarter. In another embodiment, the subject is administered a fixed dose of about 300 mg to about 800 mg biannually.

The present invention also provides methods in which the RNAi agent is administered in a dosing regimen that includes a loading phase and a maintenance phase.

Accordingly, in one aspect, the present invention provides methods of inhibiting the expression of a PCSK9 gene in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering a fixed dose of about 25 mg to about 100 mg of the RNAi agent to the subject about once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby inhibiting the expression of the PCSK9 gene in the subject.

In another aspect, the present invention provides methods of decreasing the level of low density lipoprotein (LDLc) in a subject. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby decreasing the level of LDLc in the subject.

In another aspect, the present invention provides methods of treating a subject having a disorder that would benefit from reduction in PCSK9 expression. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby treating the subject having a disorder that would benefit from reduction in PCSK9 expression.

In yet another aspect, the present invention provides methods of treating a subject having hyperlipidemia. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby treating the subject having hyperlipidemia.

The double stranded RNAi agent may be administered to the subject subcutaneously, e.g., by subcutaneous injection, or intramuscularly.

In one embodiment, the antisense strand comprises a nucleotide sequence selected from the group consisting of any one of the unmodified nucleotide sequences provided in Table 1. In one embodiment, the double-stranded RNAi agent targets nucleotides 3601-3623 of SEQ ID NO:1. In one embodiment, the agent targeting nucleotides 3601-3623 of SEQ ID NO:1 is AD-60212.

In one embodiment, the antisense strand comprises the nucleotide sequence 5'-ACAAAAGCAAAACAGGUCUAGAA-3' (SEQ ID NO: 685).

In one embodiment, the sense strand comprises the nucleotide sequence 5'-CUAGACCUGUUUGCUUUUGU-3' (SEQ ID NO: 686).

In one embodiment, the double-stranded ribonucleic acid RNAi agent comprises at least one modified nucleotide.

In one embodiment, substantially of the nucleotides of the sense strand are modified nucleotides. In another embodiment, substantially all of the nucleotides of the antisense strand are modified nucleotides. In yet another embodiment, substantially of the nucleotides of the sense strand and substantially all of the nucleotides of the antisense strand are modified nucleotides.

In one embodiment, all of the nucleotides of the sense strand are modified nucleotides. In another embodiment, all of the nucleotides of the antisense strand are modified nucleotides. In yet another embodiment, all of the nucleotides of the sense strand and all of the nucleotides of the antisense strand are modified nucleotides.

In one aspect, the present invention provides methods of inhibiting the expression of a PCSK9 gene in a subject. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUUUGCUUUUGU-3' (SEQ ID NO: 686), wherein substantially all of the nucleotides of the sense strand and substantially all of the nucleotides of the antisense strand are modified nucleotides, thereby inhibiting expression of the PCSK9 gene in the subject.

In another aspect, the present invention provides methods of decreasing the level of low density lipoprotein (LDLc) in a subject. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUUUGCUUUUGU-3' (SEQ ID NO: 686), wherein substantially all of the nucleotides of the sense strand and substantially all of the nucleotides of the antisense strand are modified nucleotides, thereby decreasing the level of LDLc in the subject.

In another aspect, the present invention provides methods of treating a subject having a disorder that would benefit from reduction in PCSK9 expression, comprising administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUUUGCUUUUGU-3' (SEQ ID NO: 686), wherein substantially all of the nucleotides of the sense strand and substantially all of the nucleotides of the antisense strand are modified nucleotides, thereby treating the subject having a disorder that would benefit from reduction in PCSK9 expression.

In yet another aspect, the present invention provides methods of treating a subject having hyperlipidemia. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUUUGCUUUUGU-3' (SEQ ID NO: 686), wherein substantially all of the nucleotides of the sense strand and substantially all of the nucleotides of the antisense strand are modified nucleotides, thereby treating the subject having hyperlipidemia.

In one aspect, the present invention provides methods of inhibiting the expression of a PCSK9 gene in a subject. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUUUGCUUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby inhibiting expression of the PCSK9 gene in the subject.

In another aspect, the present invention provides methods of decreasing the level of low density lipoprotein (LDLc) in a subject. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGCUUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby decreasing the level of LDLc in the subject.

In another aspect, the present invention provides methods of treating a subject having a disorder that would benefit from reduction in PCSK9 expression, comprising administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby treating the subject having a disorder that would benefit from reduction in PCSK9 expression.

In yet another aspect, the present invention provides methods of treating a subject having hyperlipidemia. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGCUUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby treating the subject having hyperlipidemia.

The fixed dose may administered to the subject at an interval of once a week, once every two weeks, once a month, once a quarter, or bianually.

In one embodiment, the subject is administered a fixed dose of about 25 mg to about 50 mg once a week. In another embodiment, the subject is administered a fixed dose of about 50 mg to about 100 mg once every two weeks. In another embodiment, the subject is administered a fixed dose of about 100 mg to about 200 mg once a month. In yet another embodiment, the subject is administered a fixed dose of about 300 mg to about 800 mg once a quarter. In another embodiment, the subject is administered a fixed dose of about 300 mg to about 800 mg biannually.

In one aspect, the present invention provide methods of inhibiting the expression of a PCSK9 gene in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, thereby inhibiting expression of the PCSK9 gene in the subject.

In another aspect, the present invention provides methods of decreasing the level of low density lipoprotein (LDLc) in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUA-GAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, thereby decreasing the level of LDLc in the subject.

In another aspect, the present invention provides methods of treating a subject having a disorder that would benefit from reduction in PCSK9 expression. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGCUUUUGU-3' (SEQ ID NO: 686), wherein substantially all of the nucleotides of the sense strand and substantially all of the nucleotides of the antisense strand are modified nucleotides, thereby treating the subject having a disorder that would benefit from reduction in PCSK9 expression.

In yet another aspect, the present invention provides methods of treating a subject having hyperlipidemia. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, thereby treating the subject having hyperlipidemia.

In one aspect, the present invention provide methods of inhibiting the expression of a PCSK9 gene in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby inhibiting expression of the PCSK9 gene in the subject.

In another aspect, the present invention provides methods of decreasing the level of low density lipoprotein (LDLc) in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUA-GAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby decreasing the level of LDLc in the subject.

In another aspect, the present invention provides methods of treating a subject having a disorder that would benefit from reduction in PCSK9 expression. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGCUUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby treating the subject having a disorder that would benefit from reduction in PCSK9 expression.

In yet another aspect, the present invention provides methods of treating a subject having hyperlipidemia. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the antisense strand comprises the nucleotide sequence 5'-ACAAAAGCAAAACAGGUCUAGAA-3' (SEQ ID NO: 685) and the sense strand comprises the nucleotide sequence 5'-CUAGACCUGUTUUGC-UUUUGU-3' (SEQ ID NO: 686), wherein substantially all of the nucleotides of the sense strand and substantially all of the nucleotides of the antisense strand are modified nucleotides, and administering to the subject a therapeutically effective amount of an anti-PCSK9 antibody, or antigen-binding fragment thereof, thereby treating the subject having hyperlipidemia.

In one embodiment, the subject is a human.

In one embodiment, the disorder that would benefit from reduction in PCSK9 expression is hyperlipidemia, such as hypercholesterolemia.

In one embodiment, the hyperlipidemia is hypercholesterolemia.

The double stranded RNAi agent may be administered to the subject subcutaneously, e.g., by subcutaneous injection, or intramuscularly.

In one embodiment, the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfg-GfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage.

In one embodiment, the double-stranded ribonucleic acid RNAi agent further comprises a ligand.

In one embodiment, the ligand is conjugated to the 3' end of the sense strand of the double-stranded ribonucleic acid RNAi agent.

In one embodiment, the ligand is an N-acetylgalactosamine (GalNAc) derivative.

In one embodiment, the ligand is

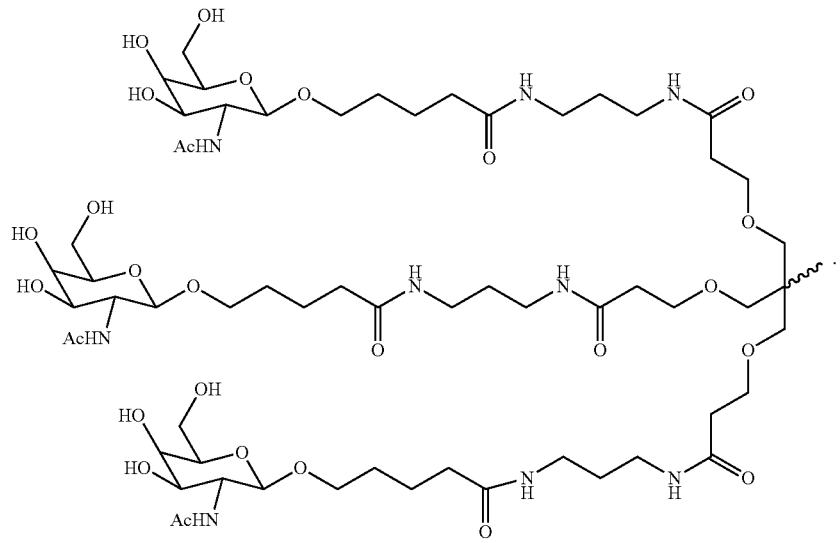 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the double-stranded ribonucleic acid RNAi agent is conjugated to the ligand as shown in the following schematic In one embodiment, the methods of the invention further comprise determining an LDLR genotype or phenotype of the subject.

In one embodiment, administering the double-stranded RNAi agent results in a decrease in serum cholesterol in the subject and/or a decrease in PCSK9 protein accumulation.

In one embodiment, the methods of the invention further comprise determining the serum cholesterol level in the subject.

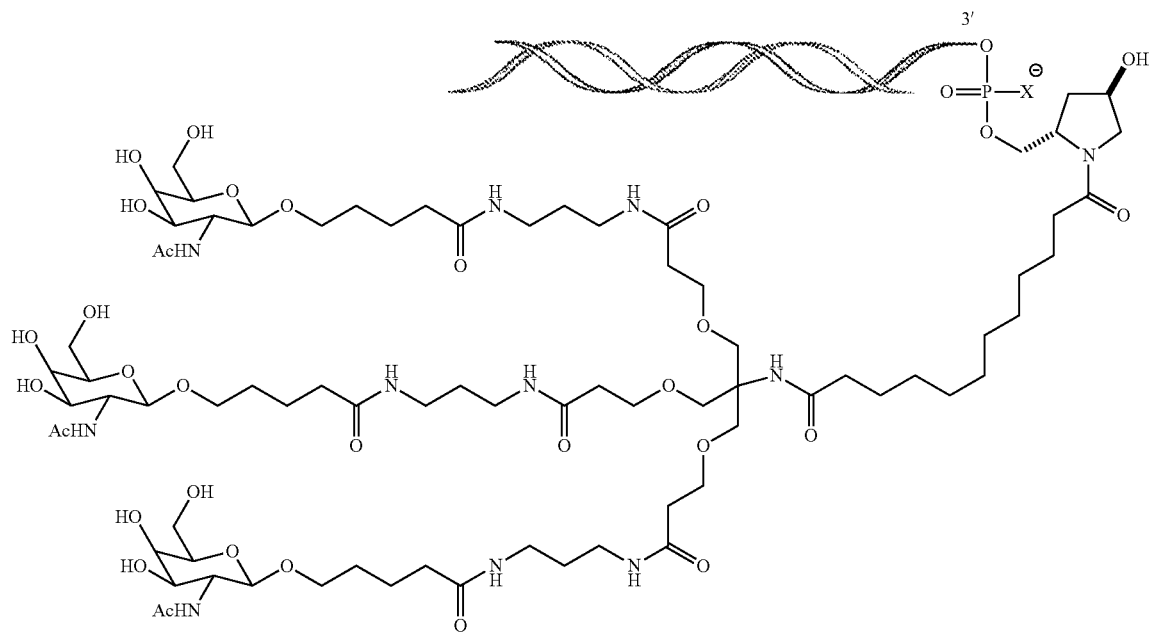

and, wherein X is O or S. In one embodiment, the X is O.

In one embodiment, PCSK9 expression is inhibited by at least about 30%.

In one embodiment, the methods of the invention further comprise comprising administering an additional therapeutic agent to the subject, e.g., a statin and/or an anti-PCSK9 antibody. In one embodiment, the anti-PCSK9 antibody is selected from the group consisting of alirocumab (Praluent), evolocumab (Repatha), and bococizumab.

In one embodiment, the RNAi agent is administered as a pharmaceutical composition.

The RNAi agent may be administered in an unbuffered solution, such as saline or water., or administered with a buffer solution. In one embodiment, the buffer solution comprises acetate, citrate, prolamine, carbonate, or phosphate or any combination thereof. In another embodiment, the buffer solution is phosphate buffered saline (PBS).

In one aspect, the present invention provides methods of inhibiting the expression of a PCSK9 gene in a subject. The methods include administering to the subject a single fixed dose of about 25 mg to about 800 mg of a double-stranded ribonucleic acid (RNAi) agent, wherein the double-stranded RNAi agent comprises a sense strand and an antisense strand forming a double stranded region, wherein the sense strand comprises the nucleotide sequence of 5'-csusagacCfuGfud-Tuugcuuuugu-3' (SEQ ID NO: 687) and the antisense strand comprises the nucleotide sequence of 5'-asCfsaAfAfAfgC-faAfaAfcAfgGfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby inhibiting expression of the PCSK9 gene in the subject.

In another aspect, the present invention provides methods of decreasing the level of low density lipoprotein (LDLc) in a subject. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby decreasing the level of LDLc in the subject.

In another aspect, the present invention provides methods of treating a subject having a disorder that would benefit from reduction in PCSK9 expression. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfg-GfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby treating the subject having a disorder that would benefit from reduction in PCSK9 expression.

In yet another aspect, the present invention provides methods of treating a subject having hyperlipidemia. The methods include administering to the subject a fixed dose of about 25 mg to about 800 mg of a double-stranded ribonucleic acid (RNAi) agent, wherein the double-stranded RNAi agent comprises a sense strand and an antisense strand forming a double stranded region, wherein the sense strand comprises the nucleotide sequence of 5'-csusagacCfuGfud-Tuugcuuuugu-3' (SEQ ID NO: 687) and the antisense strand comprises the nucleotide sequence of 5'-asCfsaAfAfAfgC-faAfaAfcAfgGfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby treating the subject having hyperlipidemia.

In one embodiment, the subject is administered a fixed dose of about 200 mg to about 800 mg once a quarter. In another embodiment, the subject is administered a fixed dose of about 200 mg to about 800 mg biannually.

In one aspect, the present invention provides methods of inhibiting the expression of a PCSK9 gene in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 800 mg of the RNAi agent once a quarter, wherein the double-stranded RNAi agent comprises a sense strand and an antisense strand forming a double region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuag-sasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby inhibiting expression of the PCSK9 gene in the subject.

In another aspect, the present invention provides methods of decreasing the level of low density lipoprotein (LDLc) in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfg-GfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby decreasing the level of LDLc in the subject.

In yet another aspect, the present invention provides methods of treating a subject having a disorder that would benefit from reduction in PCSK9 expression. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby treating the subject having a disorder that would benefit from reduction in PCSK9 expression.

In another aspect, the present invention provides methods of treating a subject having hyperlipidemia. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering to the subject a fixed dose of about 25 mg to about 100 mg of the RNAi agent once a quarter, wherein the double-stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuagsasa-3' (SEQ ID NO: 688) (AD-60212), wherein a, g, c and u are 2'-O-methyl (2'-OMe) A, G, C, or U; Af, Gf, Cf or Uf are 2'-fluoro A, G, C or U; dT is 2'-deoxythymidine; and s is a phosphorothioate linkage, and administering to the subject a therapeutically effective amount of an anti-PCSK9 antibody, or antigen-binding fragment thereof, thereby treating the subject having hyperlipidemia.

In one embodiment, the subject is administered the maintenance does as a fixed dose of about 200 mg to about 800 mg once a quarter. In another embodiment, the subject is administered the maintenance does as a fixed dose of about 200 mg to about 800 mg biannually.

In one embodiment, the double-stranded ribonucleic acid RNAi agent further comprises a ligand.

In one embodiment, the ligand is conjugated to the 3' end of the sense strand of the double-stranded ribonucleic acid RNAi agent.

In one embodiment, the ligand is an N-acetylgalactosamine (GalNAc) derivative.

In one embodiment the ligand is

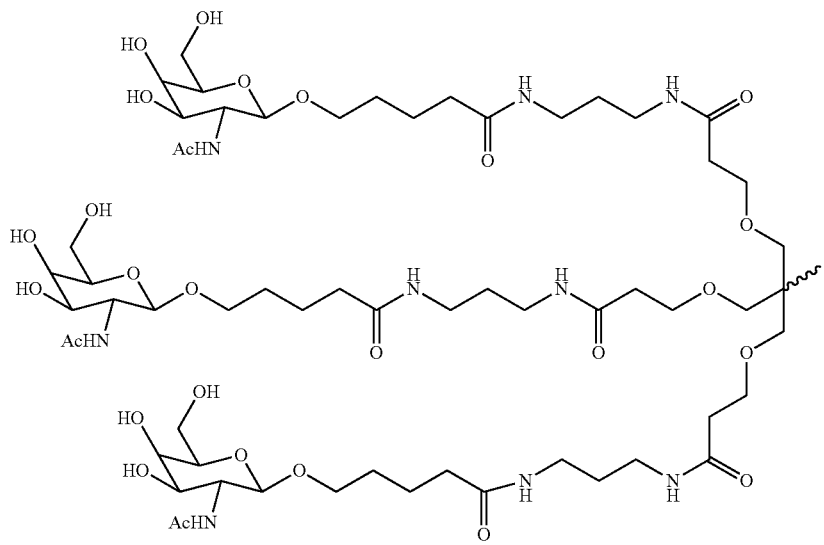

In one embodiment, the double-stranded ribonucleic acid RNAi agent is conjugated to the ligand as shown in the following schematic

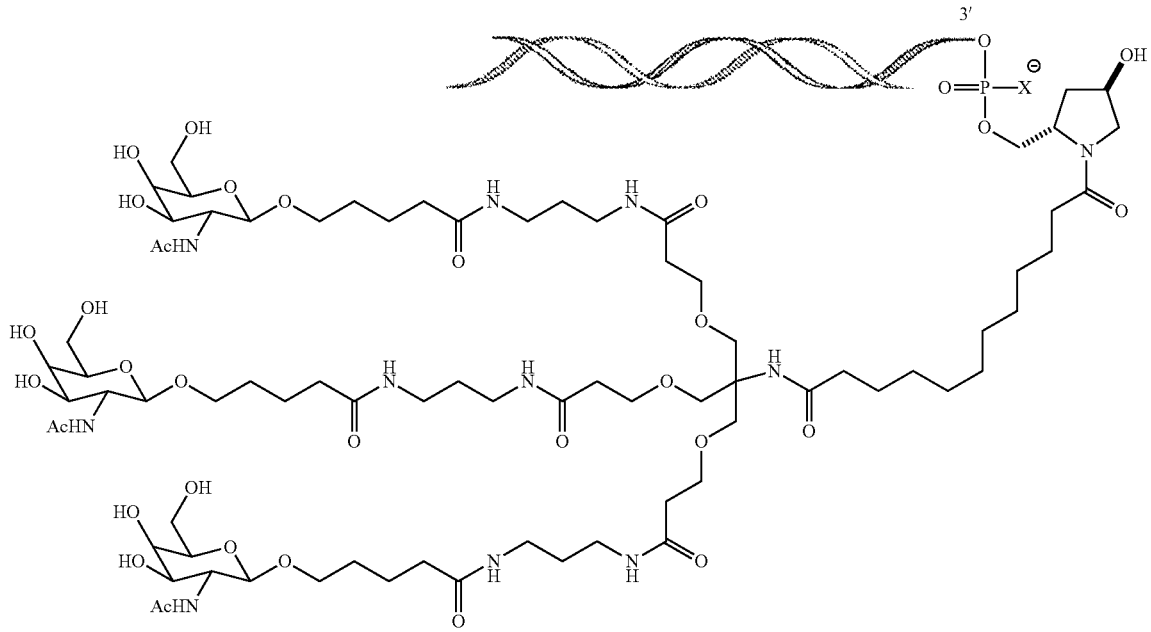

and, wherein X is O or S. In one embodiment, the X is O.

In one embodiment, the anti-PCSK9 antibody, or antigen-binding fragment thereof, is selected from the group consisting of alirocumab (Praluent), evolocumab (Repatha), and bococizumab.

In one embodiment, the methods further include administering an additional therapeutic agent, e.g., a statin, to the subject.

In one aspect, the present invention provides kits for performing the method of the invention. The kits include the RNAi agent, and instructions for use, and optionally, means for administering the RNAi agent to the subject.

The present invention is further illustrated by the following detailed description and drawings.

DETAILED DESCRIPTION OF THE INVENTION

Figure 1:
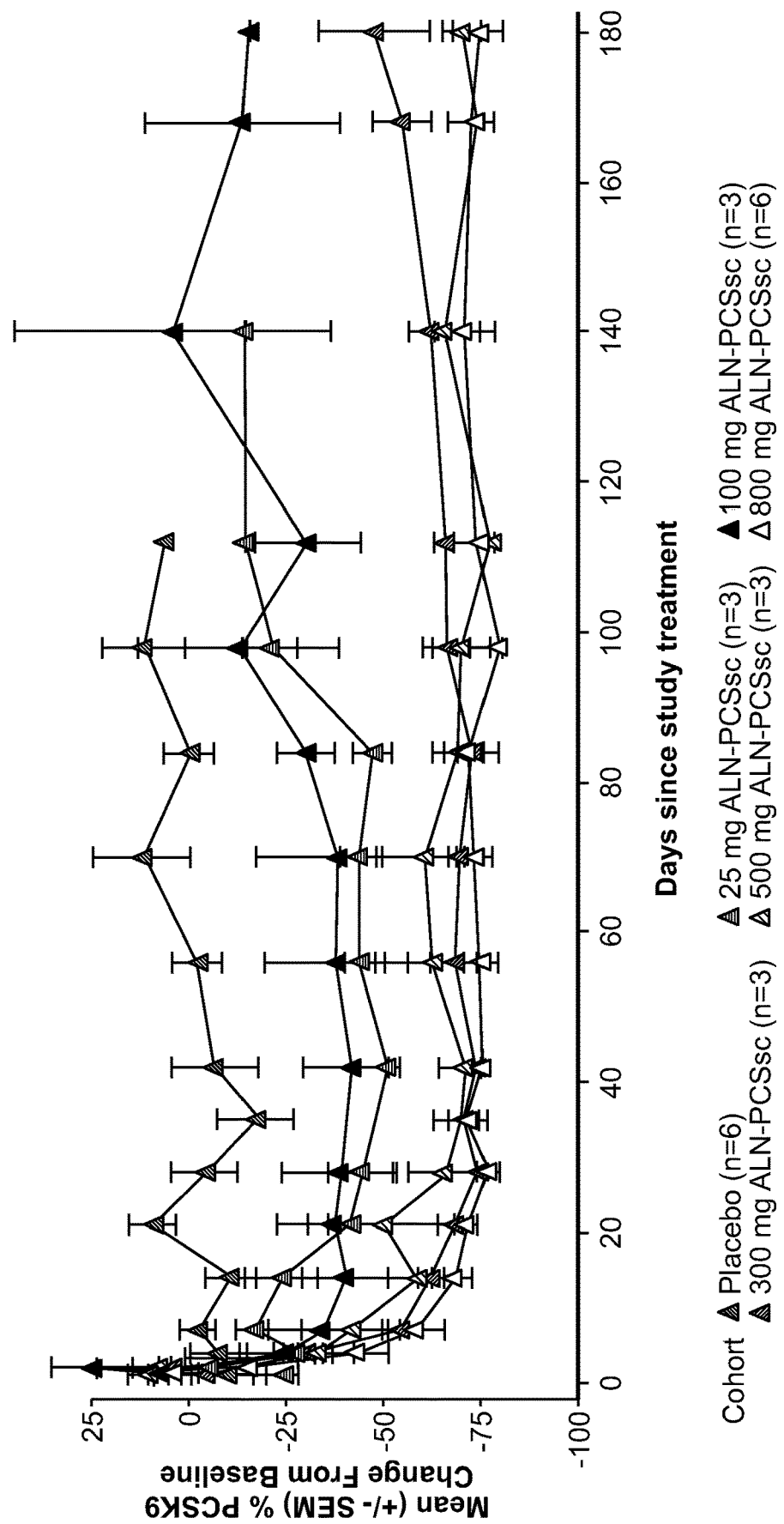
FIG. 1 is a graph showing the knockdown of PCSK9 protein levels, shown as a percent mean PCSK9 knockdown relative to baseline, in subjects receiving a single fixed dose of AD-60212.

The present invention is based, at least in part, on the surprising discovery that a single dose of a double-stranded RNAi agent comprising chemical modifications shows an exceptional potency and durability to inhibit expression of PCSK9. Specifically, a single fixed dose, e.g., a fixed dose of about 300 mg to about 500 mg, of RNAi agents targeting a human PCSK9 gene, e.g., nucleotides 3544-3623 of a human PCSK9 gene (nucleotides 3544-3623 of SEQ ID NO:1), e.g., nucleotides 3601-3623 of SEQ ID NO:1, including a GalNAc ligand are shown herein to be exceptionally effective and durable in silencing the activity of a PCSK9 gene.

Accordingly, the present invention provides methods for inhibiting expression of a PCSK9 gene and methods for treating a subject having a disorder that would benefit from inhibiting or reducing the expression of a PCSK9 gene, e.g., a disorder mediated by PCSK9 expression, such as a hyperlipidemia, e.g., hypercholesterolemia, using iRNA compositions which effect the RNA-induced silencing complex (RISC)-mediated cleavage of RNA transcripts of a PCSK9 gene.

The following detailed description discloses how to make and use compositions containing iRNAs to inhibit the expression of a PCSK9 gene, as well as compositions, uses, and methods for treating subjects having diseases and disorders that would benefit from inhibition and/or reduction of the expression of this gene.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise. For example, "sense strand or antisense strand" is understood as "sense strand or antisense strand or sense strand and antisense strand."

The term "about" is used herein to mean within the typical ranges of tolerances in the art. For example, "about" can be understood as about 2 standard deviations from the mean. In certain embodiments, about means+10%. In certain embodiments, about means+5%. When about is present before a series of numbers or a range, it is understood that "about" can modify each of the numbers in the series or range.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21 nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, a duplex with an overhang of "no more than 2 nucleotides" has a 2, 1, or 0 nucleotide overhang. When "no more than" is present before a series of numbers or a range, it is understood that "no more than" can modify each of the numbers in the series or range.

As used herein, "PCSK9" refers to the proprotein convertase subtilisin kexin 9 gene or protein. PCSK9 is also known as FH3, HCHOLA3, NARC-1, or NARC1. The term PCSK9 includes human PCSK9, the amino acid and nucleotide sequence of which may be found in, for example, GenBank Accession No. GI:299523249 (SEQ ID NO:1); mouse PCSK9, the amino acid and nucleotide sequence of which may be found in, for example, GenBank Accession No. GI:163644257; rat PCSK9, the amino acid and nucleotide sequence of which may be found in, for example, GenBank Accession No. GI:77020249.

Additional examples of PCSK9 mRNA sequences are readily available using publicly available databases, e.g., GenBank, UniProt, and OMIM.

In one embodiment, the subject is a human, such as a human being treated or assessed for a disease, disorder or condition that would benefit from reduction in PCSK9 expression; a human at risk for a disease, disorder or condition that would benefit from reduction in PCSK9 expression; a human having a disease, disorder or condition that would benefit from reduction in PCSK9 expression; and/or human being treated for a disease, disorder or condition that would benefit from reduction in PCSK9 expression as described herein.

As used herein, the terms "treating" or "treatment" refer to a beneficial or desired result including, but not limited to, alleviation or amelioration of one or more symptoms associated with a disorder that would benefit from reduction in PCSK9 expression, or slowing or reversing the progression of such a disorder, whether detectable or undetectable. For example, in the context of hyperlipidemia, treatment may include a decrease in serum lipid levels, e.g., a decrease in low density lipoprotein cholesterol (LDLc). "Treatment" can also mean prolonging survival as compared to expected survival in the absence of treatment.

As used herein, "prevention" or "preventing," when used in reference to a disease, disorder or condition thereof, that would benefit from a reduction in expression of a PCSK9 gene, refers to a reduction in the likelihood that a subject will develop a symptom associated with a disease, disorder, or condition mediated by PCSK9 expression, e.g., a symptom such as cardiovascular disease, e.g., coronary artery disease (CAD) (also known as coronary heart disease (CHD)), or transient ischemic attack (TIA) or stroke. The likelihood of developing a such a symptom is reduced, for example, when an individual having one or more risk factors (e.g., diabetes, previous personal history of CHD or noncoronary atherosclerosis (e.g., abdominal aortic aneurysm, peripheral artery disease, and carotid artery stenosis), family history of cardiovascular disease, e.g., in male relatives younger than 50 years or in female relatives younger than age 60 years, tobacco use, hypertension, and/or obesity (BMI ≥30)) for a disease, disorder, or condition mediated by PCSK9 expression, e.g., hypercholesterolemia, either fails to develop, for example, coronary artery disease, or develops, e.g., coronary artery disease, with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention. Prevention can require administration of more than one dose.

The interchangeably used terms "PCSK9-associated disease" and "disorder that would benefit from a reduction in PCSK9 expression," as used herein, are intended to include any disease, disorder, or condition associated with the PCSK9 gene or protein. Such a disease may be caused, for example, by excess production of the PCSK9 protein, by PCSK9 gene mutations, by abnormal cleavage of the PCSK9 protein, by abnormal interactions between PCSK9 and other proteins or other endogenous or exogenous substances. Exemplary PCSK9-associated diseases include lipidemias, e.g., a hyperlipidemia, and other forms of lipid imbalance such as hypercholesterolemia, hypertriglyceridemia and the pathological conditions associated with these disorders, e.g., CHD and atherosclerosis.

As used herein the term "hypercholesterolemia" refers to a form of hyperlipidemia (elevated levels of lipids in the blood) in which there are high levels of cholesterol in the serum of a subject, e.g., at least about 240 mg/dL of total cholesterol.

As used herein, the term "cardiovascular disease" refers to a disease affecting the heart or blood vessels, which includes, for example, arteriosclerosis, coronary artery disease (or narrowing of the arteries), heart valve disease, arrhythmia, heart failure, hypertension, orthostatic hypotension, shock, endocarditis, diseases of the aorta and its branches, disorders of the peripheral vascular system, heart attack, cardiomyopathy, and congenital heart disease.

"Therapeutically effective amount," as used herein, is intended to include the amount of an RNAi agent that, when administered to a patient for treating a PCSK9 associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by PCSK9 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of a PCSK9-associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

As used herein, "target sequence" refers to a contiguous portion of the nucleotide sequence of an mRNA molecule formed during the transcription of a PCSK9 gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of a PCSK9 gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. In some embodiments, the target sequence is about 19 to about 30 nucleotides in length. In other embodiments, the target sequence is about 19 to about 25 nucleotides in length. In still other embodiments, the target sequence is about 19 to about 23 nucleotides in length. In some embodiments, the target sequence is about 21 to about 23 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table B). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent," "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of PCSK9 in a cell, e.g., a cell within a subject, such as a mammalian subject.

In one embodiment, an RNAi agent of the invention includes a single stranded RNA that interacts with a target RNA sequence, e.g., a PCSK9 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a PCSK9 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150:883-894.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA" refers to a complex of ribonucleic acid molecules, having a duplex structure comprising two anti-parallel and substantially complementary nucleic acid strands, referred to as having "sense" and "antisense" orientations with respect to a target RNA, i.e., a PCSK9 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides. In some embodiments, the hairpin loop can be 10 or fewer nucleotides. In some embodiments, the hairpin loop can be 8 or fewer unpaired nucleotides. In some embodiments, the hairpin loop can be 4-10 unpaired nucleotides. In some embodiments, the hairpin loop can be 4-8 nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs. In one embodiment of the RNAi agent, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide.

In one embodiment, an RNAi agent of the invention is a dsRNA agent, each strand of which comprises 19-23 nucleotides that interacts with a target RNA sequence, i.e., a PCSK9 target mRNA sequence. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

In another embodiment, an RNAi agent of the invention is a dsRNA of 24-30 nucleotides that interacts with a target RNA sequence, e.g., a PCSK9 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment of the dsRNA, at least one strand comprises a 3' overhang of at least 1 nucleotide. In another embodiment, at least one strand comprises a 3' overhang of at least 2 nucleotides, e.g., 2, 3, 4, 5, 6, 7, 9, 10, 11, 12, 13, 14, or 15 nucleotides. In other embodiments, at least one strand of the RNAi agent comprises a 5' overhang of at least 1 nucleotide. In certain embodiments, at least one strand comprises a 5' overhang of at least 2 nucleotides, e.g., 2, 3, 4, 5, 6, 7, 9, 10, 11, 12, 13, 14, or 15 nucleotides. In still other embodiments, both the 3' and the 5' end of one strand of the RNAi agent comprise an overhang of at least 1 nucleotide. In certain embodiments, the antisense strand of a dsRNA has a 1-10 nucleotide, e.g., 0-3, 1-3, 2-4, 2-5, 4-10, 5-10, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate. In certain embodiments, the overhang includes a self-complementary portion such that the overhang is capable of forming a hairpin structure that is stable under physiological conditions.

"Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a PCSK9 mRNA. As used herein, the term "region of complementarity" refers to the region on the antisense strand that is substantially complementary to a sequence, for example a target sequence, e.g., a PCSK9 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, 2, or 1 nucleotides of the 5'- and/or 3'-terminus of the iRNA. In one embodiment, a double stranded RNAi agent of the invention includes a nucleotide mismatch in the antisense strand. In another embodiment, a double stranded RNAi agent of the invention includes a nucleotide mismatch in the sense strand. In one embodiment, the nucleotide mismatch is, for example, within 5, 4, 3, 2, or 1 nucleotides from the 3'-terminus of the iRNA. In another embodiment, the nucleotide mismatch is, for example, in the 3'-terminal nucleotide of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding PCSK9). For example, a polynucleotide is complementary to at least a part of a PCSK9 mRNA if the sequence is substantially complementary to a non-interrupted portion of an mRNA encoding PCSK9.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

In one aspect of the invention, an agent for use in the methods and compositions of the invention is a single-stranded antisense RNA molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

II. Methods of the Invention

The present invention provides methods of inhibiting the expression of a Proprotein Convertase Subtilisin Kexin 9 (PCSK9) gene in a subject. The present invention also provides therapeutic and prophylactic methods for treating or preventing diseases and conditions that can be modulated by down regulating PCSK9 gene expression. For example, the compositions described herein can be used to treat lipidemia, e.g., a hyperlipidemia and other forms of lipid imbalance such as hypercholesterolemia, hypertriglyceridemia and the pathological conditions associated with these disorders such as heart and circulatory diseases. Other diseases and conditions that can be modulated by down regulating PCSK9 gene expression include lysosomal storage diseases including, but not limited to, Niemann-Pick disease, Tay-Sachs disease, Lysosomal acid lipase deficiency, and Gaucher Disease. The methods include administering to the subject a therapeutically effective amount or prophylactically effective amount of an RNAi agent of the invention. In some embodiments, the method includes administering an effective amount of a PCSK9 iRNA agent to a patient having a heterozygous LDLR genotype.

As PCSK9 regulates the levels of the LDL receptor, which in turn removes cholesterol-rich LDL particles from the plasma, the effect of the decreased expression of a PCSK9 gene preferably results in a decrease in LDLc (low density lipoprotein cholesterol) levels in the blood, and more particularly in the serum, of the mammal. In some embodiments, LDLc levels are decreased by at least 10%, 15%, 20%, 25%, 30%, 40%, 50%, 60%, 70%, 80%, 90% or more, as compared to pretreatment levels. Accordingly, the present invention also provides methods for lowering the level of low density cholesterol (LDLc) in the serum of a subject.

In certain embodiments of the invention, the double-stranded RNAi agent is administered to a subject as a fixed dose. A "fixed dose" (e.g., a dose in mg) means that one dose of an iRNA agent is used for all subjects regardless of any specific subject-related factors, such as weight. In other embodiments, an iRNA agent of the invention is administered to a subject as a weight-based dose. A "weight-based dose" (e.g., a dose in mg/kg) is a dose of the iRNA agent that will change depending on the subject's weight.

In certain embodiments of an RNAi agent is administered to the subject as a fixed dose of about 100 mg to about 700 mg, about 150 mg to about 700 mg, about 200 mg to about 700 mg, about 250 mg to about 700 mg, about 300 mg to about 700 mg, about 350 mg to about 700 mg, about 400 mg to about 700 mg, about 450 mg to about 700 mg, about 500 mg to about 700 mg, about 550 mg to about 700 mg, about 600 to about 700 mg, about 650 to about 700 mg, about 100 mg to about 650 mg, about 150 mg to about 650 mg, about 200 mg to about 650 mg, about 250 mg to about 650 mg, about 300 mg to about 650 mg, about 350 mg to about 650 mg, about 400 mg to about 650 mg, about 450 mg to about 650 mg, about 500 mg to about 650 mg, about 550 mg to about 650 mg, about 600 to about 650 mg, about 100 mg to about 600 mg, about 150 mg to about 600 mg, about 200 mg to about 600 mg, about 250 mg to about 600 mg, about 300 mg to about 600 mg, about 350 mg to about 600 mg, about 400 mg to about 600 mg, about 450 mg to about 600 mg, about 500 mg to about 600 mg, about 550 mg to about 600 mg, about 100 mg to about 550 mg, about 150 mg to about 550 mg, about 200 mg to about 550 mg, about 250 mg to about 550 mg, about 300 mg to about 550 mg, about 350 mg to about 550 mg, about 400 mg to about 550 mg, about 450 mg to about 550 mg, about 500 mg to about 550 mg, about 100 mg to about 500 mg, about 150 mg to about 500 mg, about 200 mg to about 500 mg, about 250 mg to about 500 mg, about 300 mg to about 500 mg, about 350 mg to about 500 mg, about 400 mg to about 500 mg, or about 450 mg to about 500 mg, e.g., a fixed dose of about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, or about 700 mg. Values and ranges intermediate to the foregoing recited values are also intended to be part of this invention.

The administration may be repeated, for example, on a regular basis. For example, the fixed dose may administered to the subject at an interval of once a week, once every two weeks, once a month, once a quarter, or bianually for six months or a year or longer, i.e., chronic administration.

In one embodiment, the subject is administered a fixed dose of about 25 mg to about 50 mg once a week. In another embodiment, the subject is administered a fixed dose of about 50 mg to about 100 mg once every two weeks. In another embodiment, the subject is administered a fixed dose of about 100 mg to about 200 mg once a month. In yet another embodiment, the subject is administered a fixed dose of about 300 mg to about 600 mg once a quarter. In another embodiment, the subject is administered a fixed dose of about 300 mg to about 600 mg biannually (i.e., twice a year).

Accordingly, in one aspect, the present invention provides methods of inhibiting the expression of a PCSK9 gene in a subject. The methods include administering to the subject a double-stranded ribonucleic acid (RNAi) agent, e.g., a dsRNA, of the invention (e.g., a pharmaceutical composition comprising a dsRNA of the invention), wherein a total of about 200 mg to about 600 mg of the double-stranded RNAi agent is administered to the subject every quarter or biannually, and wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1.

In another aspect, the present invention provides methods of decreasing the level of low density lipoprotein (LDLc) in a subject. The methods include administering to the subject a double-stranded ribonucleic acid (RNAi) agent, wherein a total of about 200 mg to about 600 mg of the double-stranded RNAi agent is administered to the subject every quarter or biannually, and wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby decreasing the level of LDLc in the subject.

In another aspect, the present invention provides methods of treating a subject having a disorder that would benefit from reduction in PCSK9 expression, such as a hyperlipidemia, e.g., hypercholesterolemia. The methods include administering to the subject a double-stranded ribonucleic acid (RNAi) agent, e.g., a dsRNA, of the invention (e.g., a pharmaceutical composition comprising a dsRNA of the invention), wherein a total of about 200 mg to about 600 mg of the double-stranded RNAi agent is administered to the subject every quarter or biannually, and wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1.

In yet another aspect, the present invention provides methods of treating a subject having hyperlipidemia, such as hypercholestrolemia. The methods include administering to the subject a double-stranded ribonucleic acid (RNAi) agent, e.g., a dsRNA, of the invention (e.g., a pharmaceutical composition comprising a dsRNA of the invention), wherein a total of about 200 mg to about 600 mg of the double-stranded RNAi agent is administered to the subject every quarter or biannually, and wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1.

As indicated above, the administration of the RNAi agents to a subject may be repeated on a regular basis, for example, at an interval of once a week, once every two weeks, once a month, once a quarter, or bianually.

Accordingly, in some embodiments, the RNAi agent is administered in a dosing regimen that includes a "loading phase" of closely spaced administrations that may be followed by a "maintenance phase", in which the RNAi agent is administered at longer spaced intervals. For example, after administration weekly or biweekly for one month, administration can be repeated once per month, for six months or a year or longer, i.e., chronic administration.

In one embodiment, the loading phase comprises a single administration of the RNAi agent during the first week. In another embodiment, the loading phase comprises a single administration of the RNAi agent during the first two weeks. In yet another embodiment, the loading phase comprises a single administration of the RNAi agent during the first month.

In certain embodiments of an RNAi agent is administered to the subject during a loading phase as a fixed dose of about 100 mg to about 700 mg, about 150 mg to about 700 mg, about 200 mg to about 700 mg, about 250 mg to about 700 mg, about 300 mg to about 700 mg, about 350 mg to about 700 mg, about 400 mg to about 700 mg, about 450 mg to about 700 mg, about 500 mg to about 700 mg, about 550 mg to about 700 mg, about 600 mg to about 700 mg, about 650 to about 700 mg, about 100 mg to about 650 mg, about 150 mg to about 650 mg, about 200 mg to about 650 mg, about 250 mg to about 650 mg, about 300 mg to about 650 mg, about 350 mg to about 650 mg, about 400 mg to about 650 mg, about 450 mg to about 650 mg, about 500 mg to about 650 mg, about 550 mg to about 650 mg, about 600 to about 650 mg, about 100 mg to about 600 mg, about 150 mg to about 600 mg, about 200 mg to about 600 mg, about 250 mg to about 600 mg, about 300 mg to about 600 mg, about 350 mg to about 600 mg, about 400 mg to about 600 mg, about 450 mg to about 600 mg, about 500 mg to about 600 mg, about 550 mg to about 600 mg, about 100 mg to about 550 mg, about 150 mg to about 550 mg, about 200 mg to about 550 mg, about 250 mg to about 550 mg, about 300 mg to about 550 mg, about 350 mg to about 550 mg, about 400 mg to about 550 mg, about 450 mg to about 550 mg, about 500 mg to about 550 mg, about 100 mg to about 500 mg, about 150 mg to about 500 mg, about 200 mg to about 500 mg, about 250 mg to about 500 mg, about 300 mg to about 500 mg, about 350 mg to about 500 mg, about 400 mg to about 500 mg, or about 450 mg to about 500 mg, e.g., a fixed dose of about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, or about 700 mg. Values and ranges intermediate to the foregoing recited values are also intended to be part of this invention.

In one embodiment, the maintenance phase comprises administration of a dose of the RNAi agent to the subject once a month, once every two months, once every three months, once every four months, once every five months, or once every six months. In one particular embodiment, the maintenance dose is administered to the subject once a month.

The maintenance dose or doses can be the same or lower than the initial dose, e.g., one-half of the initial dose. For example, a maintenance dose may be about 25 mg to about 100 mg administered to the subject monthly, for example about 25 mg to about 75 mg, about 25 mg to about 50 mg, or about 50 mg to about 75 mg, e.g., about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. Values and ranges intermediate to the foregoing recited values are also intended to be part of this invention.

Any of these schedules may optionally be repeated for one or more iterations. The number of iterations may depend on the achievement of a desired effect, e.g., the suppression of a PCSK9 gene, and/or the achievement of a therapeutic or prophylactic effect, e.g., reducing serum cholesterol levels or reducing a symptom of hypercholesterolemia. Following treatment, the patient can be monitored for changes in his/her condition. The dosage of the RNAi agent may either be increased in the event the patient does not respond significantly to current dosage levels, or the dose may be decreased if an alleviation of the symptoms of the disease state is observed, if the disease state has been ablated, or if undesired side-effects are observed.

Accordingly, in one aspect, the present invention provides methods of inhibiting the expression of a PCSK9 gene in a subject. The methods include administering to the subject a double-stranded ribonucleic acid (RNAi) agent in a dosing regimen that includes a loading phase followed by a maintenance phase, wherein the loading phase comprises administering a fixed dose of about 200 mg to about 600 mg of the RNAi agent to the subject, and wherein the maintenance phase comprises administering a fixed dose of about 25 mg to about 100 mg of the RNAi agent to the subject about once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby inhibiting the expression of the PCSK9 gene in the subject.

In another aspect, the present invention provides method s of decreasing the level of low density lipoprotein (LDLc) in a subject. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby decreasing the level of LDLc in the subject.

In another aspect, the present invention provides methods of treating a subject having a disorder that would benefit from reduction in PCSK9 expression. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby treating the subject having a disorder that would benefit from reduction in PCSK9 expression.

In yet another aspect, the present invention provides methods of treating a subject having hyperlipidemia. The methods include administering to the subject a double-stranded ribonucleic acid (RNAi) agent in a dosing regimen that includes a loading phase followed by a maintenance phase, wherein the loading phase comprises administering to the subject a fixed dose of about 200 mg to about 600 mg of the RNAi agent, and wherein the maintenance phase comprises administering to the subject a fixed dose of about 25 mg to about 100 mg of the RNAi agent once a month, wherein the double-stranded RNAi agent comprises a sense strand and an antisense strand forming a double stranded region, the antisense strand comprising a region of complementarity which comprises at least 15 contiguous nucleotides differing by no more than 3 nucleotides from nucleotides 3544-3623 of the nucleotide sequence of SEQ ID NO:1, thereby treating the subject having hyperlipidemia.

In one embodiment, the double-stranded ribonucleic acid (RNAi) agent for use in the methods of the present invention comprises a sense strand and an antisense strand forming a double stranded region, wherein the antisense strand comprises the nucleotide sequence 5'-ACAAAAGCAAAACA-GGUCUAGAA-3' (SEQ ID NO: 685) and the sense strand comprises the nucleotide sequence 5'-CUAGACCUGU-TUUGCUUUUGU-3' (SEQ ID NO: 686), wherein substantially all of the nucleotides of the sense strand and substantially all of the nucleotides of the antisense strand are modified nucleotides.

As used herein, a "subject" includes a human or non-human animal, preferably a vertebrate, and more preferably a mammal. A subject may include a transgenic organism. Most preferably, the subject is a human, such as a human suffering from or predisposed to developing a PCSK9-associated disease.

The methods and uses of the invention include administering a composition described herein such that expression of the target PCSK9 gene is decreased, for an extended period of time, such as, for about 80 days, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, or about 180 days, or longer.

Reduction in gene expression can be assessed by any methods known in the art. For example, a reduction in the expression of PCSK9 may be determined by determining the mRNA expression level of PCSK9 using methods routine to one of ordinary skill in the art, e.g., Northern blotting, qRT-PCR, by determining the protein level of PCSK9 using methods routine to one of ordinary skill in the art, such as Western blotting, immunological techniques, and/or by determining a biological activity of PCSK9, such as the effect on one or more serum lipid parameters, such as, for example, total cholesterol levels, high density lipoprotein cholesterol (HDL) levels, non-HDL levels, very low density lipoprotein cholesterol (VLDL) levels, triglyceride levels, Lp(a) levels, and lipoprotein particle size.

Administration of the dsRNA according to the methods and uses of the invention may result in a reduction of the severity, signs, symptoms, and/or markers of such diseases or disorders in a patient with a disorder that would benefit from reduction in PCSK9 expression. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%.

Efficacy of treatment or prevention of disease can be assessed, for example by measuring disease progression, disease remission, symptom severity, serum lipid levels (e.g., LDLc levels), quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of a hyperlipidemia may be assessed, for example, by periodic monitoring of LDLc levels. Comparisons of the later readings with the initial readings provide a physician an indication of whether the treatment is effective. It is well within the ability of one skilled in the art to monitor efficacy of treatment or prevention by measuring any one of such parameters, or any combination of parameters.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Alternatively, the efficacy can be measured by a reduction in the severity of disease as determined by one skilled in the art of diagnosis based on a clinically accepted disease severity grading scale. Any positive change resulting in e.g., lessening of severity of disease measured using the appropriate scale, represents adequate treatment using an iRNA or iRNA formulation as described herein.

In general, the iRNA agent does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control dsRNA, such as a dsRNA that does not target PCSK9.

In another embodiment, administration can be provided when Low Density Lipoprotein cholesterol (LDLc) levels reach or surpass a predetermined minimal level, such as greater than 70 mg/dL, 130 mg/dL, 150 mg/dL, 200 mg/dL, 300 mg/dL, or 400 mg/dL.

The effect of the decreased PCSK9 gene preferably results in a decrease in LDLc (low density lipoprotein cholesterol) levels in the blood, and more particularly in the serum, of the mammal. In some embodiments, LDLc levels are decreased by at least 10%, 15%, 20%, 25%, 30%, 40%, 50%, 60%, 70%, 80%, 90% or more, as compared to pretreatment levels.

In some embodiments of the methods of the invention, PCSK9 expression is decreased for an extended duration, e.g., at least one week, two weeks, three weeks, or four weeks or longer. For example, in certain instances, expression of the PCSK9 gene is suppressed by at least about 5%, 10%, 15%, 20%, 25%, 30%, 35%, 40%, 45%, or 50% by administration of an iRNA agent described herein. In some embodiments, the PCSK9 gene is suppressed by at least about 60%, 70%, or 80% by administration of the iRNA agent. In some embodiments, the PCSK9 gene is suppressed by at least about 85%, 90%, or 95% by administration of the double-stranded oligonucleotide.

The RNAi agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the agents are administered subcutaneously.

In some embodiments, the administration is via a depot injection. A depot injection may release the RNAi agent in a consistent way over a prolonged time period. Thus, a depot injection may reduce the frequency of dosing needed to obtain a desired effect, e.g., a desired inhibition of PCSK9, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the iRNA can reduce PCSK9 levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the iRNA, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on PCSK9 expression, a composition according to the invention or a pharmaceutical composition prepared therefrom can enhance the quality of life. An iRNA of the invention may be administered in "naked" form, or as a "free iRNA." A naked iRNA is administered in the absence of a pharmaceutical composition. The naked iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

The invention further provides methods and uses for the use of an iRNA or a pharmaceutical composition thereof, e.g., for treating a subject that would benefit from reduction and/or inhibition of PCSK9 expression, e.g., a subject having hyperlipidemia, e.g., hypercholesterolemia, in combination with other pharmaceuticals and/or other therapeutic methods, e.g., with known pharmaceuticals and/or known therapeutic methods, such as, for example, those which are currently employed for treating these disorders. The siRNA and an additional therapeutic agent can be administered in combination in the same composition, e.g., parenterally, or the additional therapeutic agent can be administered as part of a separate composition or by another method described herein.

Examples of additional therapeutic agents include those known to treat an agent known to treat a lipid disorders, such as hypercholesterolemia, atherosclerosis or dyslipidemia. For example, a siRNA featured in the invention can be administered with, e.g., an HMG-CoA reductase inhibitor (e.g., a statin), a fibrate, a bile acid sequestrant, niacin, an antiplatelet agent, an angiotensin converting enzyme inhibitor, an angiotensin II receptor antagonist (e.g., losartan potassium, such as Merck & Co.'s Cozaar®), an acylCoA cholesterol acetyltransferase (ACAT) inhibitor, a cholesterol absorption inhibitor, a cholesterol ester transfer protein (CETP) inhibitor, a microsomal triglyceride transfer protein (MTTP) inhibitor, a cholesterol modulator, a bile acid modulator, a peroxisome proliferation activated receptor (PPAR) agonist, a gene-based therapy, a composite vascular protectant (e.g., AGI-1067, from Atherogenics), a glycoprotein IIb/IIIa inhibitor, aspirin or an aspirin-like compound, an IBAT inhibitor (e.g., S-8921, from Shionogi), a squalene synthase inhibitor, or a monocyte chemoattractant protein (MCP)-I inhibitor. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis). Exemplary fibrates include, e.g., bezafibrate (e.g., Roche's Befizal®/Cedur®/Bezalip®, Kissei's Bezatol), clofibrate (e.g., Wyeth's Atromid-S®), fenofibrate (e.g., Fournier's Lipidil/Lipantil, Abbott's Tricor®, Takeda's Lipantil, generics), gemfibrozil (e.g., Pfizer's Lopid/Lipur) and ciprofibrate (Sanofi-Synthelabo's Modalim®). Exemplary bile acid sequestrants include, e.g., cholestyramine (Bristol-Myers Squibb's Questran® and Questran Light™), colestipol (e.g., Pharmacia's Colestid), and colesevelam (Genzyme/Sankyo's WelChol™). Exemplary niacin therapies include, e.g., immediate release formulations, such as Aventis' Nicobid, Upsher-Smith's Niacor, Aventis' Nicolar, and Sanwakagaku's Perycit. Niacin extended release formulations include, e.g., Kos Pharmaceuticals' Niaspan and Upsher-Smith's SIo-Niacin. Exemplary antiplatelet agents include, e.g., aspirin (e.g., Bayer's aspirin), clopidogrel (Sanofi-Synthelabo/Bristol-Myers Squibb's Plavix), and ticlopidine (e.g., Sanofi-Synthelabo's Ticlid and Daiichi's Panaldine). Other aspirin-like compounds useful in combination with a dsRNA targeting PCSK9 include, e.g., Asacard (slow-release aspirin, by Pharmacia) and Pamicogrel (Kanebo/Angelini Ricerche/CEPA). Exemplary angiotensin-converting enzyme inhibitors include, e.g., ramipril (e.g., Aventis' Altace) and enalapril (e.g., Merck & Co.'s Vasotec). Exemplary acyl CoA cholesterol acetyltransferase (ACAT) inhibitors include, e.g., avasimibe (Pfizer), eflucimibe (BioMsrieux Pierre Fabre/Eli Lilly), CS-505 (Sankyo and Kyoto), and SMP-797 (Sumito). Exemplary cholesterol absorption inhibitors include, e.g., ezetimibe (Merck/Schering-Plough Pharmaceuticals Zetia®) and Pamaqueside (Pfizer). Exemplary CETP inhibitors include, e.g., Torcetrapib (also called CP-529414, Pfizer), JTT-705 (Japan Tobacco), and CETi-I (Avant Immunotherapeutics). Exemplary microsomal triglyceride transfer protein (MTTP) inhibitors include, e.g., implitapide (Bayer), R-103757 (Janssen), and CP-346086 (Pfizer). Other exemplary cholesterol modulators include, e.g., NO-1886 (Otsuka/TAP Pharmaceutical), CI-1027 (Pfizer), and WAY-135433 (Wyeth-Ayerst).

Exemplary bile acid modulators include, e.g., HBS-107 (Hisamitsu/Banyu), Btg-511 (British Technology Group), BARI-1453 (Aventis), S-8921 (Shionogi), SD-5613 (Pfizer), and AZD-7806 (AstraZeneca). Exemplary peroxisome proliferation activated receptor (PPAR) agonists include, e.g., tesaglitazar (AZ-242) (AstraZeneca), Netoglitazone (MCC-555) (Mitsubishi/Johnson & Johnson), GW-409544 (Ligand Pharniaceuticals/GlaxoSmithKline), GW-501516 (Ligand Pharmaceuticals/GlaxoSmithKline), LY-929 (Ligand Pharmaceuticals and Eli Lilly), LY-465608 (Ligand Pharmaceuticals and Eli Lilly), LY-518674 (Ligand Pharmaceuticals and Eli Lilly), and MK-767 (Merck and Kyorin). Exemplary gene-based therapies include, e.g., AdGWEGF 121.10 (GenVec), ApoAl (UCB Pharma/Groupe Fournier), EG-004 (Trinam) (Ark Therapeutics), and ATP-binding cassette transporter-A1 (ABCA1) (CV Therapeutics/Incyte, Aventis, Xenon). Exemplary Glycoprotein IIb/IIIa inhibitors include, e.g., roxifiban (also called DMP754, Bristol-Myers Squibb), Gantofiban (Merck KGaA/Yamanouchi), and Cromafiban (Millennium Pharmaceuticals). Exemplary squalene synthase inhibitors include, e.g., BMS-1884941 (Bristol-Myers Squibb), CP-210172 (Pfizer), CP-295697 (Pfizer), CP-294838 (Pfizer), and TAK-475 (Takeda). An exemplary MCP-I inhibitor is, e.g., RS-504393 (Roche Bioscience). The anti-atherosclerotic agent BO-653 (Chugai Pharmaceuticals), and the nicotinic acid derivative Nyclin (Yamanouchi Pharmaceuticals) are also appropriate for administering in combination with a dsRNA featured in the invention. Exemplary combination therapies suitable for administration with a dsRNA targeting PCSK9 include, e.g., advicor (Niacin/lovastatin from Kos Pharmaceuticals), amlodipine/atorvastatin (Pfizer), and ezetimibe/simvastatin (e.g., Vytorin® 10/10, 10/20, 10/40, and 10/80 tablets by Merck/Schering-Plough Pharmaceuticals). Agents for treating hypercholesterolemia, and suitable for administration in combination with a dsRNA targeting PCSK9 include, e.g., lovastatin, niacin Altoprev® Extended-Release Tablets (Andrx Labs), lovastatin Caduet® Tablets (Pfizer), amlodipine besylate, atorvastatin calcium Crestor® Tablets (AstraZeneca), rosuvastatin calcium Lescol® Capsules (Novartis), fluvastatin sodium Lescol® (Reliant, Novartis), fluvastatin sodium Lipitor® Tablets (Parke-Davis), atorvastatin calcium Lofibra® Capsules (Gate), Niaspan Extended-Release Tablets (Kos), niacin Pravachol Tablets (Bristol-Myers Squibb), pravastatin sodium TriCor® Tablets (Abbott), fenofibrate Vytorin® 10/10 Tablets (Merck/Schering-Plough Pharmaceuticals), ezetimibe, simvastatin WelChol™ Tablets (Sankyo), colesevelam hydrochloride Zetia® Tablets (Schering), ezetimibe Zetia® Tablets (Merck/Schering-Plough Pharmaceuticals), and ezetimibe Zocor® Tablets (Merck).

In one embodiment, an iRNA agent is administered in combination with an ezetimibe/simvastatin combination (e.g., Vytorin® (Merck/Schering-Plough Pharmaceuticals)).

In another embodiment, an iRNA agent is administered in combination with an anti-PCSK9 antibody. Exemplary anti-PCSK9 antibodies for use in the combination therapies of the invention include, for example, alirocumab (Praluent), evolocumab (Repatha), bococizumab (PF-04950615, RN316, RN-316, L1L3; Pfizer, Rinat), lodelcizumab (LFU720, pJG04; Novartis), ralpancizumab (RN317, PF-05335810; Pfizer, Rinat), RG7652 (MPSK3169A, YW508.20.33b; Genentech), LY3015014 (Lilly), LPD1462 (h1F11; Schering-Plough), AX1(AX189, 1B20, 1D05; Merck & Co), ALD306 (Alder); mAb1 (Boehringer), and Ig1-PA4 (Nanjing Normal U.).

In one embodiment, the iRNA agent is administered to the patient, and then the additional therapeutic agent is administered to the patient (or vice versa). In another embodiment, the iRNA agent and the additional therapeutic agent are administered at the same time.

In another aspect, the invention features, a method of instructing an end user, e.g., a caregiver or a subject, on how to administer an iRNA agent described herein. The method includes, optionally, providing the end user with one or more doses of the iRNA agent, and instructing the end user to administer the iRNA agent on a regimen described herein, thereby instructing the end user.

In one aspect, the invention provides a method of treating a patient by selecting a patient on the basis that the patient is in need of LDL lowering, LDL lowering without lowering of HDL, ApoB lowering, or total cholesterol lowering. The method includes administering to the patient a siRNA in an amount sufficient to lower the patient's LDL levels or ApoB levels, e.g., without substantially lowering HDL levels.

Genetic predisposition plays a role in the development of target gene associated diseases, e.g., hyperlipidemia. Therefore, a patient in need of a siRNA can be identified by taking a family history, or, for example, screening for one or more genetic markers or variants. Examples of genes involved in hyperlipidemia include but are not limited to, e.g., LDL receptor (LDLR), the apoliproteins (ApoA1, ApoB, ApoE, and the like), Cholesteryl ester transfer protein (CETP), Lipoprotein lipase (LPL), hepatic lipase (LIPC), Endothelial lipase (EL), Lecithinxholesteryl acyltransferase (LCAT).

A healthcare provider, such as a doctor, nurse, or family member, can take a family history before prescribing or administering an iRNA agent of the invention. In addition, a test may be performed to determine a geneotype or phenotype. For example, a DNA test may be performed on a sample from the patient, e.g., a blood sample, to identify the PCSK9 genotype and/or phenotype before a PCSK9 dsRNA is administered to the patient. In another embodiment, a test is performed to identify a related genotype and/or phenotype, e.g., a LDLR genotype. Example of genetic variants with the LDLR gene can be found in the art, e.g., in the following publications which are incorporated by reference: Costanza et al (2005) *Am J Epidemiol.* 15; 161 (8):714-24; Yamada et al. (2008) *J Med Genet.* January; 45(1):22-8, Epub 2007 Aug. 31; and Boes et al (2009) *Exp. Gerontol* 44: 136-160, Epub 2008 Nov. 17.

The present invention further provides methods of inhibiting expression of a Proprotein Convertase Subtilisin Kexin 9 (PCSK9) in a cell, such as a cell within a subject, e.g., a human subject.

Accordingly, the present invention provides methods of inhibiting expression of a PCSK9 gene in a cell. The methods include contacting a cell with an RNAi agent, e.g., a double stranded RNAi agent, in an amount effective to inhibit expression of the PCSK9 gene in the cell, thereby inhibiting expression of the PCSK9 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a PCSK9" is intended to refer to inhibition of expression of any PCSK9 gene (such as, e.g., a mouse PCSK9 gene, a rat PCSK9 gene, a monkey PCSK9 gene, or a human PCSK9 gene) as well as variants or mutants of a PCSK9 gene. Thus, the PCSK9 gene may be a wild-type PCSK9 gene, a mutant PCSK9 gene, or a transgenic PCSK9 gene in the context of a genetically manipulated cell, group of cells, or organism.

"Inhibiting expression of a PCSK9 gene" includes any level of inhibition of a PCSK9 gene, e.g., at least partial suppression of the expression of a PCSK9 gene. The expression of the PCSK9 gene may be assessed based on the level, or the change in the level, of any variable associated with PCSK9 gene expression, e.g., PCSK9 mRNA level, PCSK9 protein level, or lipid levels. This level may be assessed in an individual cell or in a group of cells, including, for example, a sample derived from a subject.

Inhibition may be assessed by a decrease in an absolute or relative level of one or more variables that are associated with PCSK9 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a PCSK9 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a PCSK9 gene may be manifested by a reduction of the amount of mRNA expressed by a first cell or group of cells (such cells may be present, for example, in a sample derived from a subject) in which a PCSK9 gene is transcribed and which has or have been treated (e.g., by contacting the cell or cells with an RNAi agent of the invention, or by administering an RNAi agent of the invention to a subject in which the cells are or were present) such that the expression of a PCSK9 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \cdot 100\%$$

Alternatively, inhibition of the expression of a PCSK9 gene may be assessed in terms of a reduction of a parameter that is functionally linked to PCSK9 gene expression, e.g., PCSK9 protein expression, such as lipid levels, cholesterol levels, e.g., LDLc levels. PCSK9 gene silencing may be determined in any cell expressing PCSK9, either constitutively or by genomic engineering, and by any assay known in the art. The liver is the major site of PCSK9 expression. Other significant sites of expression include the pancreas, kidney, and intestines.

Inhibition of the expression of a PCSK9 protein may be manifested by a reduction in the level of the PCSK9 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a PCSK9 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of PCSK9 mRNA that is expressed by a cell or group of cells may be determined using any method known in the art for assessing mRNA expression. In one embodiment, the level of expression of PCSK9 in a sample is determined by detecting a transcribed polynucleotide, or portion thereof, e.g., mRNA of the PCSK9 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of PCSK9 is determined using a nucleic acid probe. The term "probe", as used herein, refers to any molecule that is capable of selectively binding to a specific PCSK9. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to PCSK9 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of PCSK9 mRNA.

An alternative method for determining the level of expression of PCSK9 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of PCSK9 is determined by quantitative fluorogenic RT-PCR (i.e., the TaqMan™ System).

The expression levels of PCSK9 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of PCSK9 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of PCSK9 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of PCSK9 may be assessed using measurements of the level or change in the level of PCSK9 mRNA or PCSK9 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

III. iRNAs for Use in the Methods of the Invention

Described herein are methods for the use of double-stranded RNAi agents which inhibit the expression of a PCSK9 gene in a cell, such as a cell within a subject, e.g., a mammal, such as a human having a PCSK9-associated disorder, e.g., a hyperlipidemia, e.g., hypercholesterolemia.

Accordingly, the invention provides double-stranded RNAi agents capable of inhibiting the expression of a target gene (i.e., a PCSK9 gene) in vivo for use in the claimed methods.

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain aspects of the invention, substantially all of the nucleotides of an iRNA of the invention are modified. For example substantially all of the nucleotides of the sense strand are modified nucleotides, and/or substantially all of the nucleotides of the antisense strand are modified nucleotides and/or substantially all of the nucleotides of both the sense strand and the antisense strand are modified nucleotides. In other embodiments of the invention, all of the nucleotides of an iRNA of the invention are modified. For example all of the nucleotides of the sense strand are modified nucleotides, and/or all of the nucleotides of the antisense strand are modified nucleotides and/or all of the nucleotides of both the sense strand and the antisense strand are modified nucleotides. iIRNAs of the invention in which "substantially all of the nucleotides are modified" are largely but not wholly modified and can include not more than 5, 4, 3, 2, or 1 unmodified nucleotides.

The dsRNA includes an antisense strand having a region of complementarity which is complementary to at least a part of an mRNA formed in the expression of a PCSK9 gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the PCSK9 gene, the iRNA inhibits the expression of the PCSK9 gene (e.g., a human PCSK9 gene) by at least about 10% as assayed by, for example, a PCR or branched DNA (bDNA)-based method, or by a protein-based method, such as by immunofluorescence analysis, using, for example, Western Blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of a PCSK9 gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is about 15 to about 20 nucleotides in length, or between about 25 and about 30 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

In certain embodiments, a dsRNA agent of the invention may include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of a PCSK9 gene. These dsRNA agents with the longer length antisense strands preferably include a second RNA strand (the sense strand) of 20-60 nucleotides in length wherein the sense and antisense strands form a duplex of 18-30 contiguous nucleotides.

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs.

Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target PCSK9 expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. In certain embodiments, longer, extended overhangs are possible.

A dsRNA can be synthesized by standard methods known in the art as further discussed below, e.g., by use of an automated DNA synthesizer, such as are commercially available from, for example, Biosearch, Applied Biosystems, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in Table 1, and the corresponding antisense strand of the sense strand is selected from the group of sequences of Table 1. In this aspect, one of the two sequences is complementary to the other of the two sequences, with one of the sequences being substantially complementary to a sequence of an mRNA generated in the expression of a PCSK9 gene. As such, in this aspect, a dsRNA will include two oligonucleotides, where one oligonucleotide is described as the sense strand in Table 1, and the second oligonucleotide is described as the corresponding antisense strand of the sense strand in Table 1. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Table 1 are described as modified and/or conjugated sequences, the RNA of the iRNA of the invention e.g., a dsRNA of the invention, may comprise any one of the sequences set forth in Table 1 that is un-modified, un-conjugated, and/or modified and/or conjugated differently than described therein.

The skilled person is well aware that dsRNAs having a duplex structure of between about 20 and 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in Table 1, dsRNAs described herein can include at least one strand of a length of minimally 21 nucleotides. It can be reasonably expected that shorter duplexes having one of the sequences of any one of Table 1 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3, 4, 5, 6, 18, 19, 20, 21, and 23, and differing in their ability to inhibit the expression of a PCSK9 gene by not more than about 5, 10, 15, 20, 25, or 30% inhibition from a dsRNA comprising the full sequence, are contemplated to be within the scope of the present invention.

In addition, the RNAs provided in Table 1 identify a site(s) in a PCSK9 transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in Table 1 coupled to additional nucleotide sequences taken from the region contiguous to the selected sequence in a PCSK9 gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in a Table 1 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in Table 1, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of a PCSK9 gene, generally does not contain any mismatch within the central 13 nucleotides. The methods described herein or methods known in the art can be used to determine whether an iRNA containing a mismatch to a target sequence is effective in inhibiting the expression of a PCSK9 gene. Consideration of the efficacy of iRNAs with mismatches in inhibiting expression of a PCSK9 gene is important, especially if the particular region of complementarity in a PCSK9 gene is known to have polymorphic sequence variation within the population.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones;

alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$NH$_2$, O($CH_2$)$_n$$CH_3$, O($CH_2$)$_n$ONH$_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, SO$_2$$CH_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2$$CH_2$O$CH_3$, also known as 2'-O-(2-methoxyethyl) or 2'-MOE) (Martin et al., *Helv. Chin. Acta,* 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications include 2'-methoxy (2'-O$CH_3$), 2'-aminopropoxy (2'-O$CH_2$$CH_2$$CH_2$NH$_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

The RNA of an iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT)$_r$, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include the RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA); 4'-(CH2)-S-2'; 4'-(CH2)2-O-2' (ENA); 4'-CH(CH3)-O-2' (also referred to as "constrained ethyl" or "cEt") and 4'-CH(CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.,* 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3''-phosphate, inverted base dT(idT) and others. Disclosure of this modification can be found in PCT Publication No. WO 2011/005861.

A. Modified iRNAs Comprising Motifs

In certain aspects of the invention, the double-stranded RNAi agents of the invention include agents with chemical modifications as disclosed, for example, in U.S. Patent Publication No. 2014/0315835 and PCT Publication No. WO 2013/075035, the entire contents of each of which are incorporated herein by reference, the entire contents of each of which are incorporated herein by reference. As shown herein and in U.S. Patent Publication No. 2014/0315835 and PCT Publication No. WO 2013/075035, a superior result may be obtained by introducing one or more motifs of three identical modifications on three consecutive nucleotides into a sense strand and/or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are completely modified to have one or more motifs of three identical modifications on three consecutive nucleotides at or near the cleavage site of at least one strand of an RNAi agent, the gene silencing activity of the RNAi agent was superiorly enhanced.

Accordingly, the invention provides double-stranded RNAi agents capable of inhibiting the expression of a target gene (i.e., a PCSK9 gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence. In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisense strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-stranded RNAi agent comprises 6-8 phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5'end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

(I)
5' $n_p$-$N_a$-(X X X)$_i$-$N_b$-Y Y Y -$N_b$-(Z Z Z)$_j$-$N_a$-$n_q$ 3' wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each $n_p$ and $n_q$ independently represent an overhang nucleotide;
wherein Nb and Y do not have the same modification; and XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the 1st nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

(Ib)
5' $n_p$-$N_a$-YYY-$N_b$-ZZZ-$N_a$-$n_q$ 3';

-continued (Ic)
5' $n_p$-$N_a$-XXX-$N_b$-YYY-$N_a$-$n_q$ 3';
or (Id)
5' $n_p$-$N_a$-XXX-$N_b$-YYY-$N_b$-ZZZ-$N_a$-$n_q$ 3'.

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.
Each of X, Y and Z may be the same or different from each other.
In other embodiments, i is 0 and j is 0, and the sense strand may be represented by the formula:

(Ia)
5' $n_p$-$N_a$-YYY-$N_a$-$n_q$ 3'.

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

(II)
5' $n_{q'}$-$N_a'$-(Z'Z'Z')$_k$-$N_b'$-Y'Y'Y'-$N_b'$-(X'X'X')$_l$-$N'_a$-$n_{p'}$ 3' wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_{p'}$ and $n_{q'}$ independently represent an overhang nucleotide;
wherein $N_b'$ and Y' do not have the same modification;
and X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

(IIb)
5' $n_{q'}$-$N_a'$-Z'Z'Z'-$N_b'$-Y'Y'Y'-$N_a'$-$n_{p'}$ 3';

(IIc)
5' $n_{q'}$-$N_a'$-Y'Y'Y'-$N_b'$-X'X'X'-$N_a'$-$n_{p'}$ 3';
or (IId)
5' $n_{q'}$-$N_a'$-Z'Z'Z'-$N_b'$-Y'Y'Y'-$N_b'$-X'X'X'-$N_a'$-$n_{p'}$ 3'.

When the antisense strand is represented by formula (IIb), $N_b'$: represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.
In other embodiments, k is 0 and l is 0 and the antisense strand may be represented by the formula:

(Ia)
5' $n_{p'}$-$N_a'$-Y'Y'Y'-$N_a'$-$n_{q'}$ 3'.

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1st nucleotide from the 5'-end, or optionally, the count starting at the 1st paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification. The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

```
(III)
sense:
5'  n_p-N_a-(X X X)_i-N_b-Y Y Y-N_b-(Z Z Z)_j-N_a-n_q  3' antisense:
3'  n_p'-N_a'-(X'X'X')_k-N_b'-Y'Y'Y'-N_b'-(Z'Z'Z')_l-N_a'-n_q  5'
``` wherein:
i, j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, $n_p$, $n_q'$, and $n_q$, each of which may or may not be present, independently represents an overhang nucleotide; and
XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

```
(IIIa)
5'  n_p-N_a-Y Y Y-N_a-n_q  3'

3'  n_p'-N_a'-Y'Y'Y'-N_a'n_q'  5'

(IIIb)
5'  n_p-N_a-Y Y Y-N_b-Z Z Z-N_a-n_q  3'

3'  n_p'-N_a'-Y'Y'Y'-N_b'-Z'Z'Z'-N_a'n_q'  5'

(IIIc)
5'  n_p-N_a-X X X-N_b-Y Y Y-N_a-n_q  3'

3'  n_p'-N_a'-X'X'X'-N_b'-Y'Y'Y'-N_a'-n_q'  5'

(IIId)
5'  n_p-N_a-X X X-N_b-Y Y Y-N_b-Z Z Z-N_a-n_q  3'

3'  n_p'-N_a'-X'X'X'-N_b'-Y'Y'Y'-N_b'-Z'Z'Z'-N_a-n_q'  5'
```

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858, 769, WO2010/141511, WO2007/117686, WO2009/014887 and WO2011/031520 the entire contents of each of which are hereby incorporated herein by reference.

As described in more detail below, the RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and and decalin; preferably, the acyclic group is selected from serinol backbone or diethanolamine backbone.

In certain specific embodiments, the RNAi agent for use in the methods of the invention is an agent selected from the group of agents listed in any one of Tables 3, 4, 5, 6, 18, 19, 20, 21, and 23. These agents may further comprise a ligand.

IV. iRNAs Conjugated to Ligands

Another modification of the RNA of an iRNA suitable for use in the methods of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acid. Sci. USA,* 1989, 86: 6553-6556), cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, monovalent or multivalent galactose, N-acetyl-galactosamine, N-acetyl-gulucoseamine multivalent mannose, multivalent fucose, glycosylated polyaminoacids, transferrin, bisphosphonate, polyglutamate, polyaspartate, a lipid, cholesterol, a steroid, bile acid, folate, vitamin B12, vitamin A, biotin, or an RGD peptide or RGD peptide mimetic. In certain embodiments, ligands include monovalent or multivalent galactose. In certain embodiments, ligands include cholesterol.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridineimidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand. In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 3). An RFGF analogue (e.g., amino acid sequence AALLPVL-LAAP (SEQ ID NO: 4) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 5) and the *Drosophila* Antennapedia protein (RQIKIWFQNRRMK-WKK (SEQ ID NO: 6) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, a α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate for use in the compositions and methods of the invention is a monosaccharide. In another embodiment, a carbohydrate conjugate for use in the compositions and methods of the invention is selected from the group consisting of:

Formula II
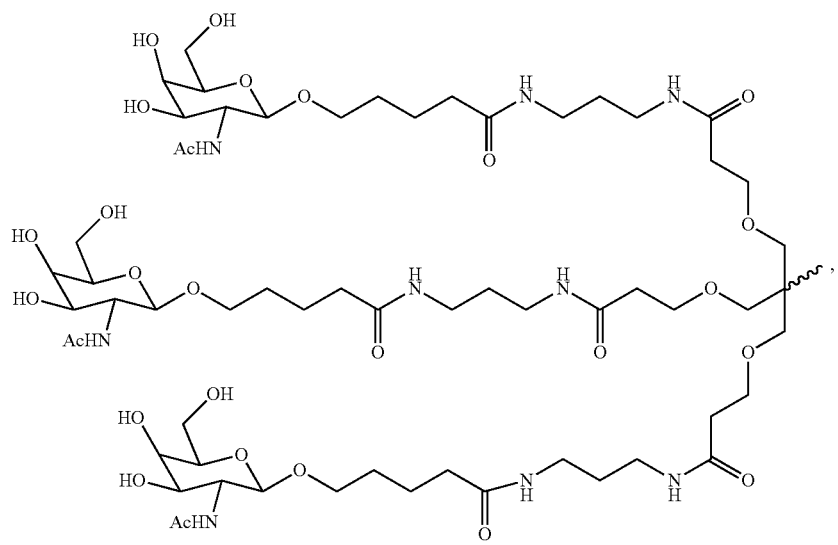
Formula III
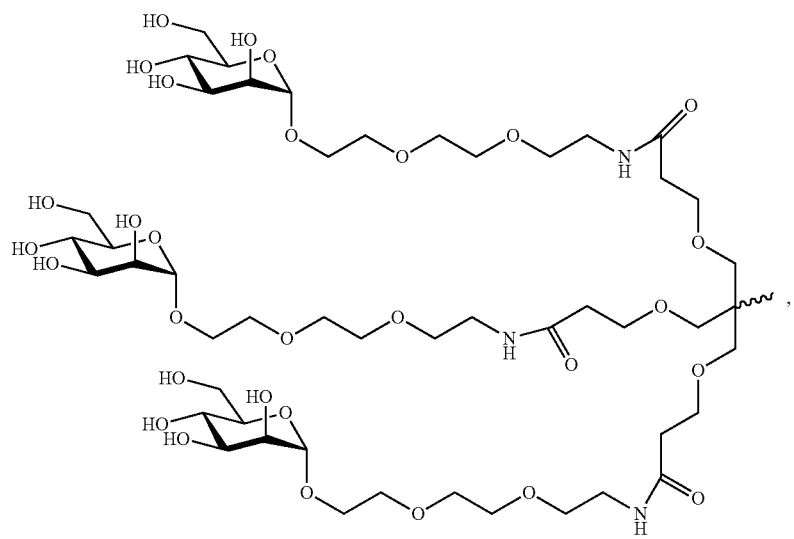
Formula IV
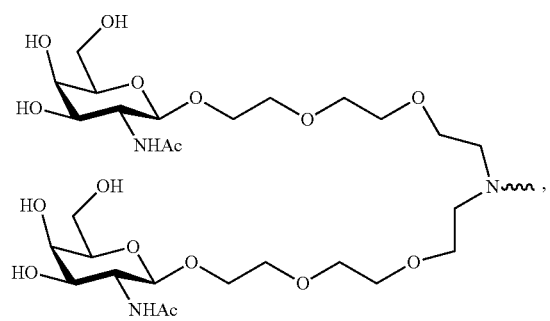
Formula V
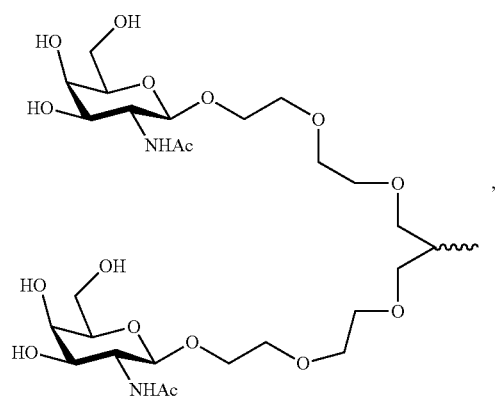

Formula VI
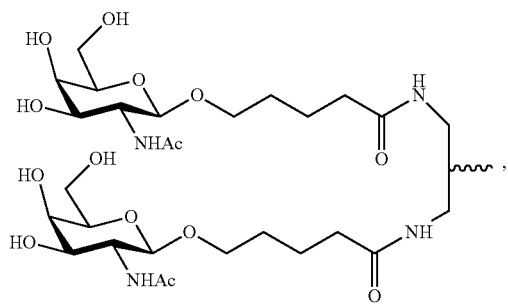
Formula VII
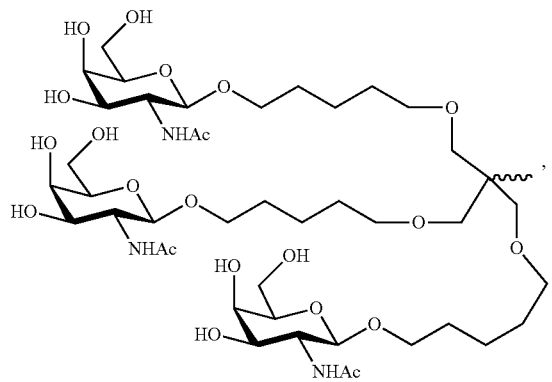
Formula VIII
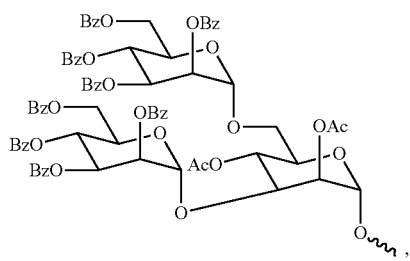
Formula IX
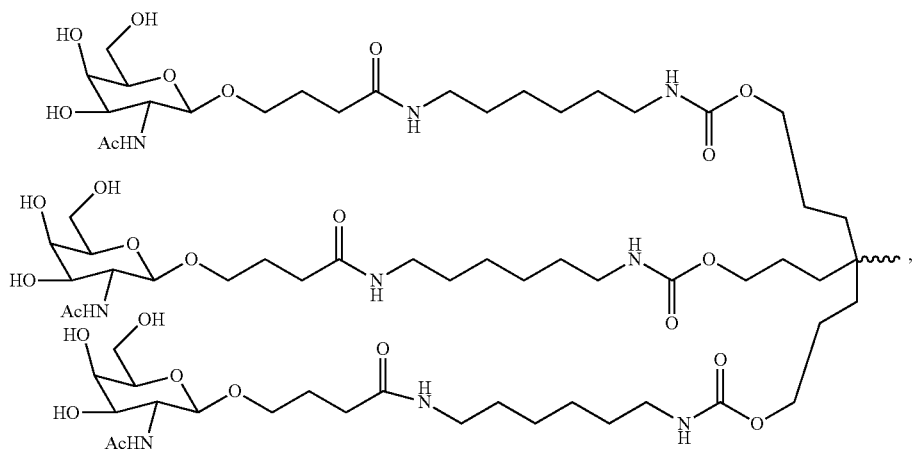
Formula X
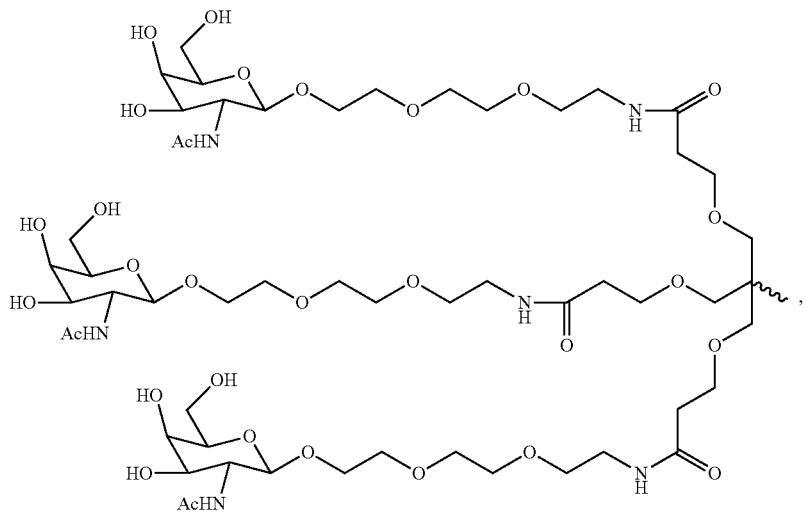

-continued
Formula XI
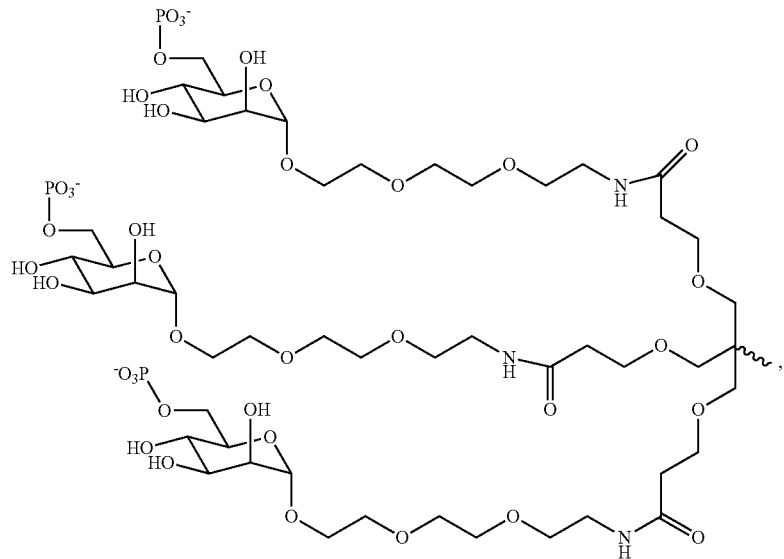
Formula XII
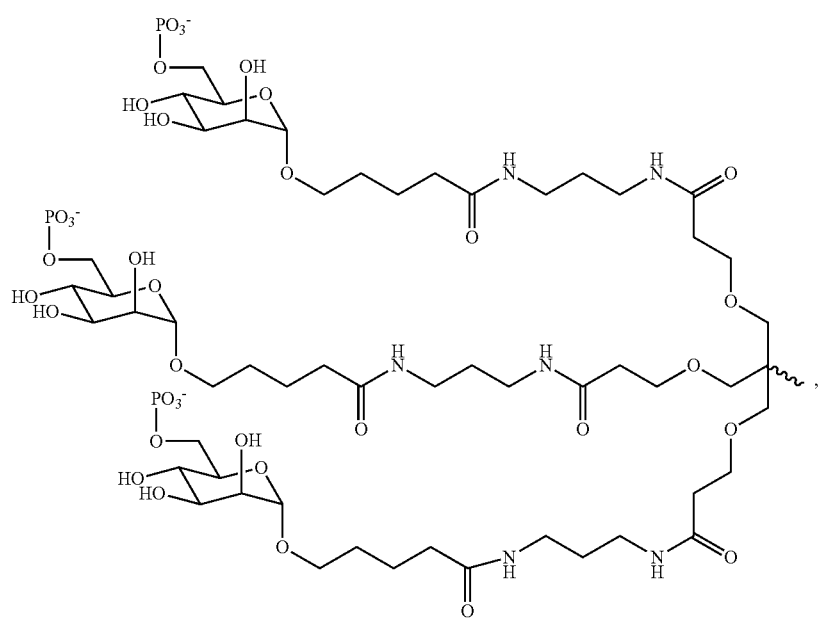
Formula XIII
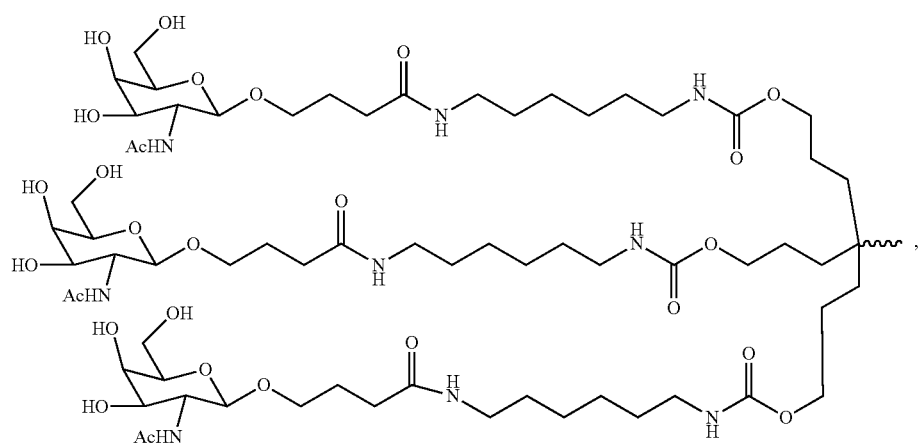

-continued
Formula XIV
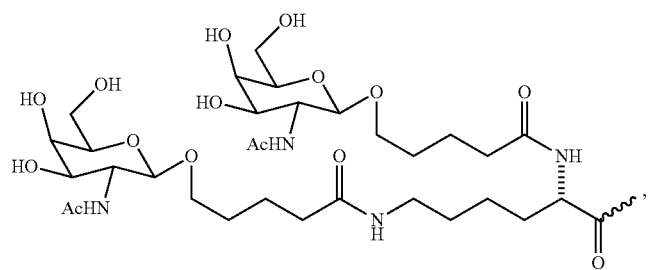
Formula XV
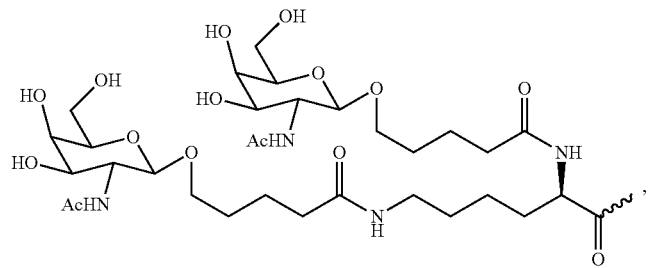
Formula XVI
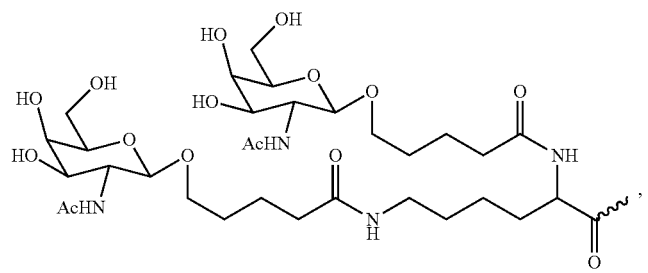
Formula XVII
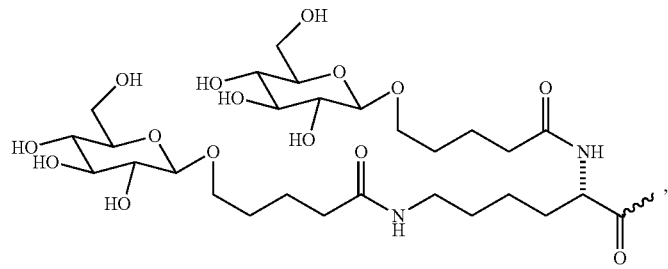
Formula XVIII
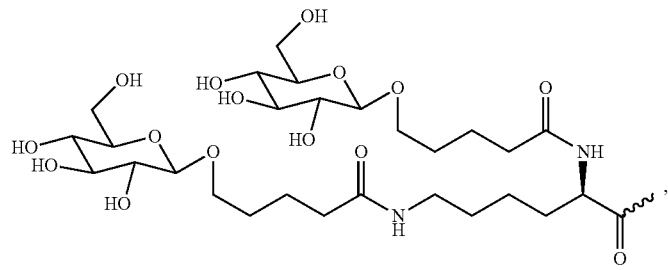
Formula XIX
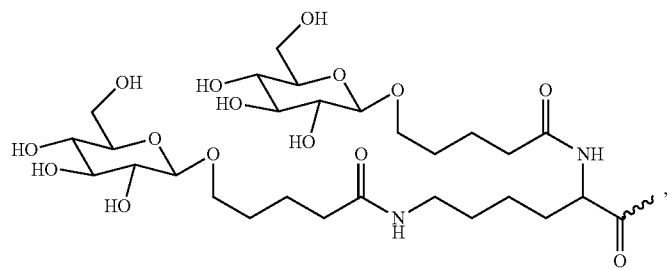

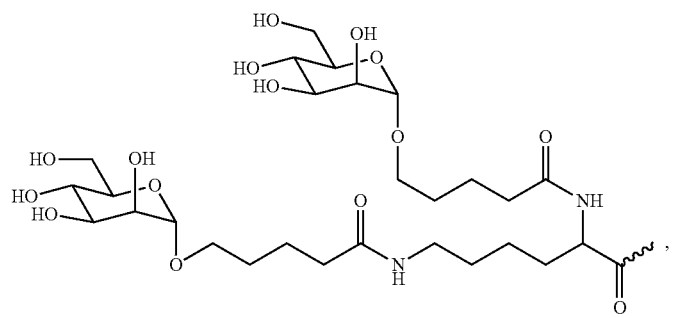
Formula XX
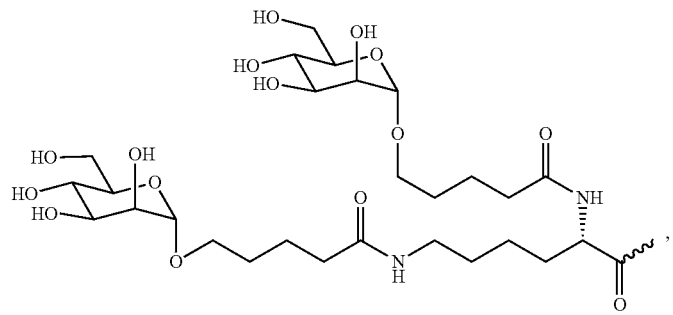
Formula XXI
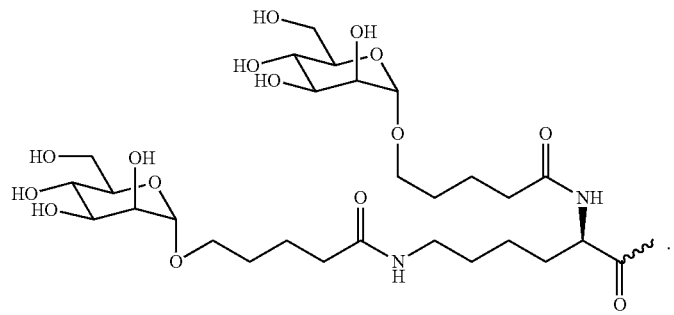
Formula XXII
In one embodiment, the monosaccharide is an N-acetyl-galactosamine, such as
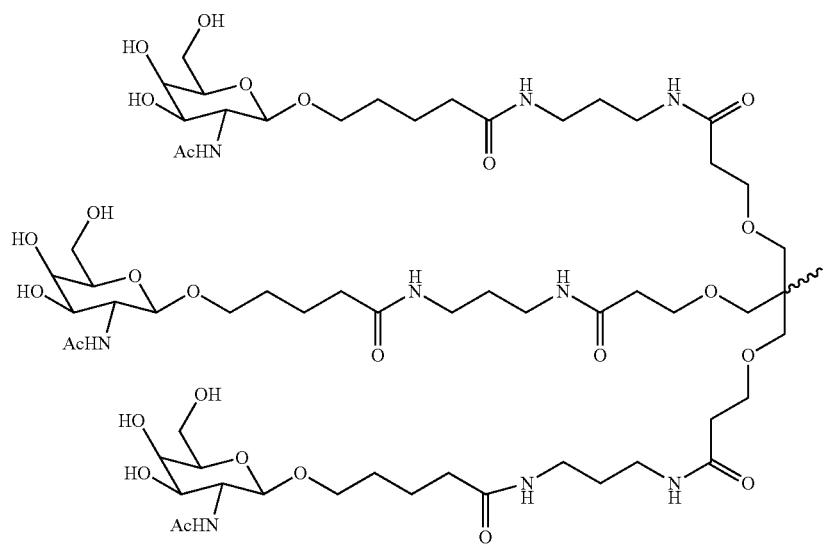
Formula II Another representative carbohydrate conjugate for use in the embodiments described herein includes, but is not limited to,

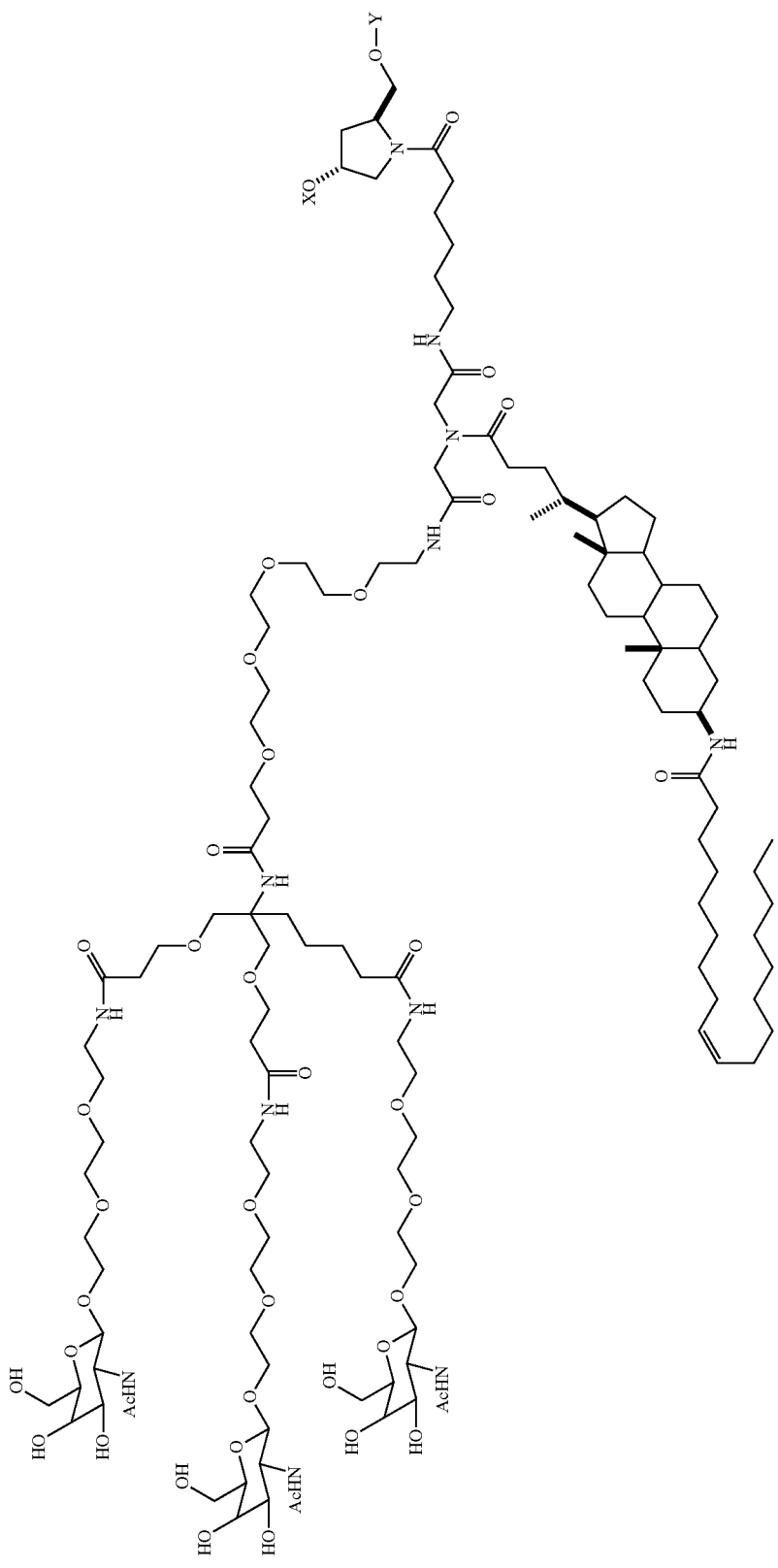

(Formula XXIII), when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker. The hairpin loop may also be formed by an extended overhang in one strand of the duplex.

In some embodiments, the carbohydrate conjugate further comprises one or more additional ligands as described above, such as, but not limited to, a PK modulator and/or a cell permeation peptide.

Additional carbohydrate conjugates suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NRB, C(O), C(O)NH, SO, SO$_2$, SO$_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), SO$_2$, N(8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)
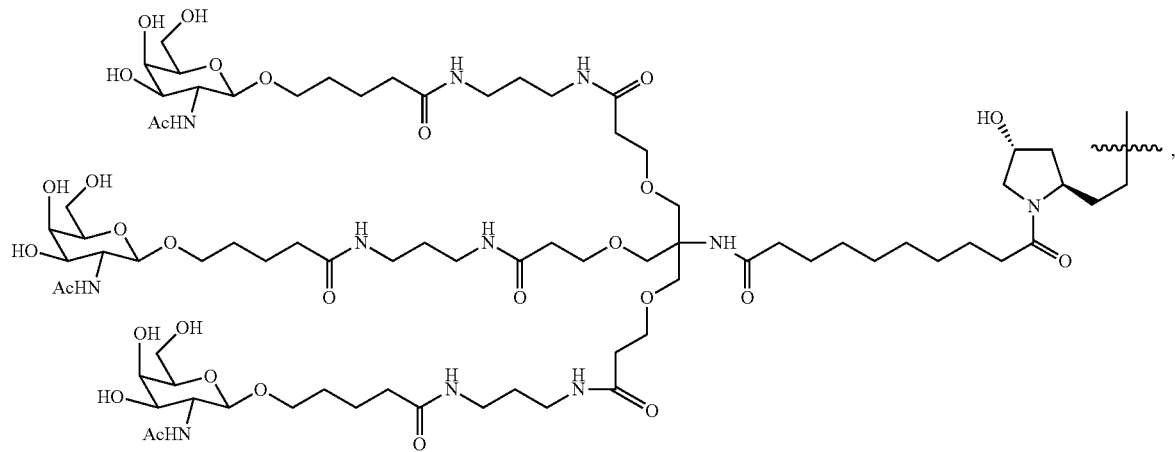
(Formula XXV)
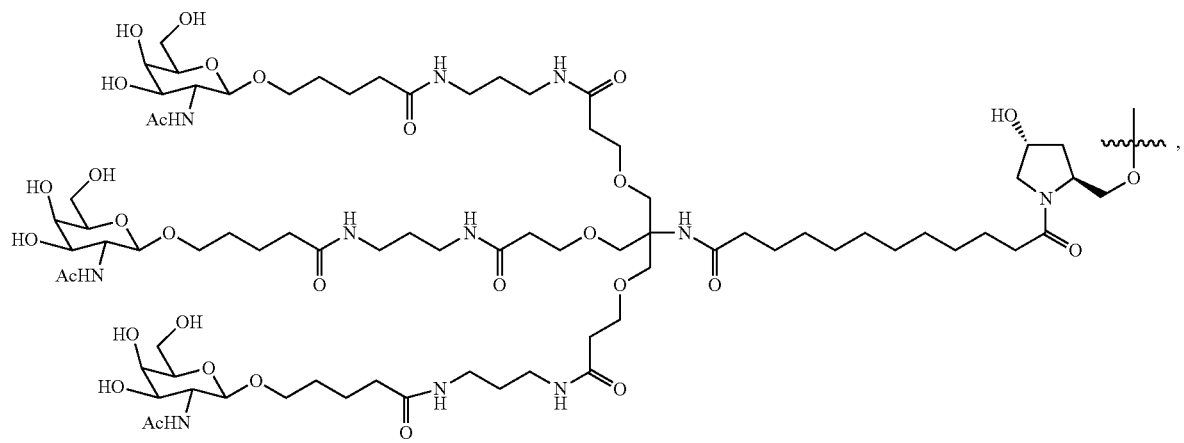
(Formula XXVI)
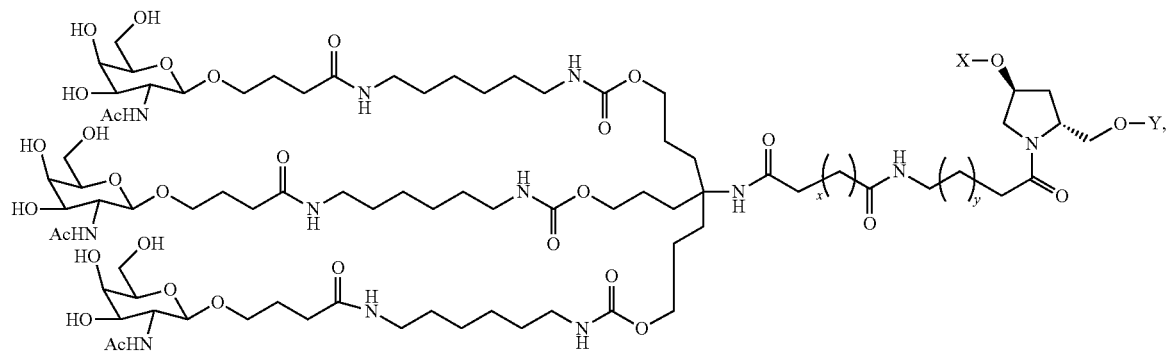
x = 1-30
y = 1-15

-continued
(Formula XXVII)
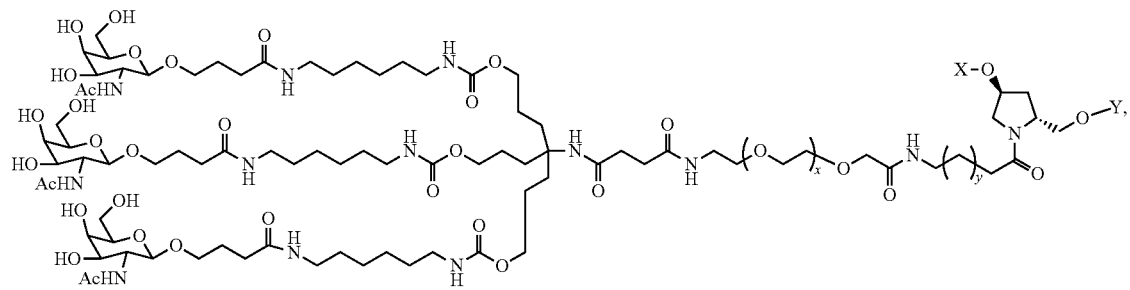
x = 1-30
y = 1-15
(Formula XXVIII)
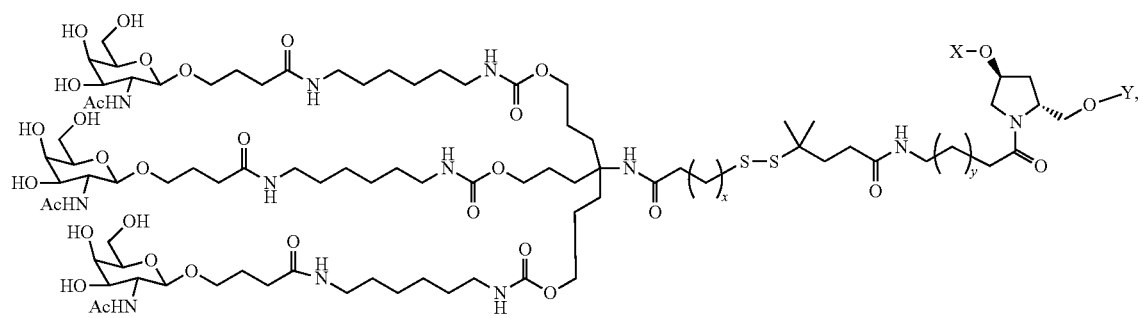
x = 0-30
y = 1-15
(Formul XXIX)
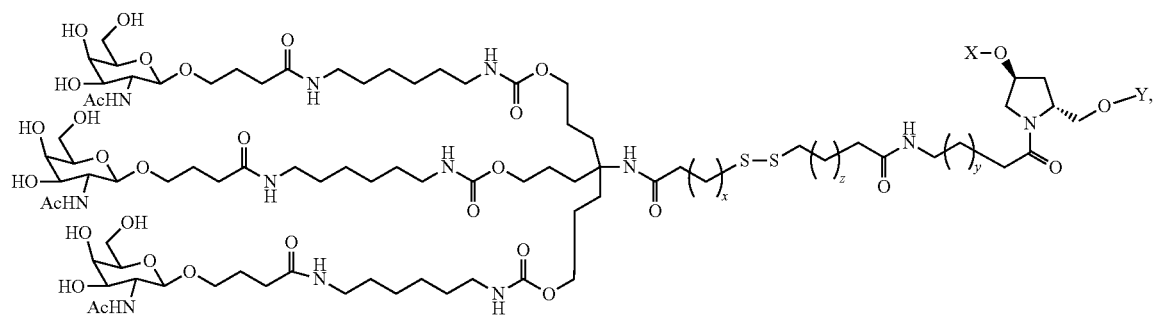
x = 0-30
y = 1-15
z = 1-20
(Formul XXX)
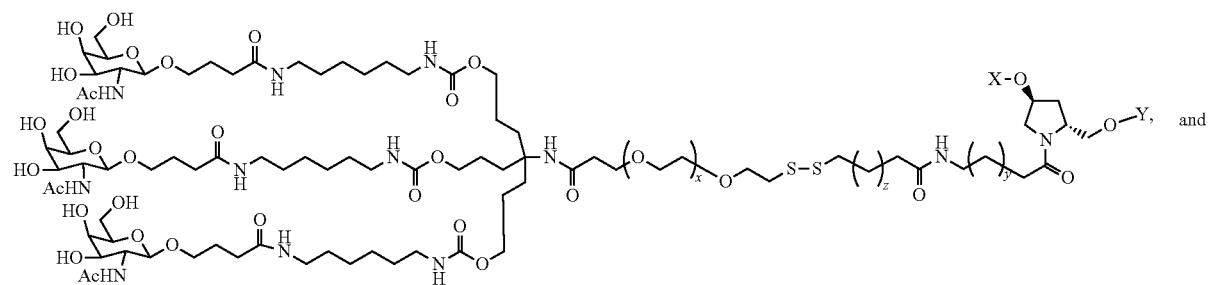
x = 1-30
y = 1-15
z = 1-20

(Formul XXXI)

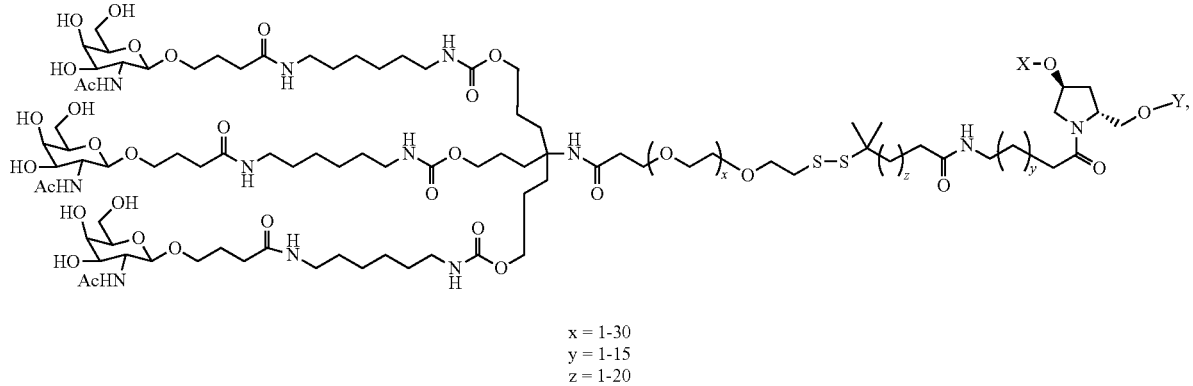

x = 1-30
y = 1-15
z = 1-20 when one of X or Y is an oligonucleotide, the other is a hydrogen.

In certain embodiments of the compositions and methods of the invention, a ligand is one or more GalNAc (N-acetyl-galactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

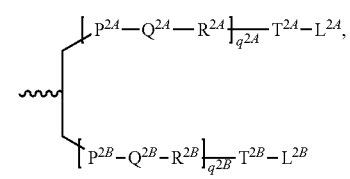

Formula XXXII

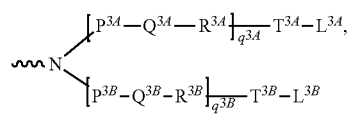

Formula XXXIII

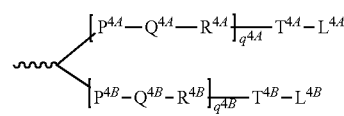

Formula XXXIV

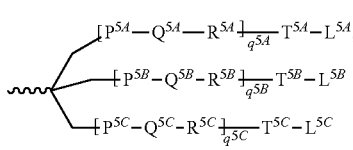

Formula XXXV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R), C(R')=C(R''), CC or C(O); $R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

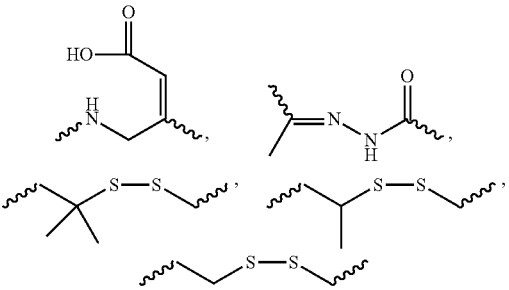

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and R$^a$ is H or amino acid side chain. Trivalent conjugating GalNAc derivatives are particularly useful for use with RNAi agents for inhibiting the expression of a target gene, such as those of formula (XXXVI):

Formula XXXVI

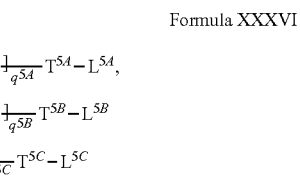

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat.

Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject (e.g., a subject in need thereof, such as a subject having a disorder that would benefit from reduction in PCSK9 expression) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knock-down of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275;

Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the PCSK9 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436, 146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector sui for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5)

malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The pharmaceutical compositions containing the iRNA are useful for treating a disease or disorder associated with the expression or activity of a PCSK9, e.g. a disease or disorder that would benefit from reduction in PCSK9 expression. Such pharmaceutical compositions are formulated based on the mode of delivery. One example is compositions that are formulated for systemic administration via parenteral delivery, e.g., by subcutaneous (SC), intramuscular (IM), or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of a PCSK9 gene.

Preferably, in the methods of the invention an iRNA agent is administered to a subject as a fixed dose. In one particular embodiment, a fixed dose of an iRNA agent of the invention is based on a predetermined weight or age.

In some embodiments, the RNAi agent is administered as a fixed dose of between about 200 mg to about 850 mg, between about 200 mg to about 500 mg, between about 200 mg to about 400 mg, between about 200 mg to about 300 mg, between about 100 mg to about 800 mg, between about 100 mg to about 750 mg, between about 100 mg to about 700 mg, between about 100 mg to about 650 mg, between about 100 mg to about 600 mg, between about 100 mg to about 550 mg, between about 100 mg to about 500 mg, between about 200 mg to about 850 mg, between about 200 mg to about 800 mg, between about 200 mg to about 750 mg, between about 200 mg to about 700 mg, between about 200 mg to about 650 mg, between about 200 mg to about 600 mg, between about 200 mg to about 550 mg, between about 200 mg to about 500 mg, between about 300 mg to about 850 mg, between about 300 mg to about 800 mg, between about 300 mg to about 750 mg, between about 300 mg to about 700 mg, between about 300 mg to about 650 mg, between about 300 mg to about 600 mg, between about 300 mg to about 550 mg, between about 300 mg to about 500 mg, between about 400 mg to about 850 mg, between about 400 mg to about 800 mg, between about 400 mg to about 750 mg, between about 400 mg to about 700 mg, between about 400 mg to about 650 mg, between about 400 mg to about 600 mg, between about 400 mg to about 550 mg, or between about 400 mg to about 500 mg.

In some embodiments, the RNAi agent is administered as a fixed dose of about about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, or about 850 mg.

In some embodiments, subjects are administered, e.g., subcutaneously or intramuscularly, multiple doses of a therapeutic amount of iRNA.

The iRNA may be formulated in a pharmaceutical composition at a suitable concentration such that a suitable volume of the composition is administered to the subject, such as about 1.0 mls, 1.1 mls, 1.2 mls, 1.3 mls, 1.4 mls, 1.5 mls, 1.6 mls, 1.7 mls, 1.8 mls, 1.9 mls, or about 2.0 mls of a pharmaceutical composition. For example, in one embodiment, an iRNA agent of the invention is formulated in a suitable pharmaceutical formulation at about 200 mg/ml such that administration of about 1.5 mls of the formulation to a subject provides a 300 mg fixed dose of the agent.

As described herein, a single dose of the iRNA agents or pharmaceutical compositions comprising such agents can be long lasting, such that subsequent doses are administered at not more than 1 week, 2 weeks, 1 month, 2 month, 3 month, 4 month, 5 month, or 6 month intervals.

In some embodiments, subjects are administered, e.g., subcutaneously or intramuscularly, a repeat dose of a therapeutic amount of iRNA. A repeat-dose regimine may include administration of a therapeutic amount of iRNA on a regular basis, such as once a month, once every two months, once a quarter, once every four months, once every five months, or biannually. In some embodiments of the invention, a single dose of the pharmaceutical compositions of the invention is administered once per quarter (qQ). In other embodiments of the invention, a single dose of the pharmaceutical compositions of the invention is administered bi-annually (i.e., every six months). Administration can be repeated, e.g., once every quarter for 6 months, one year, two years or longer, e.g., administered chronically.

In some embodiments, the RNAi agent is administered in a dosing regimen that includes a loading phase followed by a maintenance phase.

The loading phase may include a single administration of the RNAi agent during the first week, a single administration of the RNAi agent during the first two weeks, or a single administration of the RNAi agent during the first month at a fixed dose of, for example, about 100 mg to about 700 mg, about 150 mg to about 700 mg, about 200 mg to about 700 mg, about 250 mg to about 700 mg, about 300 mg to about 700 mg, about 350 mg to about 700 mg, about 400 mg to about 700 mg, about 450 mg to about 700 mg, about 500 mg to about 700 mg, about 550 mg to about 700 mg, about 600 to about 700 mg, about 650 to about 700 mg, about 100 mg to about 650 mg, about 150 mg to about 650 mg, about 200 mg to about 650 mg, about 250 mg to about 650 mg, about 300 mg to about 650 mg, about 350 mg to about 650 mg, about 400 mg to about 650 mg, about 450 mg to about 650 mg, about 500 mg to about 650 mg, about 550 mg to about 650 mg, about 600 to about 650 mg, about 100 mg to about 600 mg, about 150 mg to about 600 mg, about 200 mg to about 600 mg, about 250 mg to about 600 mg, about 300 mg to about 600 mg, about 350 mg to about 600 mg, about 400 mg to about 600 mg, about 450 mg to about 600 mg, about 500 mg to about 600 mg, about 550 mg to about 600 mg, about 100 mg to about 550 mg, about 150 mg to about 550 mg, about 200 mg to about 550 mg, about 250 mg to about 550 mg, about 300 mg to about 550 mg, about 350 mg to about 550 mg, about 400 mg to about 550 mg, about 450 mg to about 550 mg, about 500 mg to about 550 mg, about 100 mg to about 500 mg, about 150 mg to about 500 mg, about 200 mg to about 500 mg, about 250 mg to about 500 mg, about 300 mg to about 500 mg, about 350 mg to about 500 mg, about 400 mg to about 500 mg, or about 450 mg to about 500 mg, e.g., a fixed dose of about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, or about 700 mg. Values and ranges intermediate to the foregoing recited values are also intended to be part of this invention.

The maintenance phase may include administration of a dose of the RNAi agent to the subject once a month, once every two months, once every three months, once every four months, once every five months, or once every six months. In one particular embodiment, the maintenance dose is administered to the subject once a month.

The maintenance dose or doses can be the same or lower than the initial dose, e.g., one-half of the initial dose. For example, a maintenance dose may be about 25 mg to about 100 mg administered to the subject monthly, for example about 25 mg to about 75 mg, about 25 mg to about 50 mg, or about 50 mg to about 75 mg, e.g., about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. Values and ranges intermediate to the foregoing recited values are also intended to be part of this invention.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

A. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research*, 1994, 11, 1385; Ho et al., *J. Pharm. Sci.*, 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

iii. Microparticles an RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.*, 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.*, 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPassa D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a hemolytic disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by PCSK9 expression. In any event, the administering physician can adjust the amount and timing of iRNA administration on the basis of results observed using standard measures of efficacy known in the art or described herein.

VI. Kits

The present invention also provides kits for using any of the iRNA agents and/or performing any of the methods of the invention. Such kits include one or more RNAi agent(s) and instructions for use, e.g., instructions for inhibiting expression of a PCSK9 in a cell by contacting the cell with the RNAi agent(s) in an amount effective to inhibit expression of the PCSK9. The kits may optionally further comprise means for contacting the cell with the RNAi agent (e.g., an injection device), or means for measuring the inhibition of PCSK9 (e.g., means for measuring the inhibition of PCSK9 mRNA protein). Such means for measuring the inhibition of PCSK9 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein, as well as the Sequence Listing and Figures, are incorporated by reference in their entirety. In case of conflict, the present specification, including definitions, will control. In addition, the materials, methods, and examples are illustrative only and not intended to be limiting.

EXAMPLES

Example 1. Synthesis of GalNAc-Conjugated Oligonucleotides

A series of siRNA duplexes targeting nucleotides 3544-3623 of the human PCSK9 gene (SEQ ID NO:1) were designed, synthesized. These same sequences were also synthesized with various nucleotide modifications and conjugated with a trivalent GalNAc. The sense and antisense strand sequences of the modified duplexes are shown in Table 1.

TABLE B

Abbreviations of nucleotide monomers used in nucleic acid sequence representation.

| Abbreviation | Nucleotide(s) |
| --- | --- |
| A | Adenosine-3'-phosphate |
| Ab | beta-L-adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine-3'-phosphate |

TABLE B-continued

Abbreviations of nucleotide monomers used in nucleic acid sequence representation.

| Abbreviation | Nucleotide(s) |
| --- | --- |
| dTs | 2'-deoxythymidine-3'-phosphorothioate |
| dU | 2'-deoxyuridine-3'-phosphate |
| dUs | 2'-deoxyuridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |
| (Teos) | 2'-O-methoxyethyl-5-methyluridine-3'-phosphorothioate |
| (m5Ceo) | 2'-O-methoxyethyl-5-methylcytidine-3'-phosphate |
| (m5Ceos) | 2'-O-methoxyethyl-5-methylcytidine-3'-phosphorothioate |
| (A3m) | 3'-O-methyladenosine-2'-phosphate |
| (A3mx) | 3'-O-methyl-xylofuranosyladenosine-2'-phosphate |
| (G3m) | 3'-O-methylguanosine-2'-phosphate |
| (G3mx) | 3'-O-methyl-xylofuranosylguanosine-2'-phosphate |
| (C3m) | 3'-O-methylcytidine-2'-phosphate |
| (C3mx) | 3'-O-methyl-xylofuranosylcytidine-2'-phosphate |
| (U3m) | 3'-O-methyluridine-2'-phosphate |
| (U3mx) | 3'-O-methylxylouridine-2'-phosphate |
| (Chd) | 2'-O-hexadecyl-cytidine-3'-phosphate |
| (pshe) | Hydroxyethylphosphorothioate |
| (Uhd) | 2'-O-hexadecyl-uridine-3'-phosphate |
| (Tgn) | Thymidine-glycol nucleic acid (GNA) S-Isomer |
| (Cgn) | Cytidine-glycol nucleic acid (GNA) |
| (Chd) | 2'-O-hexadecyl-cytidine-3'-phosphate |
| (Ggn) | 2'-O-hexadecyl-cytidine-3'-phosphate |
| (Agn) | Adenosine-glycol nucleic acid (GNA) |
| P | 5'-phosphate |
| (m5Cam) | 2'-O-(N-methylacetamide)-5-methylcytidine-3'-phosphate |
| (m5Cams) | 2'-O-(N-methylacetamide)-5-methylcytidine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| (Aam) | 2'-O-(N-methylacetamide)adenosine-3'-phosphate |
| (Aams) | 2'-O-(N-methylacetamide)adenosine-3'-phosphorothioate |
| (Gam) | 2'-O-(N-methylacetamide)guanosine-3'-phosphate |
| (Gams) | 2'-O-(N-methylacetamide)guanosine-3'-phosphorothioate |
| (Uyh) | 2'-O-(1-hexyl-4-methylene-1,2,3-triazolyl)-uridine-3'-phosphate |
| (Ayh) | 2'-O-(1-hexyl-4-methylene-1,2,3-triazolyl)-adenosine-3'-phosphate |
| (Gyh) | 2'-O-(1-hexyl-4-methylene-1,2,3-triazolyl)-guanosine-3'-phosphate |
| (Cyh) | 2'-O-(1-hexyl-4-methylene-1,2,3-triazolyl)-cytidine-3'-phosphate |
| (iA) | inverted adenosine-5'-phosphate |
| (iC) | inverted cytidine-5'-phosphate |

TABLE 1

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-53806 | A-110717 | 7 | CfaAfgCfaGfaCfaAfUfuUfaUfcUfuUfuUfL96 | 3544 | A-109589 | 8 | aAfaAfaGfaUfaAfaUfaAfaugUfcUfgcCfuUfgsCfsu |
| AD-53806 | A-110717 | 9 | CfaAfgCfaGfaCfaAfUfuUfaUfcUfuUfuUfL96 | 3544 | A-109589 | 10 | aAfaAfaGfaUfaAfaUfaAfaugUfcUfgcCfuUfgsCfsu |
| AD-53806 | A-110717 | 11 | CfaAfgCfaGfaCfaAfUfuUfaUfcUfuUfuUfL96 | 3544 | A-109589 | 12 | aAfaAfaGfaUfaAfaUfaAfaugUfcUfgcCfuUfgsCfsu |
| AD-53806 | A-110717 | 13 | CfaAfgCfaGfaCfaAfUfuUfaUfcUfuUfuUfL96 | 3544 | A-109589 | 14 | aAfaAfaGfaUfaAfaUfaAfaugUfcUfgcCfuUfgsCfsu |
| AD-53806 | A-110717 | 15 | CfaAfgCfaGfaCfaAfUfuUfaUfcUfuUfuUfL96 | 3544 | A-109589 | 16 | aAfaAfaGfaUfaAfaUfaAfaugUfcUfgcCfuUfgsCfsu |
| AD-53806 | A-110717 | 17 | CfaAfgCfaGfaCfaAfUfuUfaUfcUfuUfuUfL96 | 3544 | A-109589 | 18 | aAfaAfaGfaUfaAfaUfaAfaugUfcUfgcCfuUfgsCfsu |
| AD-53806 | A-110717 | 19 | CfaAfgCfaGfaCfaAfUfuUfaUfcUfuUfuUfL96 | 3544 | A-109589 | 20 | aAfaAfaGfaUfaAfaUfaAfaugUfcUfgcCfuUfgsCfsu |
| AD-53806 | A-110717.6 | 21 | CfaAfgCfaGfaCfaAfUfuUfaUfcUfuUfuUfL96 | 3544 | A-109589 | 22 | aAfaAfaGfaUfaAfaUfaAfaugUfcUfgcCfuUfgsCfsu |
| AD-53806 | A-110717.7 | 23 | CfaAfgCfaGfaCfaAfUfuUfaUfcUfuUfuUfL96 | 3544 | A-109589 | 24 | aAfaAfaGfaUfaAfaUfaAfaugUfcUfgcCfuUfgsCfsu |
| AD-53806 | A-110717.8 | 25 | CfaAfgCfaGfaCfaAfUfuUfaUfcUfuUfuUfL96 | 3544 | A-109589 | 26 | aAfaAfaGfaUfaAfaUfaAfaugUfcUfgcCfuUfgsCfsu |
| AD-53806 | A-110717.9 | 27 | caAfgCfaGfaCfaAfUfuUfaUfcUfuUfuUfL96 | 3544 | A-109589 | 28 | aAfaAfaGfaUfaAfaUfaAfaugUfcUfgcCfuUfgsCfsu |
| AD-56979 | A-116393 | 29 | caAfgCfaGfaCfaAfUfuUfaUfcUfuUfuUfL96 | 3544 | A-109589 | 30 | aAfaAfaGfaUfaAfaUfaAfaugUfcUfgcCfuUfgsCfsu |
| AD-56979 | A-116393 | 31 | (iC)aAfgcCfaGfaCfaAfUfuUfaUfcUfuUfuUfL96 | 3544 | A-109589 | 32 | aAfaAfaGfaUfaAfaUfaAfaugUfcUfgcCfuUfgsCfsu |
| AD-56975 | A-116394 | 33 | (iC)aAfgcCfaGfaCfaAfUfuUfaUfcUfuUfuUfL96 | 3544 | A-109589 | 34 | aAfaAfaGfaUfaAfaUfaAfaugUfcUfgcCfuUfgsCfsu |
| AD-56975 | A-116394 | 35 | (iC)aAfgcCfaGfaCfaAfUfuUfaUfcUfuUfuUfL96 | 3544 | A-109589 | 36 | aAfaAfaGfaUfaAfaUfaAfaugUfcUfgcCfuUfgsCfsu |
| AD-56975 | A-116394 | 37 | (iC)aAfgcCfaGfaCfaAfUfuUfaUfcUfuUfuUfL96 | 3544 | A-109589 | 38 | aAfaAfaGfaUfaAfaUfaAfaugUfcUfgcCfuUfgsCfsu |
| AD-56975 | A-116394 | 39 | (iC)aAfgcCfaGfaCfaAfUfuUfaUfcUfuUfuUfL96 | 3544 | A-109589 | 40 | aAfaAfaGfaUfaAfaUfaAfaugUfcUfgcCfuUfgsCfsu |
| AD-56983 | A-116400 | 41 | CbaAfgCfaGfaCfaAfUfuUfaUfcUfuUfuUfL96 | 3544 | A-109589 | 42 | aAfaAfaGfaUfaAfaUfaAfaugUfcUfgcCfuUfgsCfsu |
| AD-56983 | A-116400 | 43 | CbaAfgCfaGfaCfaAfUfuUfaUfcUfuUfuUfL96 | 3544 | A-109589 | 44 | aAfaAfaGfaUfaAfaUfaAfaugUfcUfgcCfuUfgsCfsu |
| AD-56983 | A-116400 | 45 | CbaAfgCfaGfaCfaAfUfuUfaUfcUfuUfuUfL96 | 3544 | A-109589 | 46 | aAfaAfaGfaUfaAfaUfaAfaugUfcUfgcCfuUfgsCfsu |
| AD-56983 | A-116400 | 47 | CbaAfgCfaGfaCfaAfUfuUfaUfcUfuUfuUfL96 | 3544 | A-109589 | 48 | aAfaAfaGfaUfaAfaUfaAfaugUfcUfgcCfuUfgsCfsu |
| AD-56983 | A-116400 | 49 | CbaAfgCfaGfaCfaAfUfuUfaUfcUfuUfuUfL96 | 3544 | A-109589 | 50 | aAfaAfaGfaUfaAfaUfaAfaugUfcUfgcCfuUfgsCfsu |
| AD-56977 | A-116406 | 51 | CfaagCfaGfaCfaAfUfuUfaUfcUfuUfuUfL96 | 3544 | A-109589 | 52 | aAfaAfaGfaUfaAfaUfaAfaugUfcUfgcCfuUfgsCfsu |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56977 | A-116406 | 53 | CfaagCfagGfacCfAfUfaCfUfcUfcUfuUfuUfL96 | 3544 | A-109589 | 54 | aAfaAfaGfaUfaAfaUfauGfUfcUfgCfuUfgsCfsu |
| AD-56977 | A-116406 | 55 | CfaagCfagGfacCfAfUfaCfUfcUfaUfcUfuUfuUfL96 | 3544 | A-109589 | 56 | aAfaAfaGfaUfaAfaUfauGfUfcUfgCfuUfgsCfsu |
| AD-56976 | A-116407 | 57 | CfaagCfagGfacCfAfUfaCfUfcUfuUfaUfcUfuUfL96 | 3544 | A-109589 | 58 | aAfaAfaGfaUfaAfaUfauGfUfcUfgCfuUfgsCfsu |
| AD-56976 | A-116407 | 59 | CfaagCfagGfacCfAfUfaCfUfcUfaucUfuUfuUfL96 | 3544 | A-109589 | 60 | aAfaAfaGfaUfaAfaUfauGfUfcUfgCfuUfgsCfsu |
| AD-56980 | A-116408 | 61 | CfaagCfagaCfaCfAfUfUfaCfUfcUfaUfuUfuUfL96 | 3544 | A-109589 | 62 | aAfaAfaGfaUfaAfaUfauGfUfcUfgCfuUfgsCfsu |
| AD-56980 | A-116408 | 63 | CfaagCfagaCfaCfAfUfUfaCfUfcUfaucUfuUfuUfL96 | 3544 | A-109589 | 64 | aAfaAfaGfaUfaAfaUfauGfUfcUfgCfuUfgsCfsu |
| AD-56984 | A-116409 | 65 | CfaagCfagaCfaCfAfUfUfaCfUfcUfuUfuUfuUfL96 | 3544 | A-109589 | 66 | aAfaAfaGfaUfaAfaUfauGfUfcUfgCfuUfgsCfsu |
| AD-56984 | A-116409 | 67 | CfaagCfagaCfaCfAfUfUfaCfUfaucUfuUfuUfuUfL96 | 3544 | A-109589 | 68 | aAfaAfaGfaUfaAfaUfauGfUfcUfgCfuUfgsCfsu |
| AD-56987 | A-116410 | 69 | CfaagCfagaCfaCfAfUfUfaCfUfaucUfuUfuuuUfL96 | 3544 | A-109589 | 70 | aAfaAfaGfaUfaAfaUfauGfUfcUfgCfuUfgsCfsu |
| AD-56987 | A-116410 | 71 | CfaagCfagaCfaCfAfUfUfaCfUfuUfaucUfuUfuUfL96 | 3544 | A-109589 | 72 | aAfaAfaGfaUfaAfaUfauGfUfcUfgCfuUfgsCfsu |
| AD-56991 | A-116415 | 73 | CfaagCfagaCfaCfAfUfUfaCfUfaUfaucutuuuuL96 | 3544 | A-109589 | 74 | aAfaAfaGfaUfaAfaUfauGfUfcUfgCfuUfgsCfsu |
| AD-56993 | A-116416 | 75 | CfaagcagaCfaCfAfUfUfaucUfuUfaucutuuuuL96 | 3544 | A-109589 | 76 | aAfaAfaGfaUfaAfaUfauGfUfcUfgCfuUfgsCfsu |
| AD-56995 | A-116417 | 77 | CfaagcagaCfaCfAfUfUfuuauacutuuuuL96 | 3544 | A-109589 | 78 | aAfaAfaGfaUfaAfaUfauGfUfcUfgCfuUfgsCfsu |
| AD-56978 | A-116418 | 79 | CfaAfAfgCfCfagaCfaCfAfUfUfaCfUfuUfaUfcUfuUfuUfL96 | 3544 | A-109589 | 80 | aAfaAfaGfaUfaAfaUfauGfUfcUfgCfuUfgsCfsu |
| AD-56978 | A-116418 | 81 | CfaAfAfgCfCfagaCfaCfAfUfUfaCfUfcUfuUfuUfuUfL96 | 3544 | A-109589 | 82 | aAfaAfaGfaUfaAfaUfauGfUfcUfgCfuUfgsCfsu |
| AD-56981 | A-116419 | 83 | CfaAfAfgCfCfagaCfaCfAfUfUfaCfUfAfUfcUfuUfuUfL96 | 3544 | A-109589 | 84 | aAfaAfaGfaUfaAfaUfauGfUfcUfgCfuUfgsCfsu |
| AD-56985 | A-116420 | 85 | CfaAfAfgCfCfagaCfaCfAfUfUfaCfUfAfUfcUfuUfuUfL96 | 3544 | A-109589 | 86 | aAfaAfaGfaUfaAfaUfauGfUfcUfgCfuUfgsCfsu |
| AD-56988 | A-116421 | 87 | CfaAfAfgCfCfAfgacCfaCfAfUfUfaCfUfAfUfcUfuUfuUfL96 | 3544 | A-109589 | 88 | aAfaAfaGfaUfaAfaUfauGfUfcUfgCfuUfgsCfsu |
| AD-56988 | A-116421 | 89 | CfaAfAfgCfCfAfgacCfaCfAfUfUfaCfUfCfUfcUfuUfuUfL96 | 3544 | A-109589 | 90 | aAfaAfaGfaUfaAfaUfauGfUfcUfgCfuUfgsCfsu |
| AD-56982 | A-116426 | 91 | CfaAfgcaGfaCfAfCfAfUfUfaCfUfAfUfcUfuUfuUfL96 | 3544 | A-109589 | 92 | aAfaAfaGfaUfaAfaUfauGfUfcUfgCfuUfgsCfsu |
| AD-56982 | A-116426 | 93 | CfaAfgcaGfaCfAfCfAfUfUfaCfUfCfUfcUfuUfuUfL96 | 3544 | A-109589 | 94 | aAfaAfaGfaUfaAfaUfauGfUfcUfgCfuUfgsCfsu |
| AD-56986 | A-116428 | 95 | CfaAfgCfagaCfAfCfAfUfUfaCfUfAfUfcUfuUfuUfL96 | 3544 | A-109589 | 96 | aAfaAfaGfaUfaAfaUfauGfUfcUfgCfuUfgsCfsu |
| AD-56986 | A-116428 | 97 | CfaAfgCfagaCfAfCfAfUfUfaCfUfCfUfcUfuUfuUfL96 | 3544 | A-109589 | 98 | aAfaAfaGfaUfaAfaUfauGfUfcUfgCfuUfgsCfsu |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56986 | A-116428 | 99 | CfaAfAfgCfagaCfAfUfuUfaUfcUfiuUfuUfL96 | 3544 | A-109589 | 100 | aAfaAfaGfaGfaUfaAfaUfaAfaugUfcUfgcUfuUfgsCfsu |
| AD-56989 | A-116430 | 101 | CfaAfAfgCfaGfacAfUfuUfaUfcUfuUfuUfL96 | 3544 | A-109589 | 102 | aAfaAfaGfaGfaUfaAfaUfaAfaugUfcUfgcUfuUfgsCfsu |
| AD-56990 | A-116432 | 103 | CfaAfAfgCfaGfaCfAfuuUfaUfcUfuUfuUfL96 | 3544 | A-109589 | 104 | aAfaAfaGfaGfaUfaAfaUfaAfaugUfcUfgcUfuUfgsCfsu |
| AD-56992 | A-116434 | 105 | CfaAfAfgCfaGfaCfAfUfaucUfuUfuUfL96 | 3544 | A-109589 | 106 | aAfaAfaGfaGfaUfaAfaUfaAfaugUfcUfgcUfuUfgsCfsu |
| AD-56992 | A-116434 | 107 | CfaAfAfgCfaGfaCfAfUfuUfaucUfuUfuUfL96 | 3544 | A-109589 | 108 | aAfaAfaGfaGfaUfaAfaUfaAfaugUfcUfgcUfuUfgsCfsu |
| AD-56994 | A-116436 | 109 | CfaAfAfgCfaGfaCfAfUfuUfaUfcUfuUfuUfL96 | 3544 | A-109589 | 110 | aAfaAfaGfaGfaUfaAfaUfaAfaugUfcUfgcUfuUfgsCfsu |
| AD-56994 | A-116436 | 111 | CfaAfAfgCfaGfaCfAfUfuUfaUfcUfuUfuUfL96 | 3544 | A-109589 | 112 | aAfaAfaGfaGfaUfaAfaUfaAfaugUfcUfgcUfuUfgsCfsu |
| AD-56996 | A-116438 | 113 | caagCfaGfaCfAfUfuUfaUfcUfuUfuUfL96 | 3544 | A-109589 | 114 | aAfaAfaGfaGfaUfaAfaUfaAfaugUfcUfgcUfuUfgsCfsu |
| AD-57001 | A-116440 | 115 | CfaAfgcagaCfAfUfuUfaUfcUfuUfuUfL96 | 3544 | A-109589 | 116 | aAfaAfaGfaGfaUfaAfaUfaAfaugUfcUfgcUfuUfgsCfsu |
| AD-57007 | A-116442 | 117 | CfaAfAfgCfaGfaCfAfaUfuuuaUfcUfuUfuUfL96 | 3544 | A-109589 | 118 | aAfaAfaGfaGfaUfaAfaUfaAfaugUfcUfgcUfuUfgsCfsu |
| AD-57013 | A-116444 | 119 | CfaAfAfgCfaGfaCfAfUfuUfauucuUfcUfuuuuL96 | 3544 | A-109589 | 120 | aAfaAfaGfaGfaUfaAfaUfaAfaugUfcUfgcUfuUfgsCfsu |
| AD-57019 | A-116446 | 121 | CfaAfAfgCfaGfaCfAfUfuUfaUfcUfuUfL96 | 3544 | A-109589 | 122 | aAfaAfaGfaGfaUfaAfaUfaAfaugUfcUfgcUfuUfgsCfsu |
| AD-57022 | A-116448 | 123 | CfaAfAfgCfaGfaCfAfUfuUfaUfcCfUfuUfuUfL96 | 3544 | A-109589 | 124 | aAfaAfaGfaGfaUfaAfaUfaAfaugUfcUfgcUfuUfgsCfsu |
| AD-57025 | A-116449 | 125 | CfaAfAfgCfaGfaCfAfUfcUfaUfcUfuUfuUfL96 | 3544 | A-109589 | 126 | aAfaAfaGfaGfaUfaAfaUfaAfaugUfcUfgcUfuUfgsCfsu |
| AD-56997 | A-116450 | 127 | CfaAfAfgCfaGfaCfAfUfuUfaAfcUfuUfuUfL96 | 3544 | A-109589 | 128 | aAfaAfaGfaGfaUfaAfaUfaAfaugUfcUfgcUfuUfgsCfsu |
| AD-57002 | A-116452 | 129 | CfaAfAfgCfaGfaCfAfUfuUfaUfcCfuUfuUfL96 | 3544 | A-109589 | 130 | aAfaAfaGfaGfaUfaAfaUfaAfaugUfcUfgcUfuUfgsCfsu |
| AD-57008 | A-116453 | 131 | CfaAfAfgCfaGfaCfAfCfAfUfuUfaUfcUfuUfuUfL96 | 3544 | A-109589 | 132 | aAfaAfaGfaGfaUfaAfaUfaAfaugUfcUfgcUfuUfgsCfsu |
| AD-57014 | A-116454 | 133 | CfaAfAfgCfaGfaCfAfGfaCfAfUfuUfaUfcUfuUfuUfL96 | 3544 | A-109589 | 134 | aAfaAfaGfaGfaUfaAfaUfaAfaugUfcUfgcUfuUfgsCfsu |
| AD-57020 | A-116455 | 135 | CfaAfAfgCfaGfaCfAfUfuUfaUfcUfuUfuUfL96 | 3544 | A-1095893 | 136 | aAfaAfaGfaGfaUfaAfaUfaAfaugUfcUfgcUfuUfgsCfsu |
| AD-57020 | A-116455 | 137 | CfaAfAfgCfaGfaCfAfUfuUfaUfcUfuUfuUfL96 | 3544 | A-1095893 | 138 | aAfaAfaGfaGfaUfaAfaUfaAfaugUfcUfgcUfuUfgsCfsu |
| AD-57026 | A-116457 | 139 | CfaAfAfgCfaGfaCfAfUfuUfaUfcuuUfuUfuUfL96 | 3544 | A-1095893 | 140 | aAfaAfaGfaGfaUfaAfaUfaAfaugUfcUfgcUfuUfgsCfsu |
| AD-57003 | A-116460 | 141 | CfaAfAfgCfaGfaCfAfUfuuaUfcUfuUfuUfL96 | 3544 | A-109589 | 142 | aAfaAfaGfaGfaUfaAfaUfaAfaugUfcUfgcUfuUfgsCfsu |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-57009 | A-116462 | 143 | CfaAfgCfaGfaCfauuUfaUfcUfuUfuUfL96 | 3544 | A-109589 | 144 | aAfaAfaGfaUfaAfaugUfcUfgCfuUfgsCfsu |
| AD-57015 | A-116464 | 145 | CfaAfgCfaGfaCfacaUfaUfcUfuUfuUfL96 | 3544 | A-109589 | 146 | aAfaAfaGfaUfaAfaugUfcUfgCfuUfgsCfsu |
| AD-57023 | A-116467 | 147 | CfaAfgCfaGfaCfAfUfuUfaucUfcUfuUfuUfL96 | 3544 | A-109589 | 148 | aAfaAfaGfaUfaAfaugUfcUfgCfuUfgsCfsu |
| AD-57027 | A-116469 | 149 | CfaAfgCfaGfaCfAfUfuuaUfcUfuUfuUfL96 | 3544 | A-109589 | 150 | aAfaAfaGfaUfaAfaugUfcUfgCfuUfgsCfsu |
| AD-56998 | A-116471 | 151 | CfaAfgCfagaCfAfUfuUfaUfcUfuUfuUfL96 | 3544 | A-109589 | 152 | aAfaAfaGfaUfaAfaugUfcUfgCfuUfgsCfsu |
| AD-57004 | A-116473 | 153 | CfaAfgcaGfaCfAfUfuUfaUfcUfuUfuUfL96 | 3544 | A-109589 | 154 | aAfaAfaGfaUfaAfaugUfcUfgCfuUfgsCfsu |
| AD-57010 | A-116475 | 155 | CfaagCfaGfaCfAfUfuUfaUfcUfuUfuUfL96 | 3544 | A-109589 | 156 | aAfaAfaGfaUfaAfaugUfcUfgCfuUfgsCfsu |
| AD-57016 | A-116477 | 157 | caAfgCfaGfaCfAfUfuUfaUfcUfuUfuUfL96 | 3544 | A-109589 | 158 | aAfaAfaGfaUfaAfaugUfcUfgCfuUfgsCfsu |
| AD-56999 | A-116479 | 159 | CfaAfgCfaGfaCfAfUfuUfaUfcUfuUfuUfL96 | 3544 | A-109589 | 160 | aAfaAfaGfaUfaAfaugUfcUfgCfuUfgsCfsu |
| AD-56999 | A-116479 | 161 | CfaAfgCfaGfaCfAfUfuUfaUfCfcUfuUfuUfL96 | 3544 | A-109589 | 162 | aAfaAfaGfaUfaAfaugUfcUfgCfuUfgsCfsu |
| AD-57021 | A-116481 | 163 | CfaAfgCfaGfaCfAfUfuUfuuaUfcUfuUfuUfL96 | 3544 | A-109589 | 164 | aAfaAfaGfaUfaAfaugUfcUfgCfuUfgsCfsu |
| AD-57024 | A-116483 | 165 | CfaAfgCfaGfaCfAfUfuUfaUfcCfuUfuUfL96 | 3544 | A-109589 | 166 | aAfaAfaGfaUfaAfaugUfcUfgCfuUfgsCfsu |
| AD-57005 | A-116486 | 167 | CfaAfgCfaGfCfAfUfuUfaUfcUfuuuUfL96 | 3544 | A-109589 | 168 | aAfaAfaGfaUfaAfaugUfcUfgCfuUfgsCfsu |
| AD-57011 | A-116488 | 169 | CfaAfgCfaGfaCfAfUfuuaUfcUfuUfuUfL96 | 3544 | A-109589 | 170 | aAfaAfaGfaUfaAfaugUfcUfgCfuUfgsCfsu |
| AD-57017 | A-116490 | 171 | CfaAfgCfagaCfAfUfuuaUfcUfuUfuUfL96 | 3544 | A-109589 | 172 | aAfaAfaGfaUfaAfaugUfcUfgCfuUfgsCfsu |
| AD-57000 | A-116492 | 173 | Cf(Aeo)Af(Geo)CfaGfaCfAfUfuUfaUfcUf(Teo)Uf(Teo)UfL96 | 3544 | A-109589 | 174 | aAfaAfaGfaUfaAfaugUfcUfgCfuUfgsCfsu |
| AD-57000 | A-116492 | 175 | Cf(Aeo)Af(Geo)CfaGfaCfAfUfuUfaUfcUf(Teo)Uf(Teo)UfL96 | 3544 | A-109589 | 176 | aAfaAfaGfaUfaAfaugUfcUfgCfuUfgsCfsu |
| AD-57000 | A-116492 | 177 | Cf(Aeo)Af(Geo)CfaGfaCfAfUfuUfaUfcUfcUf(Teo)UfL96 | 3544 | A-109589 | 178 | aAfaAfaGfaUfaAfaugUfcUfgCfuUfgsCfsu |
| AD-57006 | A-116494 | 179 | Cf(Aeo)Af(Geo)CfaGfaCfAfUfuUf(Aeo)Uf(m5Ceo)Uf(Teo)Uf(Teo)UfL96 | 3544 | A-109589 | 180 | aAfaAfaGfaUfaAfaugUfcUfgCfuUfgsCfsu |
| AD-57006 | A-116494 | 181 | Cf(Aeo)Af(Geo)CfaGfaCfAfUfuUf(Aeo)Uf(m5Ceo)Uf(Teo)Uf(Teo)UfL96 | 3544 | A-109589 | 182 | aAfaAfaGfaUfaAfaugUfcUfgCfuUfgsCfsu |
| AD-57006 | A-116494 | 183 | Cf(Aeo)Af(Geo)CfaGfaCfAfUfuUf(Aeo)Uf(m5Ceo)Uf(Teo)Uf(Teo)UfL96 | 3544 | A-109589 | 184 | aAfaAfaGfaUfaAfaugUfcUfgCfuUfgsCfsu |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-57012 | A-116498 | 185 | Cf(Aeo)Af(Geo)CfaGfaCfAfUfuUfaUfcUf(Teo)Uf(Teo)UbL96 | 3544 | A-109589 | 186 | aAfaAfaGfaUfaAfaUfaugUfcUfgcUfuUfgsCfsu |
| AD-57018 | A-116500 | 187 | Cf(Aeo)Af(Geo)CfaGfaCfAfUfuUf(Aeo)Uf(m5Ceo)Uf(Teo)Uf(Teo)UbL96 | 3544 | A-109589 | 188 | aAfaAfaGfaUfaAfaUfaugUfcUfgCfuUfgsCfsu |
| AD-53812 | A-110718 | 189 | AfaGfcAfgAfcAfUfUfuUfAfuCfuUfuUfgAfL96 | 3545 | A-109591 | 190 | uCfaaAfaAfgAfuAfaauGfuCfgCfcUfusGfsu |
| AD-53818 | A-110719 | 191 | AfgCfaGfaCfaUfUfUfuAfuCfuUfuUfgUfgAfL96 | 3546 | A-109593 | 192 | uCfcaAfaAfaGfaUfaaaUfgUfcUfgCfusUfsg |
| AD-53766 | A-110679 | 193 | GfcAfgAfcAfuUfUfuAfuCfuUfuUfgUfgUfL96 | 3547 | A-109513 | 194 | aCfcCfaAfaAfaGfaUfuaaAfuGfuCfuGfcsUfsu |
| AD-53772 | A-110680 | 195 | AfgAfcAfuUfuUfaUfcUfuUfuUfgGfgUfcUfL96 | 3549 | A-109515 | 196 | aGfaCfcCfaAfaAfgaUfaAfaUfgUfcUfgGfsu |
| AD-53824 | A-110720 | 197 | GfaCfaUfuUfuAfuCfuUfuUfgGfgUfcUfuCfL96 | 3550 | A-109595 | 198 | aAfgAfcCfCfaAfaAfagaUfaAfaUfgUfcUfsg |
| AD-53778 | A-110681 | 199 | AfcAfUfuUfaUfcUfuUfuUfgGfgUfcUfuUfL96 | 3551 | A-109517 | 200 | aCfaGfaCfcCfaAfaagAfuAfaaUfgUfcUfsu |
| AD-53784 | A-110682 | 201 | UfuUfaUfcUfuUfuUfgGfgUfcUfuCfUfcUfL96 | 3554 | A-109519 | 202 | aGfgAfcAfgAfcCfcaaAfaGfaUfAfasUfsg |
| AD-53829 | A-110721 | 203 | UfuAfuCfuUfuUfuGfgGfuCfuUfcUfcUfuUfL96 | 3555 | A-109597 | 204 | aAfgGfaCfaGfaCfccaAfaAfgAfuAfasAfsu |
| AD-53790 | A-110683 | 205 | UfaUfcUfuUfuUfgGfgUfcUfuCfuCfuUfuUfL96 | 3556 | A-109521 | 206 | aGfaGfaAfgAfcCfcAfaAfaGfaUfasAfsa |
| AD-53835 | A-110722 | 207 | AfuCfuUfuUfgGfgUfcUfuCfuCfuUfcUfL96 | 3557 | A-109523 | 208 | aAfgAfgGfaCfaGfaCfccAfaAfaGfaUfasAfsa |
| AD-53796 | A-110684 | 209 | UfcUfuUfuUfgGfgUfcUfuCfuCfuUfuUfL96 | 3558 | A-109525 | 210 | aGfaAfgAfgGfaCfaGfacCfcAfaAfAfasUfsa |
| AD-53802 | A-110685 | 211 | UfUfUfuUfgGfgfucUfcUfuCfuCfuUfcUfgUfL96 | 3560 | A-109527 | 212 | aCfaGfaGfaAfgAfgGfacCfcAfaAfAfasGfsa |
| AD-53808 | A-110686 | 213 | UfuUfgGfgfucUfuCfuCfuUfcUfgUfcCfL96 | 3561 | A-109529 | 214 | aAfcAfgAfgAfgAfgGfacaGfcCfaAfasAfsg |
| AD-53795 | A-110723 | 215 | UfuGfgGfuCfuUfcUfcUfuCfuGfuuUfgAfL96 | 3562 | A-109601 | 216 | aAfcCfaAfcAfgAfgAfgGfacAfgAfcCfcAfasAfsa |
| AD-53801 | A-110724 | 217 | UfgGfgUfcUfuCfuCfuUfcUfgUfuGfuUfgAfL96 | 3563 | A-109603 | 218 | uCfaAfcAfcAfgAfggaAfcAfgAfcCfcAfasAfsa |
| AD-53807 | A-110725 | 219 | GfgGfuCfuuCfuCfuUfcUfgUfuGfuGfcAfL96 | 3564 | A-109605 | 220 | uGfcAfcAfcAfgAfgAfaggAfcAfgAfcCfcsAfsa |
| AD-53814 | A-110687 | 221 | GfgUfcUfuCfuCfuUfcUfgUfuGfuUfgCfL96 | 3565 | A-109529 | 222 | aGfgCfaAfcAfcAfgAfgaGfaAfgAfcCfcsCfsa |
| AD-53820 | A-110688 | 223 | GfuCfuUfcUfcUfuCfuGfuUfgUfgCfCfL96 | 3566 | A-109531 | 224 | aAfgGfcAfaCfaGfagaGfaAfgAfcCfcsCfsc |
| AD-53825 | A-110689 | 225 | UfcUfuCfuCfuUfcUfgUfuGfuGfcCfuUfL96 | 3567 | A-109533 | 226 | aAfaGfgCfaAfcAfcAfgagAfgAfaGfaCfsCfsc |
| AD-53831 | A-110690 | 227 | CfuUfcUfcUfuCfuGfuUfgUfgCfcUfuUfL96 | 3568 | A-109535 | 228 | aAfaAfgGfcAfaCfagaGfaGfaAfgAfcsCfsc |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-53791 | A-110691 | 229 | UfgUfcCfuCfuCfUfGfuUfgCfcUfuUfuUfL96 | 3569 | A-109537 | 230 | aAfaAfaGfgCfaAfcagAfgAfgGfaCfasGfsa |
| AD-53797 | A-110692 | 231 | GfuCfCfUfcUfGfUfGfUfGfUfuGfcCfuUfuAfL96 | 3570 | A-109539 | 232 | uAfaAfaAfgGfcAfacaGfaGfaGfaAfcsAfsg |
| AD-58902 | | 233 | UfsusUfcFuAfgAfcCfCfUfgUfuUfuGfCfuUfL96 | 3597 | | 234 | asAfsgCfaAfaAfaAfcAfggUfcUfaUfaAfasgsu |
| AD-53803 | A-110693 | 235 | UfUfUfcFuAfaGfaCfcCfUfgUfuUfuGfcUfuUfL96 | 3600 | A-109541 | 236 | aAfaGfCfAfaAfaCfaCfaggUfcUfaGfaAfasAfsg |
| AD-59232 | | 237 | CfsusAfgAfcCfuGfUfUfUfuGfcUfuUfgUfL96 | 3600 | | 238 | PasCfsaAfaAfgCfaAfaacAfgGfuCfuAfgsasa |
| AD-59212 | | 239 | CfsusAfgAfcCfuGfUfUfUfuGfcUfuUfgUfL96 | 3600 | | 240 | PasCfsaAfaAfsgCfaAfaacAfgGfuCfsuAfgsasa |
| AD-53809 | A-110694 | 241 | UfuCfuAfgAfcCfUfGfUfuUfuGfCfuUfuUfgUfL96 | 3601 | A-109543 | 242 | aAfaAfgCfaAfaAfcagGfuCfuAfgAfasAfsa |
| AD-53815 | | 243 | CfuAfgAfcCfuGfUfUfUfuGfcCfuUfuUfgUfL96 | 3601 | | 244 | aCfaAfaAfgCfaAfaacAfgGfuCfuAfgsAfsa |
| AD-579280 | | 245 | CfsusAfgAfcCfuGfUfUfUfuGfcUfuUfgUfL96 | 3601 | | 246 | asCfsaAfaAfgCfaAfaAfgCfaAfaacAfgGfuCfuAfgsasa |
| AD-59182 | | 247 | CfsusAfgAfcCfuGfUfUfUfuugCfuuuuguL96 | 3601 | | 248 | asCfsaAfaAfgCfaAfaacAfgGfuCfuAfgsasa |
| AD-59184 | | 249 | CfsusAfgAfcCfuGfuUfuugCfuuuuguL96 | 3601 | | 250 | asCfsaAfaAfgCfaAfaacAfgGfuCfuAfgsasa |
| AD-59186 | | 251 | CfsusAfgAfcCfuGfUfuugCfuuuuguL96 | 3601 | | 252 | asCfsaAfaAfgCfaAfaacAfgGfuCfuAfgsasa |
| AD-59171 | | 253 | CfsusAfgAfcCfuGfuGfuuugCfuuuuguL96 | 3601 | | 254 | asCfsaAfaAfgCfaAfaacAfgGfuCfuAfgsasa |
| AD-59176 | | 255 | CfsusagaccfugfuuuugcfuuuuguL96 | 3601 | | 256 | asCfsaAfaAfgCfaAfaAfgCfaAfaacAfgGfuCfuAfgsasa |
| AD-59170 | | 257 | CfsusagacCfuGfuuuugCfuuuuguL96 | 3601 | | 258 | asCfsaAfaAfgCfaAfaAfcAfgGfuCfuAfgsasa |
| AD-59175 | | 259 | CfsusagacCfuGfuuuugcuuuuguL96 | 3601 | | 260 | asCfsaAfaAfgCfaAfaAfcAfgGfuCfuAfgsasa |
| AD-59179 | | 261 | csusagaccCfuGfuuuugcuuuuguL96 | 3601 | | 262 | asCfsaAfaAfgCfaAfaAfcAfgGfuCfuAfgsasa |
| AD-59218 | | 263 | CfsusAfgAfcCfuGfuuuugCfuuuuguL96 | 3601 | | 264 | asCfsaAfaAfgCfaAfaAfcAfgGfuCfuAfgsasa |
| AD-59222 | | 265 | CfsusAfgAfcCfuGfuuuugcuuuuguL96 | 3601 | | 266 | asCfsaAfaAfgCfaAfaAfcAfgGfuCfuAfgsasa |
| AD-59226 | | 267 | CfsusagacCfuGfuuuugCfuuuuguL96 | 3601 | | 268 | asCfsaAfaAfgCfaAfaAfcAfgGfuCfuAfgsasa |
| AD-59230 | | 269 | CfsusagacCfuGfuuuugcuuuuguL96 | 3601 | | 270 | asCfsaAfaAfgCfaAfaAfcAfgGfuCfuAfgsasa |
| AD-59235 | | 271 | csusagacCfuGfuuuugcuuuuguL96 | 3601 | | 272 | asCfsaAfaAfgCfaAfaAfcAfgGfuCfuAfgsasa |
| AD-59207 | | 273 | CfsusAfgAfcCfuGfuuuugCfuuuugagguL96 | 3601 | | 274 | asCfsaAfaAfgCfaAfaAfcAfgGfuCfuAfguagsasa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-59211 | | 275 | CfsusAfgAfccCfuGfuuuugcuuuuguL96 | 3601 | | 276 | asCfsaAfAfAfgCfaAfaAfcAfgGfuCfuagsasa |
| AD-59215 | | 277 | CfsusagacCfuGfuuuugCfuuuuguL96 | 3601 | | 278 | asCfsaAfAfAfgCfaAfaAfcAfgGfuCfuagsasa |
| AD-59219 | | 279 | CfsusagacCfuGfuuuugcuuuuguL96 | 3601 | | 280 | asCfsaAfAfAfgCfaAfaAfcAfgGfuCfuagsasa |
| AD-59223 | | 281 | csusagacCfuGfuuuugcuuuuguL96 | 3601 | | 282 | asCfsaAfAfAfgCfaAfaAfcAfgGfuCfuagsasa |
| AD-59181 | | 283 | CfsusAfgAfcCfuGfUfUfgCfuUfgsUfL96 | 3601 | | 284 | asCfsaAfAfAfgCfaAfaCfgGfuCfuAfgsasa |
| AD-59172 | | 285 | CfsusAfgAfcCfuGfUfUfgCfuUfgsgsUfL96 | 3601 | | 286 | asCfsaAfAfAfgCfaAfaAfcAfgGfuCfuAfgsasa |
| AD-59177 | | 287 | CfsusAfgAfcCfuGfUfUfgCfsaUfsuUfsgsUfL96 | 3601 | | 288 | asCfsaAfAfAfgCfaAfaAfcAfgGfuCfuAfgsasa |
| AD-59180 | | 289 | CfsusAfgAfcCfuGfUfUfgCfuUfsuUfsgsUfsL96 | 3601 | | 290 | asCfsaAfAfAfgCfaAfaAfcAfgGfuCfuAfgsasa |
| AD-59183 | | 291 | CfsusAfgAfcCfuGfUfUfgCfuUfgfuUfsgsUfL96 | 3601 | | 292 | asCfsaAfAfAfgCfaAfaAfcAfgGfuCfuAfgsasa |
| AD-59185 | | 293 | CfsusAfgAfcCfuGfUfUfgCfsUfgsUfsL96 | 3601 | | 294 | asCfsaAfAfAfgCfaAfaAfcAfgGfuCfuAfgsasa |
| AD-59173 | | 295 | CfsusAfgAfcCfuGfUfUfgCfuuuuguL96 | 3601 | | 296 | asCfsaAfAfAfgCfaAfaAfcAfgGfuCfuAfgsasa |
| AD-59236 | | 297 | CfsusAfgAfcCfuGfUfUfgCfuUfgCfuUfgsUfL96 | 3601 | | 298 | asCfsaAfAfAfsgCfaAfaacAfgGfuCfuAfgsasa |
| AD-59216 | | 299 | CfsusAfgAfcCfuGfUfUfgCfuUfgCfuUfgsUfL96 | 3601 | | 300 | asCfsaAfAfAfsgCfaAfaacAfgGfuCfuAfgsasa |
| AD-59220 | | 301 | CfsusAfgAfcCfuGfUfUfgCfuUfgCfsuUfsgsUfL96 | 3601 | | 302 | asCfsaAfAfAfsgCfaAfaacAfgGfuCfuAfgsasa |
| AD-59224 | | 303 | CfsusAfgAfcCfuGfUfUfgCfuUfgCfsuUfsuUfsgsUfL96 | 3601 | | 304 | asCfsaAfAfAfsgCfaAfaacAfgGfuCfuAfgsasa |
| AD-59228 | | 305 | CfsusAfgAfcCfuGfUfUfgCfsuUfgCfsuUfsuUfsgsUfsL96 | 3601 | | 306 | asCfsaAfAfAfsgCfaAfaacAfgGfuCfuAfgsasa |
| AD-59233 | | 307 | CfsusAfgAfcCfuGfUfUfgCfuUfgCfuUfgsUfsL96 | 3601 | | 308 | asCfsaAfAfAfsgCfaAfaacAfgGfuCfuAfgsasa |
| AD-59237 | | 309 | CfsusAfgAfcCfuGfUfuugCfuuuugsuL96 | 3601 | | 310 | asCfsaAfAfAfsgCfaAfaacAfgGfuCfuAfgsasa |
| AD-59209 | | 311 | CfsusAfgAfcCfuGfUfUfgCfuUfsugsuL96 | 3601 | | 312 | asCfsaAfAfAfsgCfaAfaacAfgGfuCfuAfgsasa |
| AD-59208 | | 313 | CfsusAfgAfcCfuGfUfUfgCfuUfgsUfL96 | 3601 | | 314 | asCfsaAfAfAfsgCfaAfaacAfgGfsusAfgsasa |
| AD-59210 | | 315 | csusAGAccuGuuuuGsL96 | 3601 | | 316 | AscsAAAAGcAAAAcAGGucuAGsasa |
| AD-59227 | | 317 | CfsusAfGfAfccuGfuuuuuGfcuuuuGfuL96 | 3601 | | 318 | asCfsAfAfAfAfGfcAfAfAfAfcAfGfGfucuAfGfsasa |
| AD-59231 | | 319 | CfsusAfgAfccuGfuuuuGfcuuuuGfuL96 | 3601 | | 320 | asCfsAfAfAfAfGfcAfAfaacAfGfGfucuAfGfsasa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-59198 | | 321 | (C3m)usAfgAfccCfugUfuUfgCfuUfuUfgUfL96 | 3601 | | 322 | asCfsaAfaAfgCfaAfaacAfgGfuCfuAfgsasa |
| AD-59200 | | 323 | (C3m)(U3m)AfgAfccCfugUfuUfgCfuUfuUfgUfL96 | 3601 | | 324 | asCfsaAfaAfgCfaAfaacAfgGfuCfuAfgsasa |
| AD-59203 | | 325 | (m5Cam)usAfgAfccCfugUfuUfgCfuUfuUfgUfL96 | 3601 | | 326 | asCfsaAfaAfgCfaAfaacAfgGfuCfuAfgsasa |
| AD-59204 | | 327 | (m5Cam)(Tam)AfgAfccCfugUfuUfgCfuUfuUfgUfL96 | 3601 | | 328 | asCfsaAfaAfgCfaAfaacAfgGfuCfuAfgsasa |
| AD-59188 | | 329 | (m5Cams)(Tams)AfgAfccCfugUfuUfgCfuUfuUfgUfL96 | 3601 | | 330 | asCfsaAfaAfgCfaAfaacAfgGfuCfuAfgsasa |
| AD-59191 | | 331 | (m5Cams)usAfgAfccCfugUfuUfgCfuUfuUfgUfL96 | 3601 | | 332 | asCfsaAfaAfgCfaAfaacAfgGfuCfuAfgsasa |
| AD-59213 | | 333 | CfsusAfgAfccCfugUfuUfgCfuUfuUfgUfL96 | 3601 | | 334 | asCfsaAfaAfgCfaAfaacAfgGfuCfuAfgs(A3m)a |
| AD-59217 | | 335 | CfsusAfgAfccCfugUfuUfgCfuUfuUfgUfL96 | 3601 | | 336 | asCfsaAfaAfgCfaAfaacAfgGfuCfuAf(G3m)(A3m)a |
| AD-59221 | | 337 | CfsusAfgAfccCfugUfuUfgCfuUfuUfgUfL96 | 3601 | | 338 | asCfsaAfaAfgCfaAfaacAfgGfuCfuAfgs(Aam)a |
| AD-59225 | | 339 | CfsusAfgAfccCfugUfuUfgCfuUfuUfgUfL96 | 3601 | | 340 | asCfsaAfaAfgCfaAfaacAfgGfuCfuAf(Gam)(Aam)a |
| AD-59229 | | 341 | CfsusAfgAfccCfugUfuUfgCfuUfuUfgUfL96 | 3601 | | 342 | asCfsaAfaAfgCfaAfaacAfgGfuCfuAfgs(Aams)a |
| AD-59234 | | 343 | CfsusAfgAfccCfugUfuUfgCfuUfuUfgUfL96 | 3601 | | 344 | asCfsaAfaAfgCfaAfaacAfgGfuCfuAf(Gams)(Aams)a |
| AD-59238 | | 345 | CfsusAfgAfccCfugUfuUfgCfuUfuUfgUfL96 | 3601 | | 346 | (A3m)CfsaAfaAfgCfaAfaacAfgGfuCfuAfgsasa |
| AD-59241 | | 347 | CfsusAfgAfccCfugUfuUfgCfuUfuUfgUfL96 | 3601 | | 348 | as(C3m)aAfaAfgCfaAfaacAfgGfuCfuAfgsasa |
| AD-59245 | | 349 | CfsusAfgAfccCfugUfuUfgCfuUfuUfgUfL96 | 3601 | | 350 | (Aam)CfsaAfaAfgCfaAfaacAfgGfuCfuAfgsasa |
| AD-59250 | | 351 | CfsusAfgAfccCfugUfuUfgCfuUfuUfgUfL96 | 3601 | | 352 | as(mSCam)aAfaAfgCfaAfaacAfgGfuCfuAfgsasa |
| AD-59196 | | 353 | usAfsgAfccCfugUfuUfgCfuUfuUfgUfL96 | 3601 | | 354 | asCfsaAfaAfgCfaAfaacAfgGfuCfuAfgsasa |
| AD-59189 | | 355 | AfsgsAfccCfugUfuUfgCfuUfuUfgUfL96 | 3601 | | 356 | asCfsaAfaAfgCfaAfaacAfgGfuCfuAfgsasa |
| AD-59190 | | 357 | usCfsusAfgAfccCfugUfuUfgCfuUfuUfgUfL96 | 3601 | | 358 | asCfsaAfaAfgCfaAfaacAfgGfuCfuAfgsasa |
| AD-59192 | | 359 | UfsusCfsusAfgAfccCfugUfuUfgCfuUfuUfgUfL96 | 3601 | | 360 | asCfsaAfaAfgCfaAfaacAfgGfuCfuAfgsasa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-59240 | | 361 | CfsusAfgAfcCfuGfuuugCfuuuuguL96 | 3601 | | 362 | asCfsaAfaAfsgCfaAfaacAfgGfuCfuAfgs(A3m)a |
| AD-59244 | | 363 | CfsusAfgAfcCfuGfuuugCfuuuuguL96 | 3601 | | 364 | asCfsaAfaAfsgCfaAfaacAfgGfuCfuAfgsasa |
| AD-59202.7 | | 365 | (C3m)usAfgAfcCfuGfuuugCfuuuuguL96 | 3601 | | 366 | asCfsaAfaAfgCfaAfaacAfgGfuCfuAfgsasa |
| AD-59195 | | 367 | (C3m)usAfgAfcCfuGfuuugCfuuuuguL96 | 3601 | | 368 | asCfsaAfaAfgCfaAfaacAfgGfuCfuAfgsasa |
| AD-59249 | | 369 | CfsusAfgAfcCfuGfUfUfuugCfuuuuguL96 | 3601 | | 370 | asCfsaAfaAfgCfaAfaacAfgGfuCfuAfgs(A3m)a |
| AD-59254 | | 371 | CfsusAfgAfcCfuGfuuugCfuuuuguL96 | 3601 | | 372 | asCfsaAfaAfgCfaAfaacAfgGfuCfuAfgs(A3m)a |
| AD-59259 | | 373 | (C3m)usagaccuguuuugcuuuuguL96 | 3601 | | 374 | asCfsaAfaAfgCfaAfaacAfgGfuCfuAfgs(A3m)a |
| AD-59264 | | 375 | (C3m)usagaccuguuuugcuuuuguL96 | 3601 | | 376 | asCfsaAfaAfgCfaAfaacAfgGfuCfuAfgs(A3m)a |
| AD-59264 | | 377 | (C3m)usagaccuguuuugcuuuuguL96 | 3601 | | 378 | asCfsaAfaAfgCfaAfaacAfgGfuCfuAfgs(A3m)a |
| AD-59255 | | 379 | CsusagaccuGfUfFfuugcuuuuguL96 | 3601 | | 380 | asCfsaAfaAfgCfaAfaacAfgGfuCfuAfgs(A3m)a |
| AD-57928 | | 381 | CfsusAfgAfcCfuGfUfGfuUfuUfgCfuUfuUfgUfL96 | 3601 | | 382 | asCfsaAfaAfgCfaAfaacAfgGfuCfuAfgsasa |
| AD-58893 | | 383 | CfsuAfgAfcCfuGfUfUfuUfuUfgCfuUfuUfgUfL96 | 3601 | | 384 | asCfsaAfaAfgCfaafaacAfgGfuCfuAfgsaa |
| AD-58894 | | 385 | CfusAfgAfcCfuGfUfUfuUfuUfgCfuUfuUfgUfL96 | 3601 | | 386 | aCfsaAfaAfgCfaAfaacAfgGfuCfuAfgsasa |
| AD-58895 | | 387 | CfuAfgAfcCfuGfUfUfuUfuUfgCfuUfuUfgUfL96 | 3601 | | 388 | aCfaAfaAfgCfaAfaacAfgGfuCfuAfga |
| AD-58896 | | 389 | CfsusAfgAfcCfuGfUfUfuUfuUfgCfuUfuUfgUfL96 | 3601 | | 390 | aCfaAfaAfgCfaafaacAfgGfuCfuAfgaa |
| AD-58897 | | 391 | CfsusAfsgAfcCfuGfUfUfuUfuUfgCfuUfuUfgUfL96 | 3601 | | 392 | asCfsasAfaAfgCfaAfaacAfgGfuCfuAfgsasa |
| AD-58898 | | 393 | CfsusAfsgAfcCfuGfUfUfuUfuUfgCfuUfuUfgUfL96 | 3601 | | 394 | asCfsaAfaAfgCfsaAfaacAfsgGfuCfuAfgsasa |
| AD-58899 | | 395 | CfsusAfsgAfcCfuGfUfUfuUfuUfgCfuUfuUfsgUfL96 | 3601 | | 396 | asCfsaAfaAfgCfaAfaacAfsgGfuCfuAfsgsasa |
| AD-53813 | A-110726 | 397 | UfcUfaGfacCfuGfUfUfuUfuGfcUfuUfuUfgUfL96 | 3602 | A-109607 | 398 | aAfaAfaGfcAfaAfacaGfuCfuaGfasAfsa |
| AD-59246 | | 399 | CfsusAfgAfcCfuGfUfUfuUfuUfgCfuUfuUfgUfL96 | 3602 | | 400 | asCfsaAfaAfgCfaAfaacAfgGfuCfuAfsgsa |
| AD-59253 | | 401 | usAfsgAfcCfuGfUfUfuUfuUfgCfuUfuUfgUfL96 | 3602 | | 402 | asCfsaAfaAfgCfaAfaacAfgGfuCfuAfsgsa |
| AD-59242 | | 403 | AfsgsgAfcCfuGfUfUfuUfuUfgCfuUfuUfgUfL96 | 3602 | | 404 | asCfsaAfaAfgCfaAfaacAfgGfuCfuAfsgsa |
| AD-59253 | | 405 | usAfsgsAfcCfuGfUfUfuUfuUfgCfuUfuUfgUfL96 | 3602 | | 406 | asCfsaAfaAfgCfaAfaacAfgGfuCfuAfsgsa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-59258 | A-110695 | 407 | usasgAfcCfuGfUfUfufgCfuUfuUfgUfL96 | 3602 | A-109545 | 408 | asCfsaAfaAfgCfaAfaacAfgGfuCfuAfsgsa |
| AD-53815 | A-110695 | 409 | CfuAfgAfcCfuGfUfUfufgCfuUfuUfgUfL96 | 3603 | A-109545 | 410 | aCfaaAfaAfgCfaAfaacAfgGfuCfuAfgsAfsa |
| AD-53815 | A-110695 | 411 | CfuAfgAfcCfuGfUfUfufgCfuUfuUfgUfL96 | 3603 | A-109545 | 412 | aCfaaAfaAfgCfaAfaacAfgGfuCfuAfgsAfsa |
| AD-53815 | A-110695 | 413 | CfuAfgAfcCfuGfUfUfufgCfuUfuUfgUfL96 | 3603 | A-109545 | 414 | aCfaaAfaAfgCfaAfaacAfgGfuCfuAfgsAfsa |
| AD-56633 | A-115520 | 415 | cuAfgAfcCfuGfUfUfufgCfuUfuUfgUfL96 | 3603 | A-109545 | 416 | aCfaaAfaAfgCfaAfaacAfgGfuCfuAfgsAfsa |
| AD-56617 | A-115535 | 417 | CfuagAfcCfuGfUfUfufgCfuUfuUfgUfL96 | 3603 | A-109545 | 418 | aCfaaAfaAfgCfaAfaacAfgGfuCfuAfgsAfsa |
| AD-56623 | A-115536 | 419 | CfuagAfcCfuGfUfUfufgcuUfuUfguL96 | 3603 | A-109545 | 420 | aCfaaAfaAfgCfaAfaacAfgGfuCfuAfgsAfsa |
| AD-56629 | A-115537 | 421 | CfuagAfccuGfUfUfufuugcuUfuUfgUL96 | 3603 | A-109545 | 422 | aCfaaAfaAfgCfaAfaacAfgGfuCfuAfgsAfsa |
| AD-56635 | A-115538 | 423 | CfuagAfccuGfUfUfuugcuUfuugUfL96 | 3603 | A-109545 | 424 | aCfaaAfaAfgCfaAfaacAfgGfuCfuAfgsAfsa |
| AD-56641 | A-115539 | 425 | CfuagaccuGfUfuugcuuuuguL96 | 3603 | A-109545 | 426 | aCfaaAfaAfgCfaAfaacAfgGfuCfuAfgsAfsa |
| AD-56625 | A-115542 | 427 | CfuAfgAfccuGfUfUfufgCfuUfuUfgUfL96 | 3603 | A-109545 | 428 | aCfaaAfaAfgCfaAfaacAfgGfuCfuAfgsAfsa |
| AD-56631 | A-115543 | 429 | CfuAfgAfAfccfuGfUfUfufgCfuUfuUfgUfL96 | 3603 | A-109545 | 430 | aCfaaAfaAfgCfaAfaacAfgGfuCfuAfgsAfsa |
| AD-56637 | A-115544 | 431 | CfuAfgAfAfcCfuGfUfUfuGfCfuUfuUfgUfL96 | 3603 | A-109545 | 432 | aCfaaAfaAfgCfaAfaacAfgGfuCfuAfgsAfsa |
| AD-56643 | A-115545 | 433 | CfuAfgAfAfcCfuGfUfUfufGfCfuUfuUfgUfL96 | 3603 | A-109545 | 434 | aCfaaAfaAfgCfaAfaacAfgGfuCfuAfgsAfsa |
| AD-56649 | A-115546 | 435 | CfUfUfAfgAfAfcCfuGfUfUfufGfCfuUfuUfgUfL96 | 3603 | A-109545 | 436 | aCfaaAfaAfgCfaAfaacAfgGfuCfuAfgsAfsa |
| AD-56655 | A-115547 | 437 | CfUfUfAfgAfAfcCfuGfUfUfufGfCfUfUfUfUfgUfUfGf UfL96 | 3603 | A-109545 | 438 | aCfaaAfaAfgCfaAfaacAfgGfuCfuAfgsAfsa |
| AD-56615 | A-110695 | 439 | CfuAfgAfcCfuGfUfUfufgCfuUfuUfgUfL96 | 3603 | A-115519 | 440 | acaAfaAfgCfaAfaacAfgGfuCfuAfgsAfsa |
| AD-56621 | A-115520 | 441 | cuAfgAfcCfuGfUfUfufgCfuUfuUfgUfL96 | 3603 | A-115519 | 442 | acaAfaAfgCfaAfaacAfgGfuCfuAfgsAfsa |
| AD-56627 | A-115521 | 443 | cuAfgAfcCfuGfUfUfuugCfuUfuugUfL96 | 3603 | A-115519 | 444 | acaAfaAfgCfaAfaacAfgGfuCfuAfgsAfsa |
| AD-56639 | A-115520 | 445 | cuAfgAfcCfuGfUfUfufgCfuUfuUfgUfL96 | 3603 | A-115522 | 446 | ACfaAfaAfgCfaAfaacAfgGfuCfuAfgsAfsa |
| AD-56645 | A-110695.6 | 447 | CfuAfgAfcCfuGfUfUfufgCfuUfuUfgUfL96 | 3603 | A-115522 | 448 | ACfaAfaAfgCfaAfaacAfgGfuCfuAfgsAfsa |
| AD-56651 | A-115523 | 449 | (iC)uAfgAfcCfuGfUfUfufgCfuUfuUfgUfL96 | 3603 | A-115524 | 450 | (iA)CfaAfaAfgCfaAfaacAfgGfuCfuAfgsAfs(iA) |
| AD-56610 | A-115523 | 451 | (iC)uAfgAfcCfuGfUfUfufgCfuUfuUfgUfL96 | 3603 | A-115525 | 452 | aCfaAfaAfgCfaAfaacAfgGfuCfuAfgsAfs(iA) |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56616 | A-115523 | 453 | (iC)uAfgAfcCfuGfUfUfUfgCfuUfuUfgUfL96 | 3603 | A-115526 | 454 | acaAfaAfgcaAfaacAfgGfuCfuAfgsAfs(iA) |
| AD-56622 | A-115527 | 455 | (iC)uAfgAfcCfuGfUfUfUfgCfuUfuugUfL96 | 3603 | A-115526 | 456 | acaAfaAfgcaAfaacAfgCfuUfaAfgsAfs(iA) |
| AD-56628 | A-115527 | 457 | (iC)uAfgAfcCfuGfUfUfUfgCfuuUfgUfL96 | 3603 | A-115528 | 458 | (iA)caAfaAfgcaAfaacAfgGfuCfuAfgsAfs(iA) |
| AD-56634 | A-115529 | 459 | CbuAfgAfcCfuGfUfUfUfUfgCfuuUfgUfL96 | 3603 | A-115530 | 460 | AbCfaAfaAfgCfaAfaacAfgGfuCfuAfgsAfsAb |
| AD-56640 | A-115529 | 461 | CbuAfgAfcCfuGfUfUfUfUfgCfuUfuUfgUfL96 | 3603 | A-115531 | 462 | aCfaAfaAfgCfaAfaacAfgGfuCfuAfgsAfsAb |
| AD-56646 | A-115529 | 463 | CbuAfgAfcCfuGfUfUfUfUfgCfuuUfgUfL96 | 3603 | A-115532 | 464 | acaAfaAfgcaAfaacAfgGfuCfuAfgsAfsAb |
| AD-56652 | A-115533 | 465 | CbuAfgAfcCfuGfUfUfUfUfgCfuuugUfL96 | 3603 | A-115532 | 466 | acaAfaAfgcaAfaacAfgGfuCfuAfgsAfsAb |
| AD-56611 | A-115533 | 467 | CfuAfgAfcCfuGfUfUfUfUfgCfuUfuUfgUfL96 | 3603 | A-115534 | 468 | (iA)caAfaAfgcaAfaacAfgGfuCfuAfgsAfsAb |
| AD-56647 | A-110695.7 | 469 | CfuagAfcCfuGfUfUfUfUfgCfuuUfgUfL96 | 3603 | A-115540 | 470 | aCfaaaAfgCfaAfaacAfgGfuCfuAfgsasa |
| AD-56653 | A-115535 | 471 | CfuagAfcCfuGfUfUfUfUfgCfuuUfgUfL96 | 3603 | A-115540 | 472 | aCfaaaAfgCfaAfaacAfgGfuCfuAfgsasa |
| AD-56612 | A-115535 | 473 | CfuagAfcCfuGfUfUfUfUfgCfuUfuUfgUfL96 | 3603 | A-115540 | 474 | aCfaaaAfgCfaAfaacAfgGfuCfuAfgsasa |
| AD-56618 | A-115536 | 475 | CfuagAfcCfuGfUfUfUfUfgcuUfuUfgUfL96 | 3603 | A-115540 | 476 | aCfaaaAfgCfaAfaacAfgGfuCfuAfgsasa |
| AD-56624 | A-115537 | 477 | CfuagAfccuGfUfUfUfuugcuUfugUfL96 | 3603 | A-115540 | 478 | aCfaaaAfgCfaAfaacAfgGfuCfuAfgsasa |
| AD-56630 | A-115538 | 479 | CfuagAfccuGfUfUfUfUfuugcuUfugUfL96 | 3603 | A-115540 | 480 | aCfaaaAfgCfaAfaacAfgGfuCfuAfgsasa |
| AD-56636 | A-110695.8 | 481 | CfuAfgAfcCfuGfUfUfUfUfgCfuUfuUfgUfL96 | 3603 | A-115541 | 482 | aCfaaaAfgCfaAfaacAfgCfuAfgsasa |
| AD-56642 | A-115535 | 483 | CfuagAfcCfuGfUfUfUfUfgCfuuUfgUfL96 | 3603 | A-115541 | 484 | aCfaaaAfgCfaAfaacAfgCfuAfgsasa |
| AD-56648 | A-115536 | 485 | CfuagAfcCfuGfUfUfUfUfgcuUfuUfgUfL96 | 3603 | A-115541 | 486 | aCfaaaAfgCfaAfaacAfgCfuAfgsasa |
| AD-56654 | A-115537 | 487 | CfuagAfccuGfUfUfUfUfuUfgcuUfugUfL96 | 3603 | A-115541 | 488 | aCfaaaAfgCfaAfaacAfggCfuAfgsasa |
| AD-56613 | A-115538 | 489 | CfuagAfccuGfUfUfUfuugcuUfugUfL96 | 3603 | A-115541 | 490 | aCfaaaAfgCfaAfaacAfggCfuAfgsasa |
| AD-56619 | A-115539 | 491 | CfuagaccuGfUfUfUfuugcuuugUfL96 | 3603 | A-115541 | 492 | aCfaaaAfgCfaAfaacAfggCfuAfgsasa |
| AD-56614 | A-110695.9 | 493 | CfuAfgAfcCfuGfUfUfUfUfgCfuUfuUfgUfL96 | 3603 | A-115548 | 494 | aCfaAfaAfgCfaAfaacAfgGfUfCfuAfgsAfsa |
| AD-56620 | A-115542 | 495 | CfuAfgAfcCfuGfUfUfUfUfgCfuUfuUfgUfL96 | 3603 | A-115548 | 496 | aCfaAfaAfgCfaAfaacAfgGfUfCfuAfgsAfsa |
| AD-56626 | A-115543 | 497 | CfuAfgAfcCfuGfUfUfUfUfgfCfuUfuUfgUfL96 | 3603 | A-115548 | 498 | aCfaAfaAfgCfaAfaacAfgGfUfCfuAfgsAfsa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56632 | A-115544 | 499 | CfuAfGfAfccCfuGfUfuUfGfCfuUfUfUfgUfL96 | 3603 | A-115548 | 500 | aCfaAfAfAfgCfaAfaacAfgGfUfCfuAfgsAfsa |
| AD-56638 | A-115545 | 501 | CfuAfGfAfCfCfuGfUfUfUfGfCfuUfUfUfGfuUfL96 | 3603 | A-115548 | 502 | aCfaAfAfAfgCfaAfaacAfgGfUfCfuAfgsAfsa |
| AD-56644 | A-115546 | 503 | CfUfAfGfAfCfCfuGfUfuUfGfCfuUfUfUfGfUfL96 | 3603 | A-115548 | 504 | aCfaAfAfAfgCfaAfaacAfgGfUfCfuAfgsAfsa |
| AD-56650 | A-115547 | 505 | CfUfUfAfGfAfCfCfuGfUfUfUfGfCfuUfUfUfGfUfL96 | 3603 | A-115548 | 506 | aCfaAfAfAfgCfaAfaacAfgGfUfCfuAfgsAfsa |
| AD-56656 | A-110695 | 507 | CfuAfGfAfCfCfuGfUfUfUfGfCfuUfUfUfgUfL96 | 3603 | A-115549 | 508 | aCfaAfAfAfGfCfaAfaacAfgGfUfCfuAfgsAfsa |
| AD-56662 | A-115542 | 509 | CfuAfGfAfcCfuGfUfUfuUfGfCfuuUfUfgUfL96 | 3603 | A-115549 | 510 | aCfaAfAfAfGfCfaAfaacAfgGfUfCfuAfgsAfsa |
| AD-56668 | A-115543 | 511 | CfuAfGfAfcCfuGfUfuUfGfCfuUfUfUfgUfL96 | 3603 | A-115549 | 512 | aCfaAfAfAfGfCfaAfaacAfgGfUfCfuAfgsAfsa |
| AD-56673 | A-115544 | 513 | CfuAfGfAfCfCfuGfUfUfUfGfCfuUfUfUfGfuUfL96 | 3603 | A-115549 | 514 | aCfaAfAfAfGfCfaAfaacAfgGfUfCfuAfgsAfsa |
| AD-56678 | A-115545 | 515 | CfuAfGfAfCfCfuGfUfUfUfGfCfuUfUfUfGfuUfL96 | 3603 | A-115549 | 516 | aCfaAfAfAfGfCfaAfaacAfgGfUfCfuAfgsAfsa |
| AD-56683 | A-115546 | 517 | CfuAfGfAfCfCfuGfUfUfuUfGfCfuUfUfUfGfUfL96 | 3603 | A-115549 | 518 | aCfaAfAfAfGfCfaAfaacAfgGfUfCfuAfgsAfsa |
| AD-56688 | A-115547 | 519 | CfUfUfAfGfAfCfCfuGfUfUfUfGfCfuUfUfUfGfUfL96 | 3603 | A-115549 | 520 | aCfaAfAfAfGfCfaAfaacAfgGfUfCfuAfgsAfsa |
| AD-56657 | A-115550 | 521 | CfuAfGfafcCfuGfUfUfuUfGfuugUfL96 | 3603 | A-115551 | 522 | aCfaAfAfAfgCfaAfaacAfgGfuCffuAfgsAfsa |
| AD-56663 | A-115552 | 523 | CfuAfGfafcCfuGfUfUfUfGfCfuuuUfgUfL96 | 3603 | A-115553 | 524 | aCfaAfAfAfgCfaAfaacAfgGfuCfuAfgsAfsa |
| AD-56669 | A-115554 | 525 | CfuAfGfafcCfuGfUfuUfgcuUfuUfGfuUfL96 | 3603 | A-115555 | 526 | aCfaAfAfAfgCfaAfaacAfgGfuCfuAfgsAfsa |
| AD-56674 | A-115556 | 527 | CfuAfGfafcCfuGfUfuugCfuUfuUfgUfL96 | 3603 | A-115557 | 528 | aCfaAfAfAfgCfaAfaacAfgGfuCfuAfgsAfsa |
| AD-56679 | A-115558 | 529 | CfuAfGfafccuGfUfUfUfGfCfuUfUfUfgUfL96 | 3603 | A-115559 | 530 | aCfaAfAfAfgCfaAfAfaacAfgGfuCfuAfgsAfsa |
| AD-56684 | A-115560 | 531 | CfuAfGfacCfuGfUfUfuUfGfCfuUfuUfgUfL96 | 3603 | A-115561 | 532 | aCfaAfAfAfgCfaAfaacAfgGfuCfuAfgsAfsa |
| AD-56689 | A-115535 | 533 | CfuagAfcCfuGfUfUfuUfGfCfuUfUfUfgUfL96 | 3603 | A-115562 | 534 | aCfaAfAfAfgCfaAfaacAfgGfuCfuAfgsAfsa |
| AD-56693 | A-115520 | 535 | cuAfGfAfcCfuGfUfUfuUfGfCfuUfuUfgUfL96 | 3603 | A-115563 | 536 | aCfaAfAfAfgCfaAfaacAfgGfuCfuAfgsAfsa |
| AD-56658 | A-115564 | 537 | CfuAfGfAfcCfuGfUfUfUfGfCfuUfuUfgUfL96 | 3603 | A-115565 | 538 | aCfaaaAfgCfaAfaacAfgGfuCfuAfgsAfsa |
| AD-56664 | A-115566 | 539 | CfuAfGfAfcCfuGfUfUfuUfGfCfuUfuUfgUfL96 | 3603 | A-115567 | 540 | aCfaAfaagCfaAfaacAfgGfuCfuAfgsAfsa |
| AD-56670 | A-115568 | 541 | CfuAfGfAfcCfuGfUfuUfGfCfuUfuUfgUfL96 | 3603 | A-115569 | 542 | aCfaAfAfAfgcaAfaacAfgGfuCfuAfgsAfsa |
| AD-56680 | A-115572 | 543 | CfuAfGfAfcCfuGfUfuUfGfCfuUfuUfgUfL96 | 3603 | A-115573 | 544 | aCfaAfAfAfgCfaAfaacagGfuCfuAfgsAfsa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56685 | A-115574 | 545 | CfuAfgAfcCfuGfUfUfufgCfuUfuUfgUfL96 | 3603 | A-115575 | 546 | aCfaAfaAfgCfaAfaacAfggUfCfuAfgsAfsa |
| AD-56690 | A-115542 | 547 | CfuAfgGfAfcCfuGfUfUfufugCfuUfuUfgUfL96 | 3603 | A-115576 | 548 | aCfaAfaAfgCfaAfaacAfgGfucuAfgsAfsa |
| AD-56694 | A-115577 | 549 | CfuFfAfgAfcCfuGfUfUfufuGfcuUfuUfgUfL96 | 3603 | A-115578 | 550 | aCfaAfaAfgCfaAfaacAfgGfuCfuagsAfsa |
| AD-56659 | A-110695 | 551 | CfuAfgAfcCfuGfUfUfUfufuCfuUfuUfgUfL96 | 3603 | A-115579 | 552 | aCfaAfaAfgCfaAfaacAfgGfuCfuAfgsasa |
| AD-59214 |  | 553 | AsGsAccuGuuuuGcuuuuGuL96 | 3603 |  | 554 | AscsAAAgCaAAAcAGGucusAsG |
| AD-59251 |  | 555 | CfsusAfgAfcCfuGfUfUfUfufgCfuUfuUfgUfL96 | 3603 |  | 556 | asCfsaAfaAfgCfaAfaacAfgGfuCfusAfsg |
| AD-59261 |  | 557 | AfsgsAfcCfugGfUfUfUfufgCfuUfuUfgUfL96 | 3603 |  | 558 | asCfsaAfaAfgCfaAfaacAfgGfuCfusasg |
| AD-59262 |  | 559 | usAfsgAfcCfuGfUfUfUfufugCfuUfuUfgUfL96 | 3603 |  | 560 | asCfsaAfaAfgCfaAfaacAfgGfuCfusasg |
| AD-59265 |  | 561 | csusAfgAfcCfuGfUfUfUfufugCfuUfuUfgUfL96 | 3603 |  | 562 | asCfsaAfaAfgCfaAfaacAfgGfuCfusasg |
| AD-53821 |  | 563 | UfaGfaCfcUfgUfUfUfuGfcUfuUfuGfuAfL96 | 3604 | A-109547 | 564 | uAfcAfaAfaAfgCfcAfaaaCfaGfuCfUfasGfsa |
| AD-59256 |  | 565 | usAfsgAfcCfuGfUfUfUfufgCfuUfuUfgUfL96 | 3604 |  | 566 | asCfsaAfaAfgCfaAfaacAfgGfuCfsusAf |
| AD-59247 |  | 567 | gsAfsgCfcCfugGfUfUfUfufgCfuUfuUfgUfL96 | 3604 |  | 568 | asCfsaAfaAfgCfaAfaacAfgGfuCfsusa |
| AD-59252 |  | 569 | AfsgsAfcCfuGfUfUfUfufuGfcUfuUfgUfL96 | 3604 |  | 570 | asCfsaAfaAfgCfaAfaacAfgGfuCfsusa |
| AD-59257 |  | 571 | usAfsgAfcCfuGfUfUfUfufgCfuUfuUfgUfL96 | 3604 |  | 572 | asCfsaAfaAfgCfaAfaacAfgGfuCfsusa |
| AD-56665 | A-115580 | 573 | AfgAfcCfugGfUfUfUfufgCfuUfuUfgUfL96 | 3605 | A-115581 | 574 | aCfAfaAfaAfgCfaAfaacAfgGfuCfusAfsg |
| AD-56671 | A-115582 | 575 | AfgAfcCfugGfUfUfUfufgCfuUfuUfgUfL96 | 3605 | A-115583 | 576 | aCfAfaAfaAfgCfaAfaacAfgGfuCfusAfsg |
| AD-56676 | A-115584 | 577 | AfgAfcCfugGfUfUfUfufgCfuuuUfgUfL96 | 3605 | A-115585 | 578 | aCfAfaAfaAfgCfaAfaacAfgGfuCfusAfsg |
| AD-56681 | A-115586 | 579 | AfgAfcCfugGfUfUfUfufgcuUfuUfgUfL96 | 3605 | A-115587 | 580 | aCfAfaAfaAfgCfaAfaacAfgGfuCfusAfsg |
| AD-56686 | A-115588 | 581 | AfgAfcCfugGfUfUfUfufugCfuUfuUfgUfL96 | 3605 | A-115589 | 582 | aCfAfaAfaAfgCfaAfaacAfgGfuCfusAfsg |
| AD-56691 | A-115590 | 583 | AfgAfccuGfUfUfUfufugCfuUfuUfgUfL96 | 3605 | A-115591 | 584 | aCfAfaAfaAfgCfaAfaacAfgGfuCfusAfsg |
| AD-56695 | A-115592 | 585 | AfgacCfugGfUfUfUfufugCfuUfuUfgUfL96 | 3605 | A-115593 | 586 | aCfAfaAfaAfgCfaAfaacAfgGfUfCfusAfsg |
| AD-56660 | A-115594 | 587 | agAfcCfuGfUfUfUfufugCfuUfuUfgUfL96 | 3605 | A-115595 | 588 | aCfAfaAfaAfgCfaAfaacAfgGfuCfUfsAfsg |
| AD-56666 | A-115596 | 589 | AfgAfcCfugGfUfUfUfufuUfgUfgUfL96 | 3605 | A-115597 | 590 | aCfaaaAfgCfaAfaacAfgGfucfusAfsg |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-56672 | A-115598 | 591 | AfgAfcCfuGfUfUfufgCfUfUfguUfL96 | 3605 | A-115599 | 592 | acCfaAfaagCfaAfaacAfgGfuCfusAfsg |
| AD-56677 | A-115600 | 593 | AfgAfcCfuGfUfUfGfCfUfUfguUfgUfL96 | 3605 | A-115601 | 594 | aCfaAfaAfgCfcaAfaacAfgGfuCfusAfsg |
| AD-56682 | A-115602 | 595 | AfgAfcCfuGfUfUfUfgCfUfUfguUfgUfL96 | 3605 | A-115603 | 596 | aCfaAfaAfgCfaaacAfgGfuCfusAfsg |
| AD-56687 | A-115604 | 597 | AfgAfcCfuGfUfUfUfGfCfuUfguUfgUfL96 | 3605 | A-115605 | 598 | aCfaAfaAfgCfaAfaacagGfuCfusAfsg |
| AD-56692 | A-115606 | 599 | AfgAfCfcCfuGfUfUfUfgCfuUfguUfgUfL96 | 3605 | A-115607 | 600 | aCfaAfaAfgCfaAfaAfaacAfgguCfusAfsg |
| AD-56696 | A-115608 | 601 | AfgFAfcCfuGfUfUfUfgCfuUfguUfgUfL96 | 3605 | A-115609 | 602 | aCfaAfaAfgCfaAfaAfaacAfgGfucusAfsg |
| AD-56661 | A-115580 | 603 | AfgAfcCfuGfUfUfUfgCfuUfuUfgUfL96 | 3605 | A-115610 | 604 | aCfaAfaAfgCfaAfaAfaacAfgGfCfusasg |
| AD-56667 | A-115611 | 605 | gAfcCfuGfUfUfUfgCfuUfgCfuUfgUfL96 | 3605 | A-115612 | 606 | aCfaAfaAfgCfaAfaacAfgGfuCfausa |
| AD-59260 | | 607 | AfsgsAfcCfuGfUfUfUfgCfuUfuUfgCfuUfL96 | 3605 | | 608 | asCfsaAfaAfgCfaAfaacAfgGfuCfsu |
| AD-59248 | | 609 | gsAfscCfuGfUfUfUfgCfuUfuUfgCfuUfL96 | 3605 | | 610 | asCfsaAfaAfgCfaAfaacAfgGfuCfsu |
| AD-53826 | A-110697 | 611 | UfuUfuGfuAfaCfUfUfGfaFaGfaUfuAfcAfaAfasGfsc | 3618 | A-109549 | 612 | aAfaUfaUfCfuCfaagUfuAfcAfaAfasGfsc |
| AD-53832 | A-110698 | 613 | UfuUfgUfaAfcUfUfGfaAfgAfuUfuAfaAfsg | 3619 | A-109551 | 614 | aAfaAfaUfuCfuUfcaaGfuUfaCfaAfasAfsg |
| AD-53792 | A-110699 | 615 | UfuGfuAfaCfuUfGfaAfgAfaUfUfuAfcAfasAfsa | 3620 | A-109553 | 616 | aUfaAfaUfuCfucaAfgUfuAfcAfaAfasAfsa |
| AD-53798 | A-110700 | 617 | UfgUfaAfcUfuGfAfAfgAfaUfaAfuUfL96 | 3621 | A-109555 | 618 | aAfuAfaAfuAfuCfuucAfaGfuUfaCfasAfsa |
| AD-53819 | A-110727 | 619 | GfuAfaCfuUfgAfAfaGfaAfuAfuUfL96 | 3622 | A-117429 | 620 | aAfuAfaAfuAfuCfuuCfaAfgUfuAfcsAfsa |
| AD-579285 | A-117428 | 621 | CfsusAfgAfcCfuGfUfUfUfgCfuUfuUfgUfL96 | 3602 | A-122702 | 622 | asCfsaAfaAfgCfaAfaacAfgGfuCfuAfgsasa |
| AD-60928 | A-122701 | 623 | CfsusAfgAfcCfuGfUfUfUfgCfuUfuUfgUfL96 | 3602 | A-122704 | 624 | usCfsaAfaAfgCfaAfaacAfgGfuCfuAfgsasa |
| AD-60929 | A-122703 | 625 | GfsusAfgAfcCfuGfUfUfUfgCfuUfuUfgUfL96 | 3602 | A-122706 | 626 | asCfsaAfaAfgCfaAfaacAfgGfuCfuAfcsusu |
| AD-60930 | A-122705 | 627 | GfsasAfgAfcCfuGfUfUfUfgCfuUfuUfgUfL96 | 3602 | A-122708 | 628 | asCfsaAfaAfgCfaAfaacAfgGfuCfuUfcsusu |
| AD-60931 | A-122707 | 629 | GfsasUfgAfcCfuGfUfUfUfgCfuUfuUfgUfL96 | 3602 | A-122709 | 630 | asCfsaAfaAfgCfaAfaacAfgGfuCfuUfcsasa |
| AD-60932 | A-122707 | 631 | GfsasUfgAfcCfuGfUfUfUfgCfuUfuUfgUfL96 | 3602 | A-122711 | 632 | asCfsaAfaAfgCfaAfaacAfgGfuCfuAfUfcsasa |
| AD-60933 | A-122710 | 633 | CfsasUfcAfcCfuGfUfUfUfgCfuUfuUfgUfL96 | 3602 | A-122713 | 634 | asCfsaAfaAfgCfaAfaacAfgGfuGfaUfgsasa |
| AD-60934 | A-122712 | 635 | CfsusUfcCfuGfUfUfUfgCfuUfuUfgUfL96 | 3602 | | 636 | asCfsaAfaAfgCfaAfaacAfgGfaGfafgsasa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-60927 | A-122714 | 637 | CfsusAfcUfgCfuGfUfUfufgCfuUfuUfgUfL96 | 3602 | A-122715 | 638 | asCfsaAfaAfgCfaAfaacAfgCfaGfuAfgsasa |
| AD-579285 | A-117428 | 639 | CfsusAfgAfcCfuGfUfUfufgCfuUfuUfgUfL96 | 3602 | A-117429 | 640 | asCfsaAfaAfgCfaAfaacAfgCfuAfgsasa |
| AD-60906 | A-117428 | 641 | CfsusAfgAfcCfuGfUfUfufgCfuUfuUfgUfL96 | 3602 | A-122309 | 642 | asCfsaAfaAfgCf(Ayh)AfaaAfgCfuCfuAfgsasa |
| AD-60907 | A-117428 | 643 | CfsusAfgAfcCfuGfUfUfufgCfuUfuUfgUfL96 | 3602 | A-122310 | 644 | asCfsaAfaAfgCfa(Ayh)aacAfgCfuCfuAfgsasa |
| AD-60908 | A-117428 | 645 | CfsusAfgAfcCfuGfUfUfufgCfuUfuUfgUfL96 | 3602 | A-122311 | 646 | asCfsaAfaAfgCfaAf(Ayh)acAfgCfuCfuAfgsasa |
| AD-60909 | A-117428 | 647 | CfsusAfgAfcCfuGfUfUfufgCfuUfuUfgUfL96 | 3602 | A-122312 | 648 | asCfsaAfaAfgCfaAfa(Ayh)cAfgCfuCfuAfgsasa |
| AD-60910 | A-117428 | 649 | CfsusAfgAfcCfuGfUfUfufgCfuUfuUfgUfL96 | 3602 | A-122313 | 650 | asCfsaAfaAfgCf(Ayh)AfaacAf(Gyh)GfuCf(Uyh)Afgsasa |
| AD-60911 | A-122307 | 651 | Cfsus(Ayh)(Gyh)(Ayh)(Cyh)CfuGfUfUfuf(Gyh)Cf(Uyh)Uf(Uyh)Uf(Gyh)UfL96 | 3602 | A-117429 | 652 | asCfsaAfaAfgCfaAfaacAfgCfuAfgsasa |
| AD-60912 | A-122308 | 653 | (Cyh)u(Ayh)(Gyh)(Ayh)(Cyh)CfuGfUfUfuf(Gyh)Cf(Uyh)Uf(Uyh)Uf(Gyh)UfL96 | 3602 | A-117429 | 654 | asCfsaAfaAfgCfaAfaacAfgCfuAfgsasa |
| AD-60913 | A-122307 | 655 | Cfsus(Ayh)(Gyh)(Ayh)(Cyh)CfuGfUfUfuf(Gyh)Cf(Uyh)Uf(Uyh)Uf(Gyh)UfL96 | 3602 | A-122309 | 656 | asCfsaAfaAfgCf(Ayh)AfaaAfgCfuCfuAfgsasa |
| AD-60914 | A-122307 | 657 | Cfsus(Ayh)(Gyh)(Ayh)(Cyh)CfuGfUfUfuf(Gyh)Cf(Uyh)Uf(Uyh)Uf(Gyh)UfL96 | 3602 | A-122310 | 658 | asCfsaAfaAfgCfa(Ayh)aacAfgCfuCfuAfgsasa |
| AD-60915 | A-122307 | 659 | Cfsus(Ayh)(Gyh)(Ayh)(Cyh)CfuGfUfUfuf(Gyh)Cf(Uyh)Uf(Uyh)Uf(Gyh)UfL96 | 3602 | A-122311 | 660 | asCfsaAfaAfgCfaAf(Ayh)acAfgCfuCfuAfgsasa |
| AD-579285 | A-117428 | 661 | CfsusAfgAfcCfuGfUfUfufgCfuUfuUfgUfL96 | 3602 | A-122312 | 662 | asCfsaAfaAfgCfaAfa(Ayh)cAfgCfuCfuAfgsasa |
| AD-60916 | A-122307 | 663 | Cfsus(Ayh)(Gyh)(Ayh)(Cyh)CfuGfUfUfuf(Gyh)Cf(Uyh)Uf(Uyh)Uf(Gyh)UfL96 | 3602 | A-122313 | 664 | asCfsaAfaAfgCf(Ayh)AfaacAf(Gyh)GfuCf(Uyh)Afgsasa |
| AD-60917 | A-122307 | 665 | Cfsus(Ayh)(Gyh)(Ayh)(Cyh)CfuGfUfUfuf(Gyh)Cf(Uyh)Uf(Uyh)Uf(Gyh)UfL96 | 3602 | A-122309 | 666 | asCfsaAfaAfgCfaAfaAfgCf(Ayh)AfaacAf(Gyh)GfuCf(Uyh)Afgsasa |
| AD-60918 | A-122308 | 667 | (Cyh)u(Ayh)(Gyh)(Ayh)(Cyh)CfuGfUfUfuf(Gyh)Cf(Uyh)Uf(Uyh)Uf(Gyh)UfL96 | 3602 | A-122312 | 668 | asCfsaAfaAfgCfaAfa(Ayh)cAfgCfuCfuAfgsasa |
| AD-60919 | A-122308 | 669 | (Cyh)u(Ayh)(Gyh)(Ayh)(Cyh)CfuGfUfUfuf(Gyh)Cf(Uyh)Uf(Uyh)Uf(Gyh)UfL96 | 3602 | A-122310 | 670 | asCfsaAfaAfgCfa(Ayh)aacAfgCfuCfuAfgsasa |

TABLE 1-continued

Double-Stranded Ribonucleic Acid (RNAi) Agents Targeting Nucleotides 3544-3623 of Human PCSK9 (SEQ ID NO: 1).

| Duplex ID | Sense ID | SEQ ID NO: | Sense Sequence (5' to 3') | Start In NM_174936.3 | Antisense ID | SEQ ID NO: | Antisense Sequence (5' to 3') |
|---|---|---|---|---|---|---|---|
| AD-60920 | A-122308 | 671 | (Cyh)u(Ayh)(Gyh)(Ayh)(Cyh)CfuGfUfUfuUf(Gyh)Cf(Uyh)Uf(Gyh)UfL96 | 3602 | A-122311 | 672 | asCfsaAfaAfgCfaaAf(Ayh)acAfgGfuCfuAfgsasa |
| AD-60921 | A-122308 | 673 | (Cyh)u(Ayh)(Gyh)(Ayh)(Cyh)CfuGfUfUfuUf(Gyh)Cf(Uyh)Uf(Gyh)UfL96 | 3602 | A-122312 | 674 | asCfsaAfaAfgCfaAfa(Ayh)cAfgGfuCfuAfgsasa |
| AD-60922 | A-122308 | 675 | (Cyh)u(Ayh)(Gyh)(Ayh)(Cyh)CfuGfUfUfuUf(Gyh)Cf(Uyh)Uf(Gyh)UfL96 | 3602 | A-122313 | 676 | asCfsaAfaAfgCf(Ayh)AfaacAf(Gyh)GfuCf(Uyh)Afgsasa |
| AD-58900 | | 677 | CfsasAfgCfaGfaCfAfUfuUfaUfcUfuUfuUfiL96 | 3602 | | 678 | asAfsaAfaGfaUfaAfaugUfcUfgCfuUfgscsu |
| AD-59849 | A-121244 | 679 | CfsusAfgAfcCfuGfUfUfuUfgcuuuuguL96 | 3602 | | 680 | asCfsaAfaagCfaAfaacAfgGfucuAfgsasa |
| AD-60688 | A-120188 | 681 | csusagacCfuGfuuuugcuuuuguL96 | 3602 | | 682 | asCfsaAfaagCfaAfaacAfgGfucuAfgsasa |
| AD-60212 | A-122088 | 683 | csusagacCfugfudTuugcuuuuguL96 | 3602 | | 684 | asCfsaAfAfgCfaAfaAfcAfgGfuCfuagsasa |

Example 2: Phase I Clinical Trial of AD-60212

A Phase I, randomized, single-blind, placebo-controlled study, including, a single ascending dose (SAD) arm and a multi-ascending dose (MAD) arm, was conducted in subjects with elevated low-density lipoprotein cholesterol (LDLc or LDL-C), on or off statins, to evaluate the safety, tolerability, pharmacokinetics and pharmacodynamics of subcutaneously administered AD-60212.

More specifically, in the SAD phase of the study, the ability of a single subcutaneous fixed dose of 25 mg, 100 mg, 300 mg, 500 mg, or 800 mg of AD-60212 (ALN-PCSsc) to lower both PCSK9 protein and LDL-C in healthy volunteer subjects with baseline LDL-C ≥100 mg/dl (≥2.6 mmol/L) and fasting triglycerides <400 mg/dl (<4.5 mmol/L) was tested. In the MAD phase of the study, subjects with LDL-C ≥100 mg/dl, and fasting triglycerides <400 mg/dl (<4.5 mmol/L) on and off of a stable dose of statin for ≥30 days prior to screening were treated with multiple subcutaneous injections of AD-60212 to test the ability of AD-60212 to lower both PCSK9 protein and LDL-C. Subjects in the multiple administration arm of the study were administered a single 125 mg fixed dose of AD-60212 once every week for four weeks (125 mg qW×4), or a single 250 mg fixed dose of AD-60212 once every two weeks for one month (250 mg q2W×2), or a single 300 mg fixed dose of AD-60212 once every month for two months (300 mg qM×2) without statin therapy, or a single 300 mg fixed dose of AD-60212 once every month for two months (300 mg qM×2) with statin therapy, or a single 500 mg fixed dose of AD-60212 once every month for two months (500 mg qM×2) without statin therapy, or a single 500 mg fixed dose of AD-60212 once every month for two months (500 mg qM×2) with statin therapy.

Plasma PCSK9 protein levels were determined using an ELISA assay and serum LDL-C levels were determined directly by β-quantification (Medpace Reference Laboratories, Leuven, Belgium). The levels of total cholesterol, high-density lipoprotein cholesterol (HDL-C), non-HDL-C (total cholesterol minus HDL-C), apolipoprotein B, lipoprotein (a) and triglyceride were also determined.

The cohort demographics and the baseline characteristics of the subjects in the SAD phase of the study are provided in Table 2A and the cohort demographics and the baseline characteristics of the subjects in the MAD phase of the study are provided in Table 2B.

The unmodified sense and antisense sequences of AD-60212 are:

```
Sense-
                                        (SEQ ID NO: 686)
5'-CUAGACCUGUTUUGCUUUUGU-3';
and Antisense-
                                        (SEQ ID NO: 685)
5'-ACAAAAGCAAAACAGGUCUAGAA-3'.
```

The modified sense and antisense sequences of AD-60212 are:

```
Sense-
                                        (SEQ ID NO: 687)
5'-csusagacCfuGfudTuugcuuuugu-3';
and Antisense-
                                        (SEQ ID NO: 688)
5'-asCfsaAfAfAfgCfaAfaAfcAfgGfuCfuagsasa-3'.
```

SAD Phase

AD-60212 was well tolerated at all dose levels in the SAD phase and there were no treatment discontinuations due to adverse events (AEs) and no serious AEs were reported.

Figure 2:
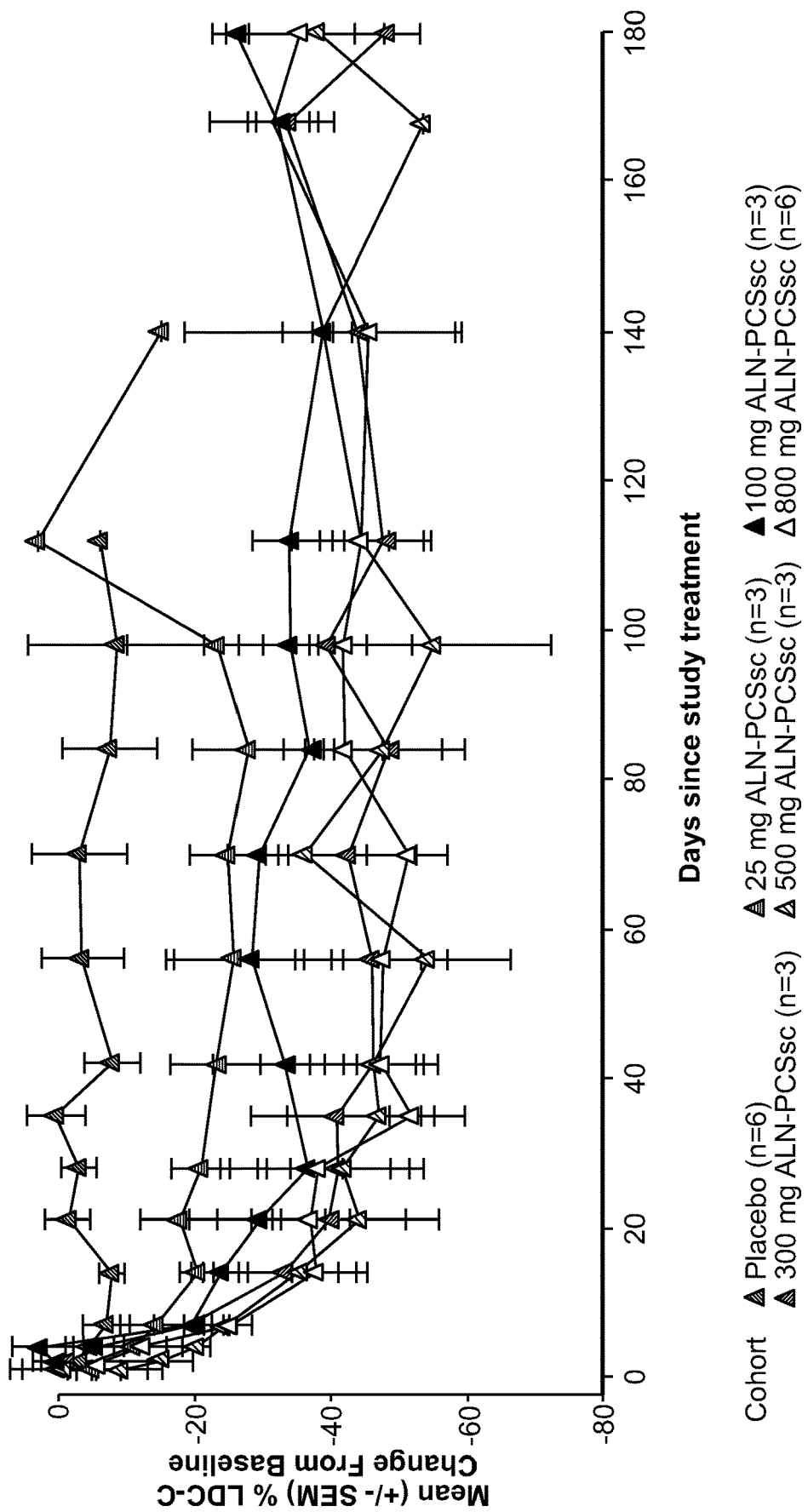
FIG. 2 is a graph showing the lowering of LDL-c levels, shown as a percent mean LCL-C lowering relative to baseline, in subjects receiving a single fixed dose of AD-60212.

The knockdown of PCSK9 protein levels in the single dose cohort, shown as a percent mean PCSK9 knockdown relative to baseline, is shown in FIG. 1, and the lowering of LDL-C levels in the single dose cohort, shown as a percent mean LDL-C lowering relative to baseline, is shown in FIG. 2. Table 3 provides the mean (SD) percent change from baseline in the protein level of PCSK9, the level of LDL-C, the level of total cholesterol, the level of HDL-C, the level of non-HDL-C, the level of apolipoprotein B, the level of triglycerides, and the level of apolipoprotein a at days 84 and 180 post-dose in the SAD phase.

The data demonstrate that administration of AD-60212 reduced PCSK9 levels in a dose-dependent manner up to 300 mg. Doses ≥300 mg produced similar, sustained reductions in PCSK9 levels that were maintained over a period of at least 6 months. PCSK9 levels returned to baseline (mean of last three measurements ≥80% of baseline) by day 180 in the 25-mg and 100-mg dose cohorts. In subjects receiving doses ≥300 mg (n=12), the maximum individual relative reduction from baseline in PCSK9 levels was 89% (800-mg dose, day 112). The mean maximal percent reduction (mean percent reduction at individual nadir) was 82% and was observed in the 800-mg dose cohort. Change from baseline in PCSK9 levels in subjects receiving ALN-PCSsc 300-800 mg (n=2-6 per dose group), was significantly greater than in placebo-treated subjects (P≤0.011) for all 11 measurement points from day 7±1 post-treatment through day 112 post-treatment.

The data further demonstrate that AD-60212 administration resulted in dose-dependent LDL-C reductions up to 300 mg, at which near maximal reductions were achieved. LDL-C reductions were similar across the 300-800 mg dose range. In subjects receiving these doses (n=12), the maximum individual decrease from baseline in LDL-C was 78% (500-mg dose; day 56). The mean maximal and maximal least-squares mean (LSM) percent reductions were 59% and were observed in the 500 and 800-mg cohorts. LDL-C levels returned towards baseline levels by 180 days after the last administration of the 25-mg and 100-mg doses. LDL-C reduction was maintained until at least day 180 after doses ≥300 mg. LDL-C reduction from baseline in subjects receiving ALN-PCSsc 300-800 mg (n=3-6) was statistically significant compared with placebo (P≤0.037) in all 10 determinations from day 14±2 after treatment through day 112 after treatment.

Decreases in total cholesterol, non-HDL-C, apolipoprotein B and lipoprotein (a) concentrations were also noted in AD-60212-treated subjects. Reductions in these parameters were statistically significant compared with placebo for the majority of comparisons.

MAD Phase

AD-60212 was also well tolerated at all dose levels in the MAD phase and there were no treatment discontinuations due to adverse events (AEs) and no serious AEs were reported.

Figure 3:
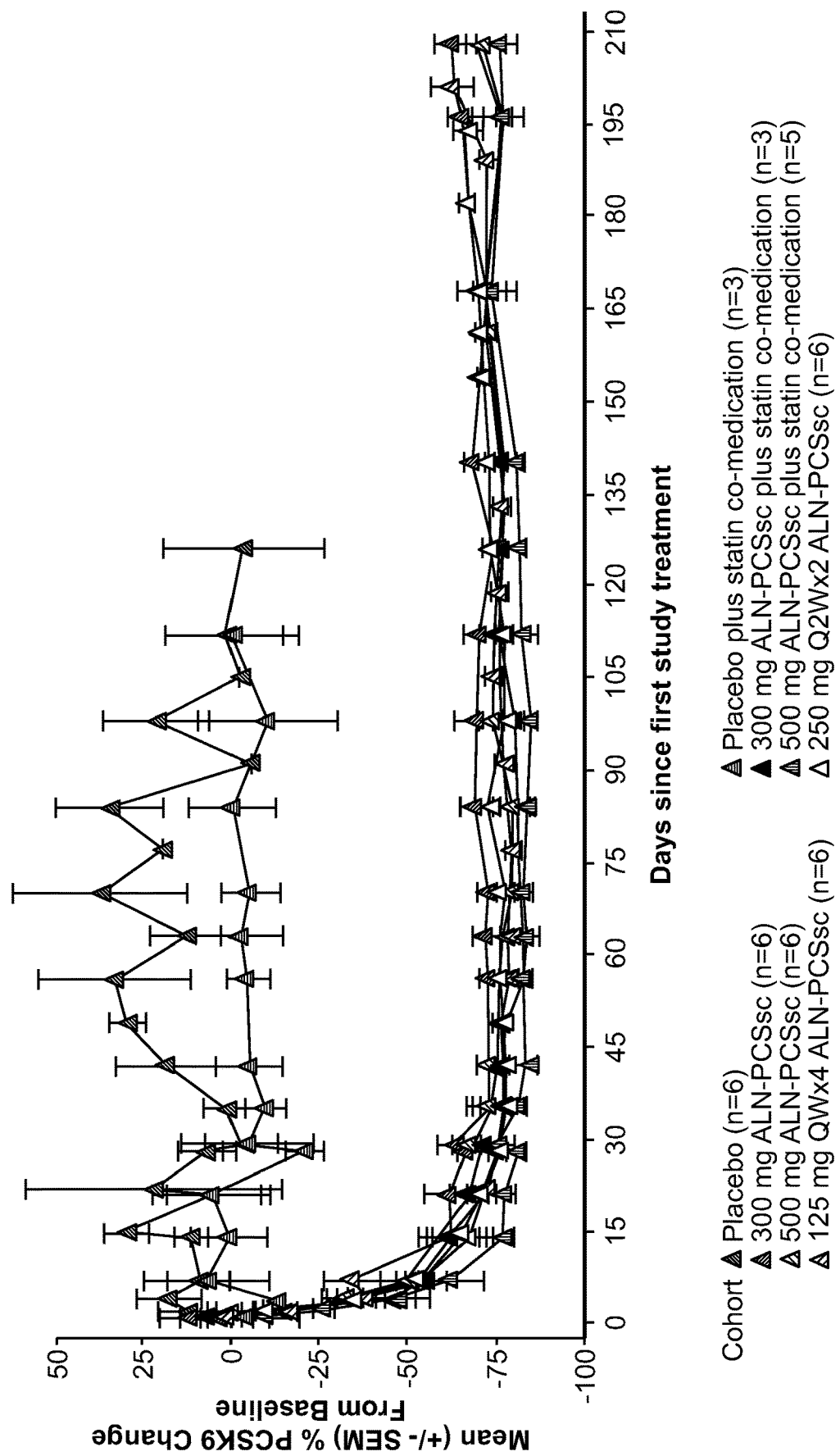
FIG. 3 is a graph showing the knockdown of PCSK9 protein levels, shown as a percent mean PCSK9 knockdown relative to baseline, in subjects receiving multiple fixed doses of AD-60212.
Figure 4:
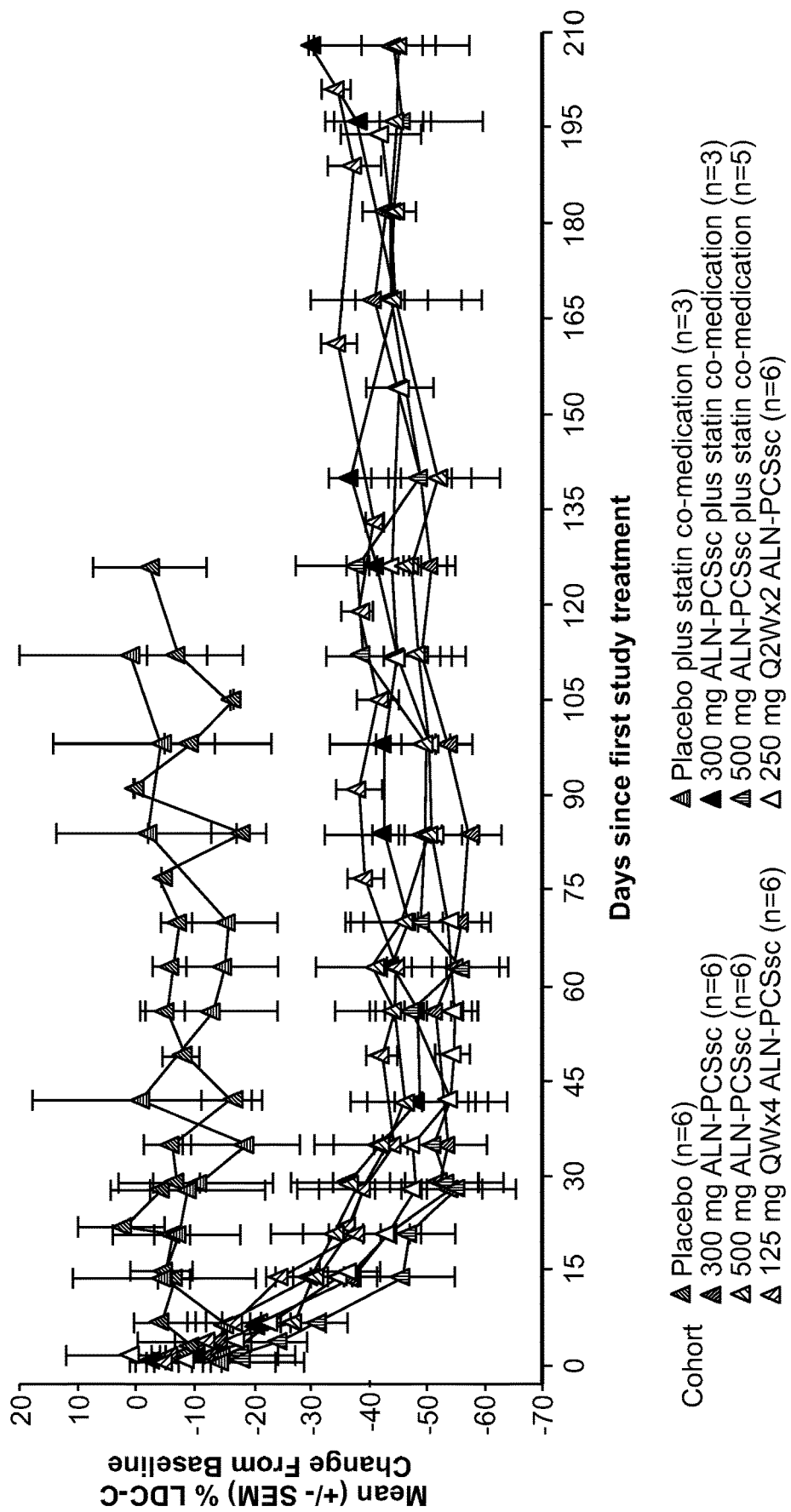
FIG. 4 is a graph showing the lowering of LDL-c levels, shown as a percent mean LCL-C lowering relative to baseline, in subjects receiving multiple fixed doses of AD-60212.

The knockdown of PCSK9 protein levels in the multiple dose cohort, shown as a percent mean PCSK9 knockdown relative to baseline, is shown in FIG. 3, and the lowering of LDL-C levels in the multiple dose cohort, shown as a percent mean LDL-C lowering relative to baseline, is shown in FIG. 4. Table 4 provides the mean (SD) percent change from baseline in the protein level of PCSK9, the level of LDL-C, the level of total cholesterol, the level of HDL-C, the level of non-HDL-C, the level of apolipoprotein B, the level of triglycerides, and the level of apolipoprotein a at days 84 and 180 post-dose in the SAD phase.

The data demonstrate that PCSK9 protein levels were reduced following administration of AD-60212 with all treatment regimens studied. Reductions were similar across all multiple dose cohorts and the reductions were maintained for at least 6 months after the last dose. Consistent with published literature (Khera A V, et al. (2015) *Am J Cardiol* 115:178-82; Guo Y L, et al. (2013) *Clin Drug Investig* 33:877-83), baseline values of PCSK9 were higher in subjects receiving stable doses of statins. Reductions in PCSK9 were independent of baseline PCSK9 levels and similar in subjects irrespective of statin therapy. The maximum individual reduction from baseline in PCSK9 was 94% (500 mg QMx2 co-administered with statin, day 63). The mean maximal percent reduction was 89%, observed in subjects receiving the 500-mg dose co-treated with a statin. Change in PCSK9 concentrations from baseline in subjects receiving multiple doses of AD-60212 as monotherapy (i.e., without statins; n=3-6 per dose group), was significantly greater than placebo (P≤0.002) for all 15 measurement points from day 4 post-treatment through day 126.

The data further demonstrate that similar sustained LDL-C reductions were achieved with all multiple dose AD-60212 treatment regimens. LDL-C reduction was independent of baseline LDL-C levels and similar with and without statin co-therapy. The maximum individual LDL-C reduction was 83% (500 mg QMx2 co-administered with statin, day 29). The mean maximal percent reduction in LDL-C was 64% with a LSM reduction of 60% observed in the cohort receiving the 300-mg dose without statin. LDL-C lowering in all MD cohorts persisted for at least 6 months.

Change in LDL-C from baseline in AD-60212 monotherapy subjects (n=3-6) differed significantly from placebo (P≤0.05) over periods ranging from ~8 to ~17 weeks depending on the treatment regimen.

Decreases in total cholesterol, non-HDL-C, apolipoprotein B and lipoprotein (a) concentrations were also noted in ALN-PCSsc-treated subjects. Reductions in these parameters were statistically significant compared with placebo for the majority of comparisons.

In summary, subcutaneous administration of AD-60212 targeting PCSK9 to reduce LDL-C levels, was well tolerated in single doses of 25 to 800 mg, and in MD regimens of 2-4 doses totaling 500-1000 mg over a 28-day period.

As shown in Figures 1 and 2 and Table 3, a single subcutaneous injection of a fixed dose (≥300 mg of AD-60212) resulted in durable knockdown of PCSK9 and lowering of LDL-C for over 6 months after a single dose. There was up to 89% maximal PCSK9 knockdown, with a mean maximal PCSK9 reduction of 82%, and up to 78% maximal reduction LDL-C lowering, with a mean maximal LDL-C reduction of 59% after administration of a single fixed dose of AD-60212. In addition, LDL-C was significantly (P<0.001) reduced by a mean of 44% at day 140 after a single dose.

As shown in FIGS. 3 and 4 and Table 4, two monthly fixed doses of AD-60212 resulted in up to 94% maximal knockdown of PCSK9, with a mean maximal PCSK9 reduction of 89%, and up to 83% maximal reduction of LDL-C, with a mean maximal LDL-C reduction of 64%, with or without concomitant statin administration.

These data demonstrate that single doses of AD-60212 (≥300 mg) and all multiple doses demonstrated herein were associated with highly sustained reductions of circulating concentrations of both PCSK9 and LDL-C. At these doses, the effect on PCSK9 and LDL-C remained significantly reduced for at least 180 days post-treatment, such that PCSK9 reductions of up to 76%, and LDL-C reductions of up to 48% were still apparent 6 months after the last AD-60212 injection, and demonstrated remarkably little variation over the 6-month post-dose period. Additive serum LDL-C lowering was attained with AD-60212 when added to statin therapy, and the combination therapy did not impact the safety and tolerability of either agent.

In both the SAD and MAD phases, decreases in total cholesterol, non-HDL-C, apolipoprotein B and lipoprotein (a) concentrations were observed in AD-60212-treated subjects. Reductions in these parameters were statistically significant compared with placebo for the majority of comparisons.

TABLE 2A

SAD Cohort Demographics and Baseline Characteristics.

| | Single ascending dose phase | | | | |
| --- | --- | --- | --- | --- | --- |
| | | ALN-PCSsc | | | |
| | Placebo (n = 6) | 25 mg (n = 3) | 100 mg (n = 3) | 300 mg (n = 3) | 500 mg (n = 3) |
| Age, years Mean (SD) | 48 (14.2) | 47 (14.2) | 48 (6.2) | 48 (12.7) | 39 (14.0) |
| Sex, n (%) | | | | | |
| Male | 2 (33.3%) | 3 (100%) | 3 (100%) | 3 (100%) | 3 (100%) |
| Race, n (%) | | | | | |
| White | 4 (66.7%) | 2 (66.7%) | 3 (100%) | 1 (33.3%) | 3 (100%) |
| Black or African American | 2 (33.3%) | 1 (33.3%) | 0 | 1 (33.3%) | 0 |

TABLE 2A-continued

SAD Cohort Demographics and Baseline Characteristics.

| | | | | | |
|---|---|---|---|---|---|
| Asian | 0 | 0 | 0 | 1 (33.3%) | 0 |
| Other | 0 | 0 | 0 | 0 | 0 |
| Body weight, kg Mean (SD) | 70.6 (12.04) | 84.5 (2.11) | 77.3 (6.66) | 81.2 (11.04) | 71.6 (7.93) |
| Height, cm Mean (SD) | 168 (10.6) | 175 (2.3) | 174 (5.1) | 173 (9.6) | 175 (3.1) |
| BMI, kg/m$^2$ Mean (SD) | 24.9 (3.17) | 27.7 (0.21) | 25.5 (2.10) | 27.0 (1.29) | 23.4 (3.01) |
| LDL-C, mmol/L Mean (SD) | 3.4 (0.50) | 4.6 (1.31) | 3.9 (0.92) | 4.2 (0.95) | 3.1 (0.44) |
| TG, mmol/L Mean (SD) | 0.8 (0.14) | 1.3 (0.67) | 2.0 (1.16) | 1.5 (0.55) | 1.8 (0.95) |
| PCSK9, µg/L Mean (SD) | 278.95 (99.53) | 342.65 (67.89) | 233.77 (39.17) | 253.82 (22.36) | 263.23 (24.98) |

| | Single ascending dose phase | | Placebo | |
|---|---|---|---|---|
| | ALN-PCSsc | | With | |
| | 800 mg (n = 6) | Overall (n = 24) | Statin (n = 4) | No Statin (n = 8) |
| Age, years Mean (SD) | 49 (6.7) | 47 (10.7) | 58 (3.0) | 51 (14.2) |
| Sex, n (%) | | | | |
| Male | 5 (83.3%) | 19 (79.2%) | 2 (50.0%) | 6 (75.0%) |
| Race, n (%) | | | | |
| White | 3 (50.0%) | 16 (66.7%) | 4 (100%) | 7 (87.5%) |
| Black or African American | 0 | 4 (16.7%) | 0 | 0 |
| Asian | 1 (16.7%) | 2 (8.3%) | 0 | 0 |
| Other | 2 (33.3%) | 2 (8.3%) | 0 | 1 (12.5%) |
| Body weight, kg Mean (SD) | 74.0 (6.01) | 75.5 (9.16) | 74.3 (5.07) | 77.6 (10.31) |
| Height, cm Mean (SD) | 169 (5.5) | 172 (7.2) | 168 (10.5) | 171 (9.3) |
| BMI, kg/m$^2$ Mean (SD) | 25.9 (1.60) | 25.6 (2.39) | 26.5 (2.72) | 26.7 (2.64) |
| LDL-C, mmol/L Mean (SD) | 4.1 (0.74) | 3.8 (0.85) | 3.7 (2.32) | 3.4 (0.54) |
| TG, mmol/L Mean (SD) | 1.3 (0.24) | 1.4 (0.65) | 1.7 (0.53) | 1.4 (0.43) |

TABLE 2A-continued

SAD Cohort Demographics and Baseline Characteristics.

| | | | | | |
|---|---|---|---|---|---|
| PCSK9, µg/L Mean (SD) | 279.62 (66.90) | 276.32 (68.28) | 460.69 (56.295) | 276.23 (58.69) |

BMI = body mass index;

LDL-C = low-density lipoprotein cholesterol;

PCSK9 = proprotein convertase subtilisin/kexin type 9;

QM × 2 = 2 monthly doses;

QW × 4 = 4 weekly doses;

Q2W × 2 = 2 biweekly doses;

SD = standard deviation;

TG = triglycerides.

To convert values for cholesterol to mg/dL multiply by 38.67.

To convert values for TG to mg/dL multiply by 88.57.

TABLE 2B

MAD Cohort Demographics and Baseline Characteristics.

| | Multiple dose phase | | | | |
|---|---|---|---|---|---|
| | Placebo | | ALN-PCSsc | | |
| | | | 300 mg | 300 mg | 500 mg |
| | With Statin (n = 4) | No Statin (n = 8) | QM × 2 With Statin (n = 4) | QMx × 2 No Statin (n = 6) | QM × 2 With Statin (n = 5) |
| Age, years Mean (SD) | 58 (3.0) | 51 (14.2) | 52 (21.6) | 47 (8.7) | 56 (11.5) |
| Sex, n (%) | | | | | |
| Male | 2 (50.0%) | 6 (75.0%) | 2 (50.0%) | 6 (100%) | 2 (40.0%) |
| Race, n (%) | | | | | |
| White | 4 (100%) | 7 (87.5%) | 3 (75.0%) | 6 (100%) | 3 (60.0%) |
| Black or African American | 0 | 0 | 0 | 0 | 1 (20.0%) |
| Asian | 0 | 0 | 1 (25.0%) | 0 | 1 (20.0%) |
| Other | 0 | 1 (12.5%) | 0 | 0 | 0 |
| Body weight, kg Mean (SD) | 74.3 (5.07) | 77.6 (10.31) | 85.0 (22.04) | 77.8 (15.19) | 71.9 (11.03) |
| Height, cm Mean (SD) | 168 (10.5) | 171 (9.3) | 176 (12.5) | 175 (7.4) | 167 (11.7) |
| BMI, kg/m$^2$ Mean (SD) | 26.5 (2.72) | 26.7 (2.64) | 27.1 (3.59) | 25.2 (2.95) | 25.7 (1.97) |
| LDL-C, mmol/L Mean (SD) | 3.7 (2.32) | 3.4 (0.54) | 3.7 (0.79) | 3.7 (0.52) | 2.7 (0.51) |
| TG, mmol/L Mean (SD) | 1.7 (0.53) | 1.4 (0.43) | 1.5 (0.98) | 1.5 (1.02) | 1.1 (0.50) |
| PCSK9, µg/L Mean (SD) | 460.69 (56.295) | 276.23 (58.69) | 460.69 (209.435) | 311.47 (59.85) | 433.44 (107.28) |

TABLE 2B-continued

MAD Cohort Demographics and Baseline Characteristics.

| | | Multiple dose phase ALN-PCSsc | | | |
|---|---|---|---|---|---|
| | | 500 mg QM × 2 No Statin (n = 6) | 125 mg QW × 4 No Statin (n = 6) | 250 mg Q2W × 2 No Statin (n = 6) | Overall (n = 45) |
| | Age, years Mean (SD) | 42 (16.1) | 55 (9.4) | 61 (6.3) | 52 (12.7) |
| | Sex, n (%) | | | | |
| | Male | 3 (50.0%) | 4 (66.7%) | 4 (66.7%) | 29 (64.4%) |
| | Race, n (%) | | | | |
| | White | 5 (83.3%) | 5 (83.3%) | 3 (50.0%) | 36 (80.0%) |
| | Black or African American | 0 | 0 | 1 (16.7%) | 2 (4.4%) |
| | Asian | 1 (16.7%) | 1 (16.7%) | 0 | 4 (8.9%) |
| | Other | 0 | 0 | 2 (33.3%) | 3 (6.7%) |
| | Body weight, kg Mean (SD) | 64.9 (7.86) | 73.1 (7.07) | 83.2 (8.12) | 75.8 (12.03) |
| | Height, cm Mean (SD) | 168 (5.3) | 167 (6.9) | 176 (10.1) | 171 (9.2) |
| | BMI, kg/m$^2$ Mean (SD) | 23.0 (2.34) | 26.2 (2.72) | 27.0 (1.93) | 25.9 (2.72) |
| | LDL-C, mmol/L Mean (SD) | 3.2 (1.29) | 3.6 (0.48) | 3.8 (0.37) | 3.5 (0.92) |
| | TG, mmol/L Mean (SD) | 1.0 (0.23) | 1.0 (0.29) | 1.8 (0.78) | 1.4 (0.66) |
| | PCSK9, μg/L Mean (SD) | 288.07 (69.07) | 380.03 (50.63) | 288.73 (53.53) | 348.34 (103.99) |

BMI = body mass index;
LDL-C = low-density lipoprotein cholesterol;
PCSK9 = proprotein convertase subtilisin/kexin type 9;
QM × 2 = 2 monthly doses;
QW × 4 = 4 weekly doses;
Q2W × 2 = 2 biweekly doses;
SD = standard deviation;
TG = triglycerides.
To convert values for cholesterol to mg/dL multiply by 38.67.
To convert values for TG to mg/dL multiply by 88.57.

TABLE 3

Mean (SD) percent change from baseline in pharmacodynamic parameters in the SAD phase (Pharmacodynamic population)

| | | ALN-PCSsc | | | | |
|---|---|---|---|---|---|---|
| | Placebo (n = 6) | 25 mg (n = 3) | 100 mg (n = 3) | 300 mg (n = 3) | 500 mg (n = 3) | 800 mg (n = 6) |
| PCSK9 Day 84 | | | | | | |
| n | 5 | 2 | 3 | 3 | 3 | 6 |
| Mean (SD) percent change | −0.1 (14.3) | −47.3 (7.2) | −29.9 (12.9) | −72.6 (12.1) | −68.7 (9.8) | −72.2 (8.5) |
| Day 180 | | | | | | |
| n | NA | NA | 2 | 3 | 2 | 4 |
| Mean (SD) percent change | NA | NA | −15.7 (0.2) | −47.8 (24.8) | −70.3 (6.6) | −74.3 (13.2) |
| Mean (SD) percent change at individual nadir[a] | −29.4 (9.53) | −54.3 (4.75) | −48.9 (27.37) | −77.9 (3.49) | −75.7 (11.75) | −82.3 (4.85) |
| Mean (SD) percent change at group nadir[b] | −17.5 (19.56) | −51.2 (0.56) | −41.7 (21.28) | −74.0 (0.57) | −77.7 (1.28) | −79.4 (3.27) |

TABLE 3-continued

Mean (SD) percent change from baseline in pharmacodynamic parameters in the SAD phase (Pharmacodynamic population)

| | | ALN-PCSsc | | | | |
|---|---|---|---|---|---|---|
| | Placebo (n = 6) | 25 mg (n = 3) | 100 mg (n = 3) | 300 mg (n = 3) | 500 mg (n = 3) | 800 mg (n = 6) |
| Time to group nadir, days | 35 | 42 | 42 | 42 | 112 | 98 |
| LDL-C | | | | | | |
| Day 84 | | | | | | |
| n | 5 | 2 | 3 | 3 | 3 | 5 |
| Mean (SD) percent change | −7.5 (15.6) | −27.9 (11.4) | −36.6 (6.1) | −48.4 (19.0) | −47.6 (15.2) | −41.9 (12.3) |
| Day 180 | | | | | | |
| n | NA | NA | 2 | 3 | 2 | 4 |
| Mean (SD) percent change | NA | NA | −26.3 (2.1) | −47.8 (0.5) | −37.9 (21.7) | −35.2 (16.8) |
| Mean (SD) percent change at individual nadir[a] | −18.7 (5.61) | −34.5 (8.62) | −42.9 (15.35) | −55.0 (10.03) | −55.1 (19.93) | −59.2 (12.25) |
| Mean (SD) percent change at group nadir[b] | −8.6 (18.07) | −27.9 (11.43) | −38.7 (2.07) | −48.4 (18.99) | −55.1 (24.46) | −51.8 (8.44) |
| Time to group nadir, days | 98 | 84 | 140 | 84 | 98 | 35 |
| Total cholesterol | | | | | | |
| Day 84 | −1.3 (11.7) | −20.2 (9.4) | −18.2 (10.7) | −30.9 (9.4) | −24.2 (10.2) | −28.1 (11.7) |
| Day 180 | NA | NA | −14.1 (2.9) | −30.5 (5.7) | −23.5 (11.1) | −25.0 (12.2) |
| HDL-C | | | | | | |
| Day 84 | 11.7 (14.4) | 8.3 (10.3) | 19.6 (17.7) | 50.5 (71.3) | 6.5 (6.4) | 1.9 (17.0) |
| Day 180 | NA | NA | 18.1 (26.3) | 12.8 (42.5) | −2.8 (2.8) | −0.2 (16.4) |
| non-HDL-C | | | | | | |
| Day 84 | −6.6 (12.2) | −25.5 (11.3) | −28.8 (7.5) | −47.2 (19.2) | −34.1 (12.6) | −36.0 (12.6) |
| Day 180 | NA | NA | −21.2 (3.6) | −38.0 (12.6) | −29.5 (13.6) | −30.4 (13.4) |
| Apolipoprotein B | | | | | | |
| Day 84 | −10.0 (15.6) | −18.2 (9.7) | −28.1 (15.6) | −45.5 (20.5) | −36.0 (11.7) | −44.5 (11.8) |
| Day 180 | NA | NA | −30.5 (7.6) | −37.6 (12.2) | −29.2 (18.8) | −27.7 (13.6) |
| Triglycerides | | | | | | |
| Day 84 | −12.4 (7.9) | −9.0 (19.7) | −9.6 (20.2) | −25.1 (29.2) | 15.1 (28.1) | 24.6 (48.2) |
| Day 180 | NA | NA | −18.7 (35.5) | 45.0 (105.8) | −8.6 (10.1) | −7.4 (23.2) |
| Lipoprotein (a) | | | | | | |
| Day 84 | 6.7 (25.7) | −2.8 (29.0) | −20.1 (3.5) | −33.8 (46.7) | −30.4 (27.0) | −22.1 (20.8) |
| Day 180 | NA | NA | 6.6 (23.7) | −37.9 (35.8) | −31.1 (26.7) | −2.5 (18.9) |

HDL-C = high-density lipoprotein cholesterol;
LDL-C = low-density lipoprotein cholesterol;
NA = not applicable;
PCSK9 = proprotein convertase subtilisinikexin type 9;
SD = standard deviation.
[a]Individual nadir values defined as the largest post-dose percent reduction from baseline value per subject. These values were then summarized.
[b]Group nadir is defined as the largest mean post-dose percent change from baseline value during the study.

TABLE 4

Mean (SD) percent change from baseline in pharmacodynamic parameters in the MAD phase (Pharmacodynamic population)

| | Placebo | | ALN-PCSsc | | | | | |
|---|---|---|---|---|---|---|---|---|
| | | | 300 mg QM × 2 | 300 mg QM × 2 | 500 mg QM × 2 | 500 mg QM × 2 | 125 mg QW × 4 | 250 mg Q2W × 2 |
| | With Statin (n = 3) | No Statin (n = 8) | With Statin (n = 3) | No Statin (n = 6) | With Statin (n = 5) | No Statin (n = 6) | No Statin (n = 6) | No Statin (n = 6) |
| PCSK9 | | | | | | | | |
| 84 days after last dose | | | | | | | | |
| n | 3 | 6 | 3 | 6 | 5 | 6 | 6 | 6 |
| Mean (SD) percent change | −0.5 (33.4) | 1.3 (36.7) | −78.1 (3.9) | −70.6 (10.9) | −82.6 (9.5) | −74.2 (8.3) | −75.0 (7.5) | −78.0 (6.8) |
| 180 days after last dose | | | | | | | | |
| n | NA | NA | 1 | 6 | 4 | 6 | 6 | 6 |
| Mean (SD) percent change | NA | NA | −69.7 (NC) | −62.6 (10.7) | −75.9 (10.8) | −72.3 (14.3) | −63.3 (14.5) | −67.4 (9.9) |

TABLE 4-continued

Mean (SD) percent change from baseline in pharmacodynamic parameters in the MAD phase (Pharmacodynamic population)

| | | | ALN-PCSsc | | | | | |
|---|---|---|---|---|---|---|---|---|
| | Placebo | | 300 mg QM × 2 | 300 mg QM × 2 | 500 mg QM × 2 | 500 mg QM × 2 | 125 mg QW × 4 | 250 mg Q2W × 2 |
| | With Statin (n = 3) | No Statin (n = 8) | With Statin (n = 3) | No Statin (n = 6) | With Statin (n = 5) | No Statin (n = 6) | No Statin (n = 6) | No Statin (n = 6) |
| Mean (SD) percent change at individual nadir[a] | −42.4 (3.76) | −25.3 (20.51) | −86.1 (2.06) | −80.4 (4.92) | −88.5 (3.67) | −81.5 (5.73) | −83.8 (2.13) | −82.7 (2.81) |
| Mean (SD) percent change at group nadir[b] | −21.2 (8.9) | −6.1 (NC) | −83.6 (4.06) | −73.1 (6.31) | −85.2 (1.83) | −79.9 (5.35) | −80.3 (4.73) | −79.4 (3.83) |
| Time to group nadir, days | 28 | 91 | 56 | 56 | 84 | 84 | 77 | 35 |
| LDL-C 84 days after last dose | | | | | | | | |
| n | 3 | 5 | 3 | 6 | 5 | 6 | 6 | 6 |
| Mean (SD) percent change | 0.9 (33.3) | −7.0 (11.6) | −44.7 (21.2) | −48.8 (9.0) | −38.9 (13.6) | −48.5 (14.2) | −41.8 (8.8) | −50.0 (10.5) |
| 180 days after last dose | | | | | | | | |
| n | NA | NA | 1 | 6 | 4 | 6 | 6 | 6 |
| Mean (SD) percent change | NA | NA | −30.0 (NC) | −44.3 (12.8) | −44.2 (26.2) | −45.3 (16.1) | −34.5 (5.8) | −42.1 (16.6) |
| Mean (SD) percent change at individual nadir[a] | −27.7 (13.19) | −19.2 (9.68) | −53.8 (19.78) | −64.4 (13.22) | −59.9 (18.14) | −56.2 (14.59) | −52.1 (4.75) | −60.4 (11.02) |
| Mean (SD) percent change at group nadir[b] | −18.4 (17.7) | −16.3 (NC) | −46.7 (18.29) | −55.7 (13.20) | −48.9 (23.77) | −51.9 (14.97) | −44.8 (4.07) | −54.8 (7.77) |
| Time to group nadir, days | 35 | 105 | 70 | 70 | 140 | 140 | 63 | 49 |
| Total cholesterol | | | | | | | | |
| 84 days after last dose | 2.9 (25.1) | −11.8 (11.3) | −24.2 (13.4) | −39.9 (7.4) | −28.6 (16.1) | −25.8 (9.3) | −25.9 (5.4) | −32.0 (7.4) |
| 180 days after last dose | NA | NA | −13.9 (NA) | −26.0 (6.5) | −25.0 (19.6) | −24.2 (12.8) | −22.2 (4.7) | −26.4 (13.9) |
| HDL-C | | | | | | | | |
| 84 days after last dose | 10.6 (11.8) | −2.1 (15.1) | 11.2 (9.4) | 13.5 (15.6) | 5.2 (15.9) | 13.1 (15.9) | 7.3 (3.9) | 7.0 (15.8) |
| 180 days after last dose | NA | NA | 20.5 (NA) | 7.5 (7.7) | 3.8 (10.6) | 6.0 (12.7) | 3.5 (6.5) | 10.2 (11.0) |
| non-HDL-C | | | | | | | | |
| 84 days after last dose | 1.3 (36.5) | −15.1 (11.2) | −35.2 (10.7) | −55.3 (12.7) | −43.4 (19.1) | −43.6 (11.8) | −37.4 (9.6) | −42.5 (9.2) |
| | NA | NA | −25.5 (NA) | −35.5 (8.0) | −36.4 (22.0) | −37.7 (15.4) | −31.1 (4.9) | −36.6 (16.3) |
| Apolipoprotein B | | | | | | | | |
| 84 days after last dose | −6.1 (31.7) | −15.3 (11.0) | −36.8 (9.7) | −51.5 (10.7) | −40.1 (14.0) | −45.3 (11.9) | −36.4 (10.1) | −42.7 (9.9) |
| 180 days after last dose | NA | NA | −24.1 (NA) | −35.1 (10.1) | −34.9 (21.3) | −37.4 (14.8) | −24.4 (3.1) | −36.5 (15.7) |
| Triglycerides | | | | | | | | |
| 84 days after last dose | 1.5 (45.7) | −8.1 (33.8) | −8.8 (6.5) | −39.3 (13.8) | −16.6 (15.2) | −0.1 (24.5) | −7.5 (19.0) | −18.0 (12.0) |
| 180 days after last dose | NA | NA | −13.1 (NA) | 7.4 (37.3) | 7.2 (23.1) | 6.1 (15.8) | −0.7 (28.9) | 21.3 (48.7) |

TABLE 4-continued

Mean (SD) percent change from baseline in pharmacodynamic parameters in the MAD phase (Pharmacodynamic population)

| | Placebo | | ALN-PCSsc | | | | | | |
|---|---|---|---|---|---|---|---|---|---|
| | | | 300 mg QM × 2 | | 300 mg QM × 2 | 500 mg QM × 2 | 500 mg QM × 2 | 125 mg QW × 4 | 250 mg Q2W × 2 |
| | With Statin (n = 3) | No Statin (n = 8) | With Statin (n = 3) | No Statin (n = 6) | With Statin (n = 5) | No Statin (n = 6) | No Statin (n = 6) | No Statin (n = 6) |
| Lipoprotein (a) | | | | | | | | |
| 84 days after last dose | 3.2 (20.9) | −14.7 (18.6) | −17.9 (42.5) | −19.4 (24.9) | −28.9 (28.0) | −27.6 (15.6) | −27.4 (8.9) | −25.3 (12.9) |
| 180 days after last dose | NA | NA | −12.2 (NA) | −15.9 (26.6) | −23.7 (26.4) | −27.7 (23.7) | −29.0 (15.3) | −28.9 (12.6) |

HDL-C = high-density lipoprotein cholesterol;
LDL-C = low-density lipoprotein cholesterol;
NA = not applicable;
NC = not calculated;
PCSK9 = proprotein convertase subtilisin/kexin type 9;
QM × 2 = 2 monthly doses;
QW × 4 = 4 weekly doses;
Q2Wx × 2 = 2 biweekly doses;
SD = standard deviation.
[a]Individual nadir values defined as the largest post-dose percent reduction from baseline value per subject. These values were then summarized.
[b]Group nadir is defined as the largest mean post-dose percent change from baseline value during the study.

I claim:

1. A method of inhibiting the expression of a Proprotein convertase subtilisin kexin 9 (PCSK9) gene in a human subject, comprising subcutaneously administering to the subject a fixed dose of 275 mg to 325 mg of a double stranded ribonucleic acid (RNAi) agent, or salt thereof, wherein the double stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfA-fAfgCfaAfaAfcAfgGfuCfuagsasa-3' (SEQ ID NO: 688), wherein a, g, c and u are 2'-O-methyl (2'-OMe) A, G, C, and U; Af, Gf, Cf and Uf are 2'-fluoro A, G, C and U; dT is 2'-deoxythymidine; and s is a phosphorothioate linkage, and wherein the double stranded RNAi agent is conjugated to a N-acetylgalactosamine (GalNAc)3 ligand.

2. A method of treating a human subject having a hyperlipidemia, comprising subcutaneously administering to the subject a fixed dose of 275 mg to 325 mg of a double stranded ribonucleic acid (RNAi) agent, or salt thereof, wherein the double stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfA-fAfgCfaAfaAfcAfgGfuCfuagsasa-3' (SEQ ID NO: 688), wherein a, g, c and u are 2'-O-methyl (2'-OMe) A, G, C, and U; Af, Gf, Cf and Uf are 2'-fluoro A, G, C and U; dT is 2'-deoxythymidine; and s is a phosphorothioate linkage, and wherein the double stranded RNAi agent is conjugated to a N-acetylgalactosamine (GalNAc)3 ligand.

3. The method of claim 1, wherein the subject is administered a fixed dose of 300 mg.

4. The method of claim 2, wherein the subject is administered a fixed dose of 300 mg.

5. The method of claim 1, wherein the subject is administered a fixed dose of 300 mg once a quarter.

6. The method of claim 2, wherein the subject is administered a fixed dose of 300 mg once a quarter.

7. The method of claim 1, wherein the subject is administered a fixed dose of 300 mg biannually.

8. The method of claim 2, wherein the subject is administered a fixed dose of 300 mg biannually.

9. The method of claim 1, wherein the double stranded RNAi agent or salt thereof is administered to the subject in a dosing regimen that includes a loading phase followed by a maintenance phase.

10. The method of claim 2, wherein the double stranded RNAi agent or salt thereof is administered to the subject in a dosing regimen that includes a loading phase followed by a maintenance phase.

11. The method of claim 9, wherein the dose administered to the subject during the loading phase is the same as the dose administered to the subject during the maintenance phase.

12. The method of claim 10, wherein the dose administered to the subject during the loading phase is the same as the dose administered to the subject during the maintenance phase.

13. The method of claim 1, further comprising administering an additional therapeutic agent to the subject.

14. The method of claim 2, further comprising administering an additional therapeutic agent to the subject.

15. The method of claim 2, wherein the hyperlipidemia is hypercholesterolemia.

16. The method of claim 1, wherein the double stranded RNAi agent or salt thereof is administered in a pharmaceutical composition.

17. The method of claim 2, wherein the double stranded RNAi agent or salt thereof is administered in a pharmaceutical composition.

18. The method of claim 1, wherein the (GalNAc)3 ligand is

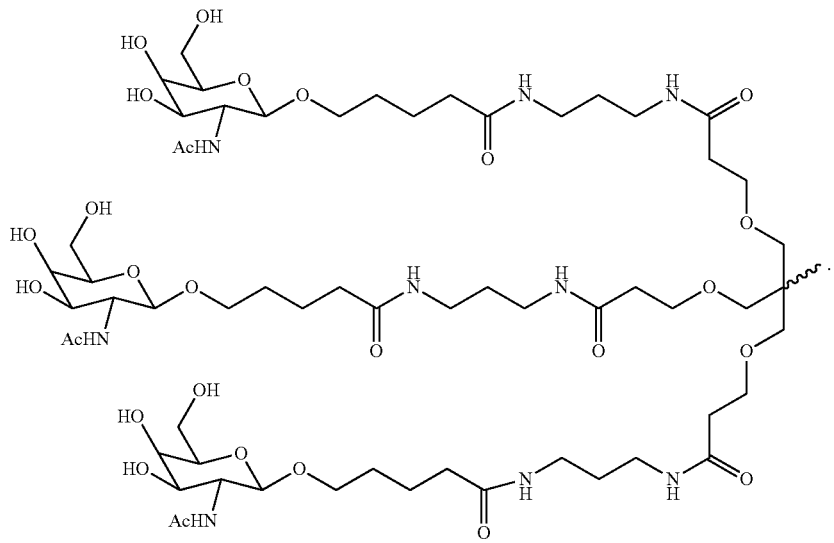 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

19. The method of claim 2, wherein the (GalNAc)3 ligand is

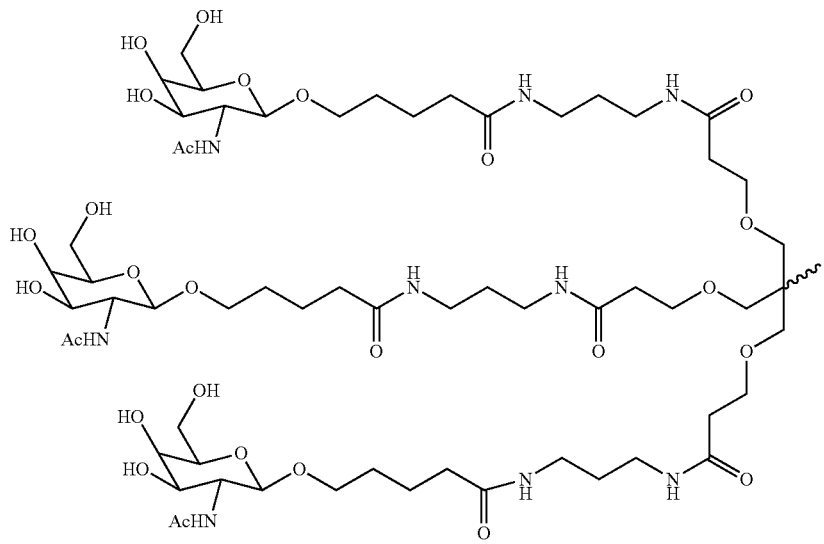

20. The method of claim 1, wherein the double stranded RNAi agent is conjugated to the (GalNAc)3 ligand as shown in the following schematic

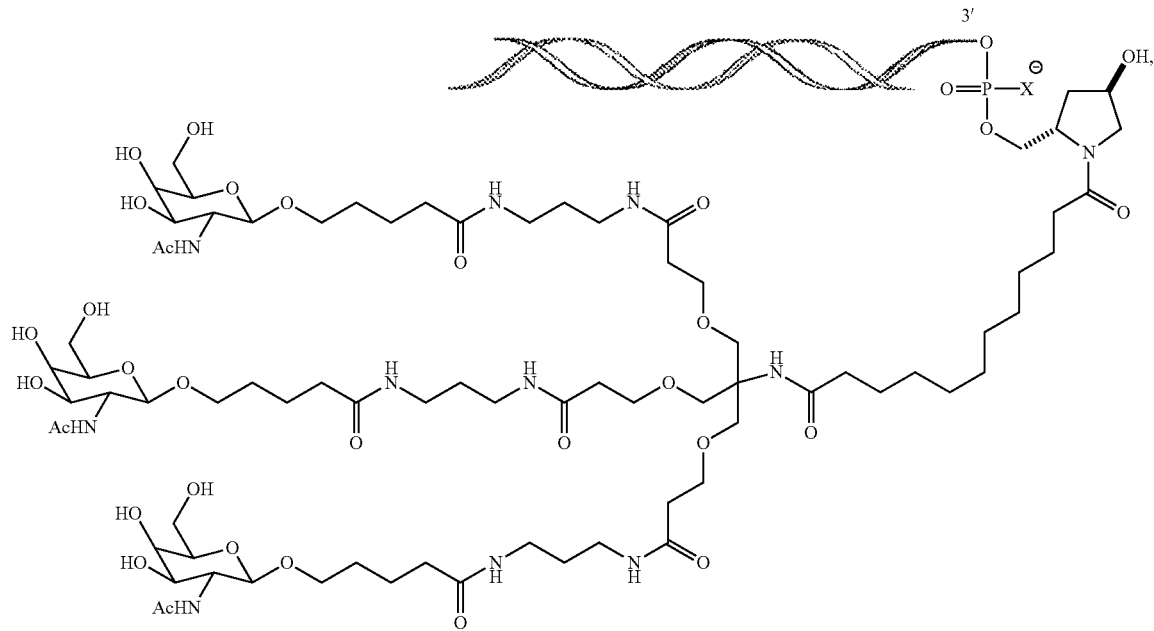

wherein X is O.

21. The method of claim 2, wherein the double stranded RNAi agent is conjugated to the (GalNAc)3 ligand as shown in the following schematic

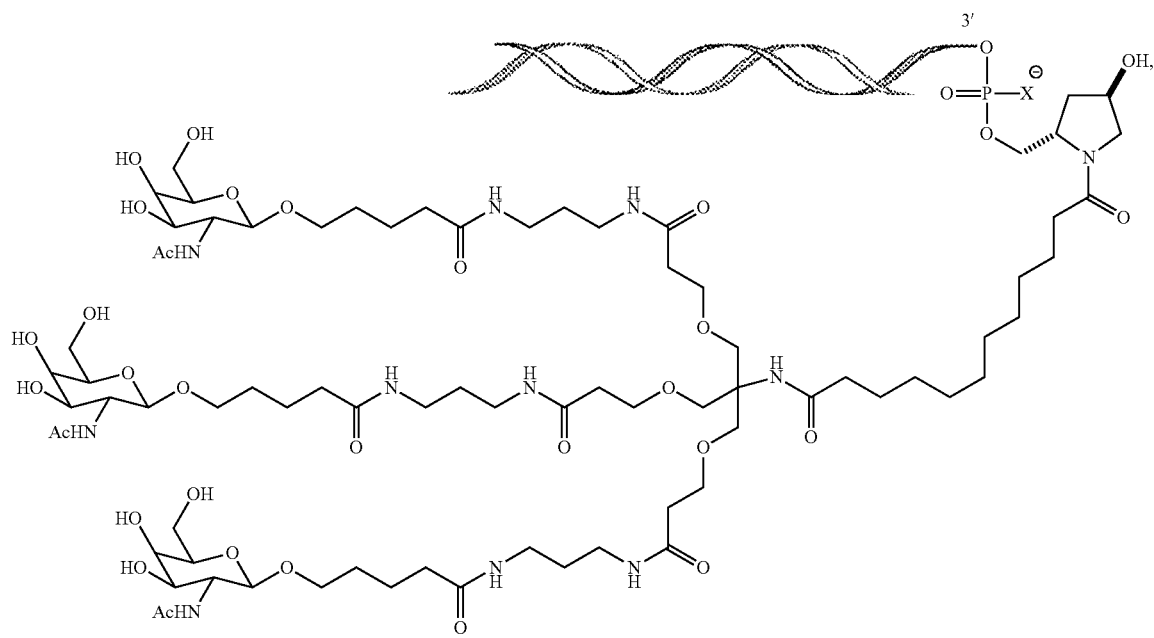

wherein X is O.

22. The method of claim 1, wherein the sense strand consists of the nucleotide sequence of 5'-csusagacCfuGfud-TuugcuuuuguT-3' (SEQ ID NO: 687) and the antisense strand consists of the nucleotide sequence of 5'-asCfsaAfAfAfgC-faAfaAfcAfgGfuCfuagsasa-3' (SEQ ID NO: 688), wherein a, g, c and u are 2'-O-methyl (2'-OMe) A, G, C, and U; Af, Gf, Cf, and Uf are 2'-fluoro A, G, C, and U; dT is 2'-deoxythymidine; s is a phosphorothioate linkage; and wherein the (GalNAc)3 ligand is conjugated to the 3' end of the sense strand as shown in the following schematic:

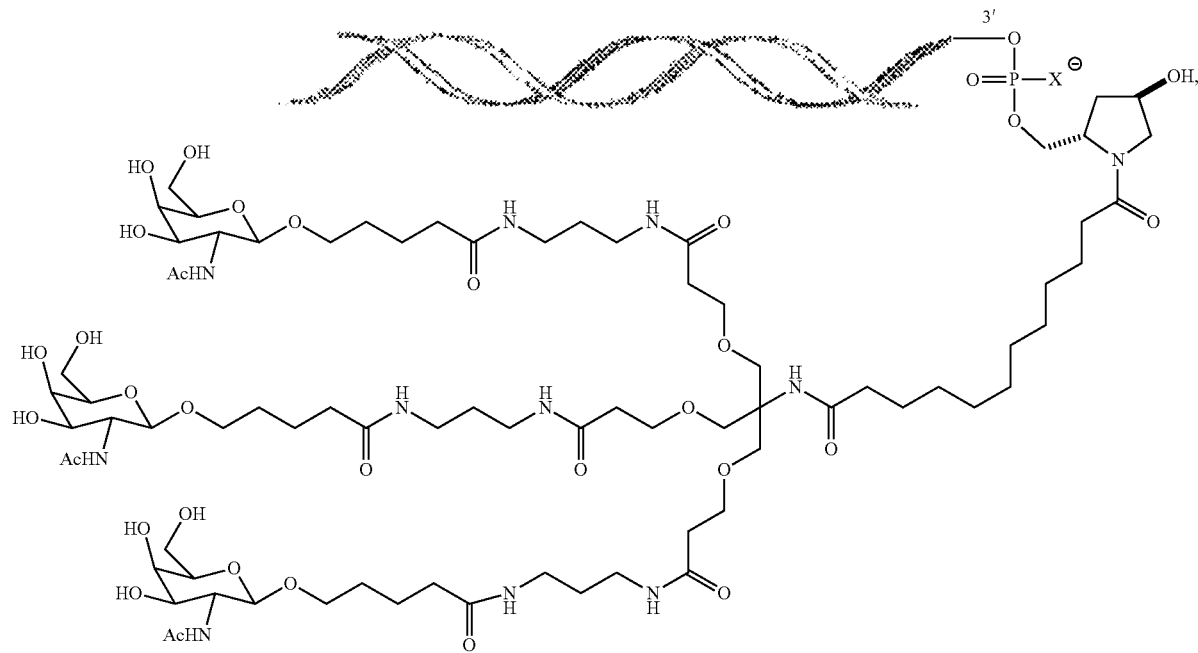

wherein X is O.

23. The method of claim 2, wherein the sense strand consists of the nucleotide sequence of 5'-csusagacCfuGfud-Tuugcuuuugu-3' (SEQ ID NO: 687) and the antisense strand consists of the nucleotide sequence of 5'-asCfsaAfAfAfgC-faAfaAfcAfgGfuCfuagsasa-3' (SEQ ID NO: 688), wherein a, g, c and u are 2'-O-methyl (2'-OMe) A, G, C, and U; Af, Gf, Cf, and Uf are 2'-fluoro A, G, C, and U; dT is 2'-deoxythymidine; s is a phosphorothioate linkage; and wherein the (GalNAc)3 ligand is conjugated to the 3' end of the sense strand as shown in the following schematic:

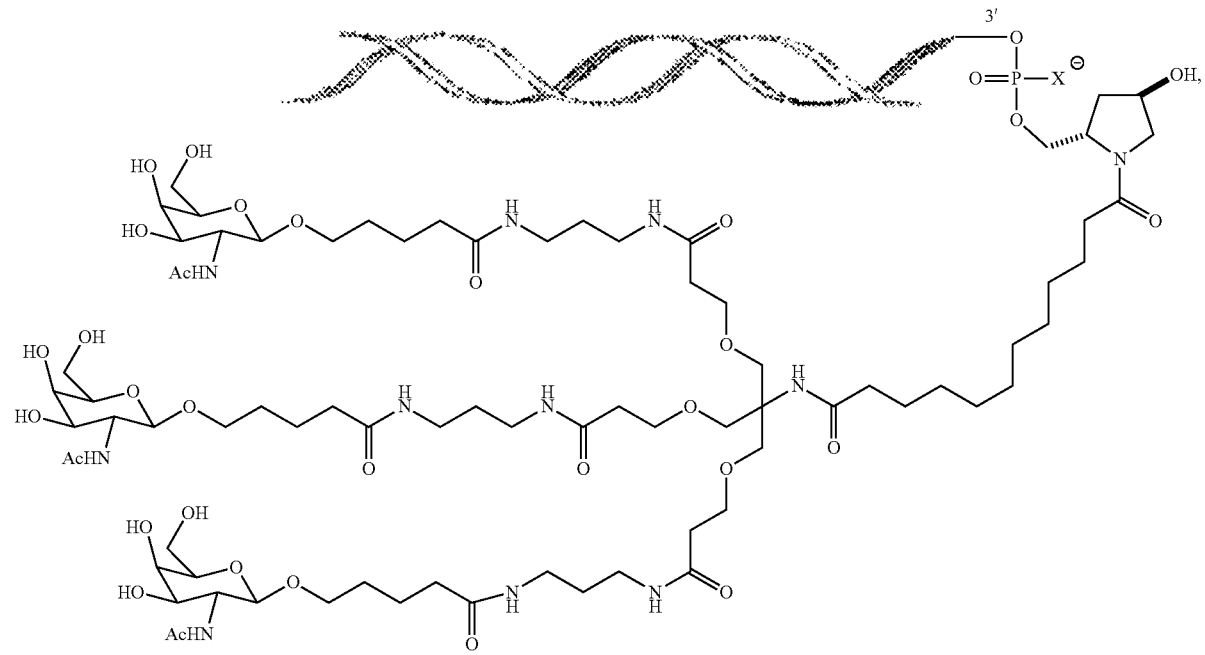

wherein X is O.

24. The method of claim 22, wherein the double stranded RNAi agent is in a salt form.

25. The method of claim 23, wherein the double stranded RNAi agent is in a salt form.

26. A method of decreasing levels of low density lipoprotein (LDLc) in serum of a human subject, comprising subcutaneously administering to the subject a fixed dose of 275 mg to 325 mg of a double stranded ribonucleic acid (RNAi) agent, or salt thereof,
  wherein the double stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuagsasa-3' (SEQ ID NO: 688),
  wherein a, g, c and u are 2'-O-methyl (2'-OMe) A, G, C, and U; Af, Gf, Cf and Uf are 2'-fluoro A, G, C and U; dT is 2'-deoxythymidine; and s is a phosphorothioate linkage, and
  wherein the double stranded RNAi agent is conjugated to a N-acetylgalactosamine (GalNAc)3 ligand.

27. The method of claim 26, wherein the subject has hypercholesterolemia.

28. The method of claim 26, wherein the subject has heterozygous LDL receptor genotype.

29. A method of decreasing levels of low density lipoprotein (LDLc) in serum of a human subject having one or more risk factors associated with cardiovascular disease, comprising subcutaneously administering to the subject a fixed dose of 275 mg to 325 mg of a double stranded ribonucleic acid (RNAi) agent, or salt thereof,
  wherein the double stranded RNAi agent comprises a sense strand and an antisense strand forming a double stranded region, wherein the sense strand comprises the nucleotide sequence of 5'-csusagacCfuGfudTuugcuuuugu-3' (SEQ ID NO: 687) and the antisense strand comprises the nucleotide sequence of 5'-asCfsaAfAfAfgCfaAfaAfcAfgGfuCfuagsasa-3' (SEQ ID NO: 688),
  wherein a, g, c and u are 2'-O-methyl (2'-OMe) A, G, C, and U; Af, Gf, Cf and Uf are 2'-fluoro A, G, C and U; dT is 2'-deoxythymidine; and s is a phosphorothioate linkage, and
  wherein the double stranded RNAi agent is conjugated to a N-acetylgalactosamine (GalNAc)3 ligand,
  wherein said one or more risk factors comprise diabetes, previous personal history of coronary heart disease (CHD) or noncoronary atherosclerosis, family history of cardiovascular disease, tobacco use, hypertension and/or obesity.

30. The method of claim 29, wherein the cardiovascular disease is selected from the group consisting of arteriosclerosis, coronary artery disease, heart valve disease, arrhythmia, heart failure, hypertension, orthostatic hypotension, shock, endocarditis, diseases of the aorta and its branches, disorders of the peripheral vascular system, heart attack, cardiomyopathy, and congenital heart disease.

\* \* \* \* \*

SEQUENCE LISTING

<160> NUMBER OF SEQ ID NOS: 688

<210> SEQ ID NO 1
<211> LENGTH: 3731
<212> TYPE: DNA
<213> ORGANISM: Homo sapiens

<400> SEQUENCE: 1

```
gtccgatggg gctctggtgg cgtgatctgc gcgccccagg cgtcaagcac ccacacccta      60
gaaggtttcc gcagcgacgt cgaggcgctc atggttgcag gcgggcgccg ccgttcagtt     120
cagggtctga gcctggagga gtgagccagg cagtgagact ggctcgggcg ggccgggacg     180
cgtcgttgca gcagcggctc ccagctccca gccaggattc cgcgcgcccc ttcacgcgcc     240
ctgctcctga acttcagctc ctgcacagtc ctccccaccg caaggctcaa ggcgccgccg     300
gcgtggaccg cgcacggcct ctaggtctcc tcgccaggac agcaacctct cccctggccc     360
tcatgggcac cgtcagctcc aggcggtcct ggtggccgct gccactgctg ctgctgctgc     420
tgctgctcct gggtcccgcg ggcgcccgtg cgcaggagga cgaggacggc gactacgagg     480
agctggtgct agccttgcgt tccgaggagg acggcctggc cgaagcaccc gagcacggaa     540
ccacagccac cttccaccgc tgcgccaagg atccgtggag gttgcctggc acctacgtgg     600
tggtgctgaa ggaggagacc cacctctcgc agtcagagcg cactgcccgc cgcctgcagg     660
cccaggctgc ccgccgggga tacctcacca agatcctgca tgtcttccat ggccttcttc     720
ctggcttcct ggtgaagatg agtggcgacc tgctggagct ggccttgaag ttgcccatg     780 tcgactacat cgaggaggac tcctctgtct ttgcccagag catcccgtgg aacctggagc     840
ggattacccc tccacggtac cgggcggatg aataccagcc ccccgacgga ggcagcctgg     900
tggaggtgta tctcctagac accagcatac agagtgacca ccgggaaatc gagggcaggg     960
tcatggtcac cgacttcgag aatgtgcccg aggaggacgg gacccgcttc cacagacagg    1020
ccagcaagtg tgacagtcat ggcacccacc tggcaggggt ggtcagcggc cgggatgccg    1080
```

```
gcgtggccaa gggtgccagc atgcgcagcc tgcgcgtgct caactgccaa gggaagggca    1140
cggttagcgg caccctcata ggcctggagt ttattcggaa aagccagctg gtccagcctg    1200
tggggccact ggtggtgctg ctgcccctgg cgggtgggta cagccgcgtc ctcaacgccg    1260
cctgccagcg cctggcgagg gctgggtcg tgctggtcac cgctgccggc aacttccggg     1320
acgatgcctg cctctactcc ccagcctcag ctcccgaggt catcacagtt ggggccacca    1380
atgcccaaga ccagccggtg accctgggga ctttggggac caactttggc cgctgtgtgg    1440
acctctttgc cccaggggag gacatcattg tgcctccag cgactgcagc acctgctttg     1500
tgtcacagag tgggacatca caggctgctg cccacgtggc tggcattgca gccatgatgc    1560
tgtctgccga gccggagctc accctggccg agttgaggca gagactgatc cacttctctg    1620
ccaaagatgt catcaatgag gcctggttcc ctgaggacca gcgggtactg accсcccaacc   1680 tggtggccgc cctgcccccc agcacccatg ggcaggttg gcagctgttt tgcaggactg     1740
tatggtcagc acactcgggg cctacacgga tggccacagc cgtcgcccgc tgcgccccag    1800
atgaggagct gctgagctgc tccagttct ccaggagtgg gaagcggcgg ggcgagcgca     1860
tggaggccca aggggcaag ctggtctgcc gggcccacaa cgcttttggg ggtgagggtg     1920
tctacgccat tgccaggtgc tgcctgctac cccaggccaa ctgcagcgtc cacacagctc    1980
caccagctga ggccagcatg gggacccgtg tccactgcca ccaacagggc cacgtcctca    2040
caggctgcag ctcccactgg gaggtggagg accttggcac ccacaagccg cctgtgctga    2100
ggccacgagg tcagcccaac cagtgcgtgg ccacaggga ggccagcatc cacgcttcct     2160
gctgccatgc cccaggtctg gaatgcaaag tcaaggagca tggaatcccg gcccctcagg    2220
agcaggtgac cgtggcctgc gaggagggct ggaccctgac tggctgcagt gccctccctg    2280
ggacctccca cgtcctgggg gcctacgccg tagacaacac gtgtgtagtc aggagccggg    2340
acgtcagcac tacaggcagc accagcgaag gggccgtgac agccgttgcc atctgctgcc    2400
ggagccggca cctggcgcag gcctcccagg agctccagtg acagccccat cccaggatgg    2460
gtgtctgggg agggtcaagg gctggggctg agctttaaaa tggttccgac ttgtccctct    2520
ctcagccctc catggcctgg cacgagggga tggggatgct tccgcctttc cggggctgct    2580
ggcctggccc ttgagtgggg cagcctcctt gcctggaact cactcactct gggtgcctcc    2640
tccccaggtg gaggtgccag gaagctccct ccctcactgt ggggcatttc accattcaaa    2700
caggtcgagc tgtgctcggg tgctgccagc tgctcccaat gtgccgatgt ccgtgggcag    2760
aatgactttt attgagctct tgttccgtgc caggcattca atcctcaggt ctccaccaag    2820
gaggcaggat tcttcccatg gatagggaag ggggcggtag gggctgcagg gacaaacatc    2880 gttgggggt gagtgtgaaa ggtgctgatg gccctcatct ccagctaact gtggagaagc    2940 ccctggggc tccctgatta atggaggctt agctttctgg atggcatcta gccagaggct    3000
ggagacaggt gcgcccctgg tggtcacagg ctgtgccttg gtttcctgag ccaccttac     3060 tctgctctat gccaggctgt gctagcaaca cccaaaggtg gcctgcgggg agccatcacc    3120
taggactgac tcggcagtgt gcagtggtgc atgcactgtc tcagccaacc cgctccacta    3180
cccggcaggg tacacattcg cacccctact tcacagagga agaaacctgg aaccagaggg    3240
ggcgtgcctg ccaagctcac acagcaggaa ctgagccaga aacgcagatt gggctggctc    3300
tgaagccaag cctcttctta cttcacccgg ctgggctcct cattttttacg ggtaacagtg    3360 aggctgggaa ggggaacaca gaccaggaag ctcggtgagt gatggcagaa cgatgcctgc    3420
aggcatggaa cttttttccgt tatcacccag gcctgattca ctggcctggc ggagatgctt    3480
```

| | |
|---|---|
| ctaaggcatg gtcggggag agggccaaca actgtccctc cttgagcacc agccccaccc | 3540 |
| aagcaagcag acatttatct tttgggtctg tcctctctgt tgccttttta cagccaactt | 3600 |
| ttctagacct gttttgcttt tgtaacttga agatatttat tctgggtttt gtagcatttt | 3660 |
| tattaatatg gtgacttttt aaaataaaaa caaacaaacg ttgtcctaac aaaaaaaaaa | 3720 |
| aaaaaaaaaa a | 3731 |

<210> SEQ ID NO 2
<211> LENGTH: 3731
<212> TYPE: DNA
<213> ORGANISM: Homo sapiens

<400> SEQUENCE: 2

| | |
|---|---|
| ttttttttt ttttttttt tgttaggaca acgtttgttt gttttttattt taaaaagtca | 60 |
| ccatattaat aaaaatgcta caaaacccag aataaatatc ttcaagttac aaaagcaaaa | 120 |
| caggtctaga aaagttggct gtaaaaaggc aacagagagg acagacccaa aagataaatg | 180 |
| tctgcttgct tgggtggggc tggtgctcaa ggagggacag ttgttggccc tctccccga | 240 |
| ccatgcctta gaagcatctc cgccaggcca gtgaatcagg cctgggtgat aacgaaaaa | 300 |
| gttccatgcc tgcaggcatc gttctgccat cactcaccga gcttcctggt ctgtgttccc | 360 |
| cttcccagcc tcactgttac ccgtaaaaat gaggagccca gccgggtgaa gtaagaagag | 420 |
| gcttggcttc agagccagcc caatctgcgt ttctggctca gttcctgctg tgtgagcttg | 480 |
| gcaggcacgc cccctctggt tccaggtttc ttcctctgtg aagtagggt gcgaatgtgt | 540 |
| accctgccgg gtagtggagc gggttggctg agacagtgca tgcaccactg cacactgccg | 600 |
| agtcagtcct aggtgatggc tccccgcagg ccacctttgg gtgttgctag cacagcctgg | 660 |
| catagagcag agtaaaggtg gctcaggaaa ccaaggcaca gcctgtgacc accaggggcg | 720 |
| cacctgtctc cagcctctgg ctagatgcca tccagaaagc taagcctcca ttaatcaggg | 780 |
| agcccccagg ggcttctcca cagttagctg gagatgaggg ccatcagcac cttcacact | 840 |
| cacccccaa cgatgtttgt ccctgcagcc cctaccgccc cctccctat ccatgggaag | 900 |
| aatcctgcct ccttggtgga gacctgagga ttgaatgcct ggcacggaac aagagctcaa | 960 |
| taaaagtcat tctgcccacg gacatcggca cattgggagc agctggcagc acccgagcac | 1020 |
| agctcgacct gtttgaatgg tgaaatgccc cacagtgagg gagggagctt cctggcacct | 1080 |
| ccacctgggg aggaggcacc cagagtgagt gagttccagg caaggaggct gccccactca | 1140 |
| agggccaggc cagcagcccc ggaaaggcgg aagcatcccc atcccctcgt gccaggccat | 1200 |
| ggagggctga gagagggaca agtcggaacc attttaaagc tcagcccag cccttgaccc | 1260 |
| tccccagaca cccatcctgg gatggggctg tcactggagc tcctgggagg cctgcgccag | 1320 |
| gtgccggctc cggcagcaga tggcaacggc tgtcacggcc ccttcgctgg tgctgcctgt | 1380 |
| agtgctgacg tcccggctcc tgactacaca cgtgttgtct acggcgtagg cccccaggac | 1440 |
| gtgggaggtc ccaggagggg cactgcagcc agtcagggtc cagccctcct cgcaggccac | 1500 |
| ggtcacctgc tcctgagggg ccgggattcc atgctccttg actttgcatt ccagacctgg | 1560 |
| ggcatggcag caggaagcgt ggatgctggc ctccctgtgg cccacgcact ggttgggctg | 1620 |
| acctcgtggc ctcagcacag gcggcttgtg ggtgccaagg tcctccacct cccagtggga | 1680 |
| gctgcagcct gtgaggacgt ggccctgttg tggcagtgg acgggtcc ccatgctggc | 1740 |
| ctcagctggt ggagctgtgt ggacgctgca gttggcctgg ggtagcaggc agcacctggc | 1800 |

| | |
|---|---|
| aatggcgtag acaccctcac ccccaaaagc gttgtgggcc cggcagacca gcttgccccc | 1860 |
| ttgggcctcc atgcgctcgc cccgccgctt cccactcctg gagaaactgg agcagctcag | 1920 |
| cagctcctca tctggggcgc agcgggcgac ggctgtggcc atccgtgtag gccccgagtg | 1980 |
| tgctgaccat acagtcctgc aaaacagctg ccaacctgcc ccatgggtgc tggggggcag | 2040 |
| ggcggccacc aggttggggg tcagtacccg ctggtcctca gggaaccagg cctcattgat | 2100 |
| gacatctttg gcagagaagt ggatcagtct ctgcctcaac tcggccaggg tgagctccgg | 2160 |
| ctcggcagac agcatcatgg ctgcaatgcc agccacgtgg gcagcagcct gtgatgtccc | 2220 |
| actctgtgac acaaagcagg tgctgcagtc gctggaggca ccaatgatgt cctcccctgg | 2280 |
| ggcaaagagg tccacacagc ggccaaagtt ggtccccaaa gtccccaggg tcaccggctg | 2340 |
| gtcttgggca ttggtggccc caactgtgat gacctcggga gctgaggctg gggagtagag | 2400 |
| gcaggcatcg tcccggaagt tgccggcagc ggtgaccagc acgaccccag ccctcgccag | 2460 |
| gcgctggcag gcggcgttga ggacgcggct gtacccaccc gccaggggca gcagcaccac | 2520 |
| cagtggcccc acaggctgga ccagctggct tttccgaata aactccaggc ctatgagggt | 2580 |
| gccgctaacc gtgcccttcc cttggcagtt gagcacgcgc aggctgcgca tgctggcacc | 2640 |
| cttggccacg ccggcatccc ggccgctgac caccctgcc aggtgggtgc catgactgtc | 2700 |
| acacttgctg gcctgtctgt ggaagcgggt cccgtcctcc tcgggcacat tctcgaagtc | 2760 |
| ggtgaccatg accctgccct cgatttcccg gtggtcactc tgtatgctgg tgtctaggag | 2820 |
| atacacctcc accaggctgc ctccgtcggg gggctggtat tcatccgccc ggtaccgtgg | 2880 |
| aggggtaatc cgctccaggt tccacgggat gctctgggca aagacagagg agtcctcctc | 2940 |
| gatgtagtcg acatggggca acttcaaggc cagctccagc aggtcgccac tcatcttcac | 3000 |
| caggaagcca ggaagaaggc catgaagac atgcaggatc ttggtgaggt atccccggcg | 3060 |
| ggcagcctgg gcctgcaggc ggcgggcagt gcgctctgac tgcgagaggt gggtctcctc | 3120 |
| cttcagcacc accacgtagg tgccaggcaa cctccacgga tccttggcgc agcggtggaa | 3180 |
| ggtggctgtg gttccgtgct cgggtgcttc ggccaggccg tcctcctcgg aacgcaaggc | 3240 |
| tagcaccagc tcctcgtagt cgccgtcctc gtcctcctgc gcacgggcgc ccgcgggacc | 3300 |
| caggagcagc agcagcagca gcagcagtgg cagcggccac caggaccgcc tggagctgac | 3360 |
| ggtgcccatg agggccaggg gagaggttgc tgtcctggcg aggagaccta gaggccgtgc | 3420 |
| gcggtccacg ccggcggcgc cttgagcctt gcggtgggga ggactgtgca ggagctgaag | 3480 |
| ttcaggagca gggcgcgtga aggggcgcgc ggaatcctgg ctgggagctg ggagccgctg | 3540 |
| ctgcaacgac gcgtcccggc ccgcccgagc cagtctcact gcctggctca ctcctccagg | 3600 |
| ctcagaccct gaactgaacg gcggcgcccg cctgcaacca tgagcgcctc gacgtcgctg | 3660 |
| cggaaaccttt ctagggtgtg ggtgcttgac gcctggggcg cgcagatcac gccaccagag | 3720 |
| ccccatcgga c | 3731 |

<210> SEQ ID NO 3
<211> LENGTH: 16
<212> TYPE: PRT
<213> ORGANISM: Unknown
<220> FEATURE:
<221> NAME/KEY: source
<223> OTHER INFORMATION: /note="Description of Unknown:
     RFGF peptide"

<400> SEQUENCE: 3

Ala Ala Val Ala Leu Leu Pro Ala Val Leu Leu Ala Leu Leu Ala Pro

<210> SEQ ID NO 4
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 4

Ala Ala Leu Leu Pro Val Leu Leu Ala Ala Pro
1               5                   10

<210> SEQ ID NO 5
<211> LENGTH: 13
<212> TYPE: PRT
<213> ORGANISM: Human immunodeficiency virus

<400> SEQUENCE: 5

Gly Arg Lys Lys Arg Arg Gln Arg Arg Arg Pro Pro Gln
1               5                   10

<210> SEQ ID NO 6
<211> LENGTH: 16
<212> TYPE: PRT
<213> ORGANISM: Drosophila sp.

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
caagcagaca uuuaucuuuu u                                                 21

<210> SEQ ID NO 8
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
aaaaagauaa augucugcuu gcu                                               23

<210> SEQ ID NO 9
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9

```
caagcagaca uuuaucuuuu u                                              21

<210> SEQ ID NO 10
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
aaaaagauaa augucugcuu gcu                                            23

<210> SEQ ID NO 11
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
caagcagaca uuuaucuuuu u                                              21

<210> SEQ ID NO 12
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
aaaaagauaa augucugcuu gcu                                            23

<210> SEQ ID NO 13
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
caagcagaca uuuaucuuuu u                                              21

<210> SEQ ID NO 14
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
aaaaagauaa augucugcuu gcu                                            23

<210> SEQ ID NO 15
<211> LENGTH: 21
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 15
caagcagaca uuuaucuuuu u                                              21

<210> SEQ ID NO 16
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
aaaaagauaa augucugcuu gcu                                            23

<210> SEQ ID NO 17
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
caagcagaca uuuaucuuuu u                                              21

<210> SEQ ID NO 18
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
aaaaagauaa augucugcuu gcu                                            23

<210> SEQ ID NO 19
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
caagcagaca uuuaucuuuu u                                              21

<210> SEQ ID NO 20
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
aaaaagauaa augucugcuu gcu                                            23

<210> SEQ ID NO 21
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
caagcagaca uuuaucuuuu u                                                 21

<210> SEQ ID NO 22
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
aaaaagauaa augucugcuu gcu                                               23

<210> SEQ ID NO 23
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
caagcagaca uuuaucuuuu u                                                 21

<210> SEQ ID NO 24
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
aaaaagauaa augucugcuu gcu                                               23

<210> SEQ ID NO 25
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
caagcagaca uuuaucuuuu u                                                 21

<210> SEQ ID NO 26
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
```
aaaaagauaa augucugcuu gcu                                        23

<210> SEQ ID NO 27
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
caagcagaca uuuaucuuuu u                                          21

<210> SEQ ID NO 28
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
aaaaagauaa augucugcuu gcu                                        23

<210> SEQ ID NO 29
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
caagcagaca uuuaucuuuu u                                          21

<210> SEQ ID NO 30
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
aaaaagauaa augucugcuu gcu                                        23

<210> SEQ ID NO 31
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
caagcagaca uuuaucuuuu u                                          21

<210> SEQ ID NO 32
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 32
aaaaagauaa augucugcuu gcu                                              23

<210> SEQ ID NO 33
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
caagcagaca uuuaucuuuu u                                                21

<210> SEQ ID NO 34
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
aaaaagauaa augucugcuu gcu                                              23

<210> SEQ ID NO 35
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
caagcagaca uuuaucuuuu u                                                21

<210> SEQ ID NO 36
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
aaaaagauaa augucugcuu gcu                                              23

<210> SEQ ID NO 37
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
caagcagaca uuuaucuuuu u                                                21
```

```
<210> SEQ ID NO 38
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
aaaaagauaa augucugcuu gcu                                            23

<210> SEQ ID NO 39
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
caagcagaca uuuaucuuuu u                                              21

<210> SEQ ID NO 40
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
aaaaagauaa augucugcuu gcu                                            23

<210> SEQ ID NO 41
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
caagcagaca uuuaucuuuu u                                              21

<210> SEQ ID NO 42
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
aaaaagauaa augucugcuu gcu                                            23

<210> SEQ ID NO 43
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 43
caagcagaca uuuaucuuuu u                                              21

<210> SEQ ID NO 44
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
aaaaagauaa augucugcuu gcu                                            23

<210> SEQ ID NO 45
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
caagcagaca uuuaucuuuu u                                              21

<210> SEQ ID NO 46
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
aaaaagauaa augucugcuu gcu                                            23

<210> SEQ ID NO 47
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
caagcagaca uuuaucuuuu u                                              21

<210> SEQ ID NO 48
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
aaaaagauaa augucugcuu gcu                                            23

<210> SEQ ID NO 49
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 49
caagcagaca uuuaucuuuu u                                                  21

<210> SEQ ID NO 50
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
aaaaagauaa augucugcuu gcu                                                23

<210> SEQ ID NO 51
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
caagcagaca uuuaucuuuu u                                                  21

<210> SEQ ID NO 52
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
aaaaagauaa augucugcuu gcu                                                23

<210> SEQ ID NO 53
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
caagcagaca uuuaucuuuu u                                                  21

<210> SEQ ID NO 54
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
aaaaagauaa augucugcuu gcu                                                23
```

```
<210> SEQ ID NO 55
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
caagcagaca uuuaucuuuu u                                              21

<210> SEQ ID NO 56
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
aaaaagauaa augucugcuu gcu                                            23

<210> SEQ ID NO 57
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
caagcagaca uuuaucuuuu u                                              21

<210> SEQ ID NO 58
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
aaaaagauaa augucugcuu gcu                                            23

<210> SEQ ID NO 59
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
caagcagaca uuuaucuuuu u                                              21

<210> SEQ ID NO 60
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 60
aaaaagauaa augucugcuu gcu                                            23

<210> SEQ ID NO 61
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
caagcagaca uuuaucuuuu u                                              21

<210> SEQ ID NO 62
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
aaaaagauaa augucugcuu gcu                                            23

<210> SEQ ID NO 63
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
caagcagaca uuuaucuuuu u                                              21

<210> SEQ ID NO 64
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
aaaaagauaa augucugcuu gcu                                            23

<210> SEQ ID NO 65
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
caagcagaca uuuaucuuuu u                                              21

<210> SEQ ID NO 66
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
aaaaagauaa augucugcuu gcu                                          23

<210> SEQ ID NO 67
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
caagcagaca uuuaucuuuu u                                            21

<210> SEQ ID NO 68
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
aaaaagauaa augucugcuu gcu                                          23

<210> SEQ ID NO 69
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
caagcagaca uuuaucuuuu u                                            21

<210> SEQ ID NO 70
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
aaaaagauaa augucugcuu gcu                                          23

<210> SEQ ID NO 71
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
caagcagaca uuuaucuuuu u                                            21
```

<210> SEQ ID NO 72
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
aaaaagauaa augucugcuu gcu                                              23

<210> SEQ ID NO 73
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
caagcagaca uuuaucuuuu u                                                21

<210> SEQ ID NO 74
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
aaaaagauaa augucugcuu gcu                                              23

<210> SEQ ID NO 75
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 75
caagcagaca uuuaucuuuu u                                                21

<210> SEQ ID NO 76
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
aaaaagauaa augucugcuu gcu                                              23

<210> SEQ ID NO 77
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 77
caagcagaca uuuaucuuuu u                                              21

<210> SEQ ID NO 78
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
aaaaagauaa augucugcuu gcu                                            23

<210> SEQ ID NO 79
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
caagcagaca uuuaucuuuu u                                              21

<210> SEQ ID NO 80
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
aaaaagauaa augucugcuu gcu                                            23

<210> SEQ ID NO 81
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
caagcagaca uuuaucuuuu u                                              21

<210> SEQ ID NO 82
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
aaaaagauaa augucugcuu gcu                                            23

<210> SEQ ID NO 83
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
caagcagaca uuuaucuuuu u                                            21

<210> SEQ ID NO 84
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
aaaaagauaa augucugcuu gcu                                          23

<210> SEQ ID NO 85
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
caagcagaca uuuaucuuuu u                                            21

<210> SEQ ID NO 86
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
aaaaagauaa augucugcuu gcu                                          23

<210> SEQ ID NO 87
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
caagcagaca uuuaucuuuu u                                            21

<210> SEQ ID NO 88
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
```
aaaaagauaa augucugcuu gcu                                         23

<210> SEQ ID NO 89
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
caagcagaca uuuaucuuuu u                                           21

<210> SEQ ID NO 90
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
aaaaagauaa augucugcuu gcu                                         23

<210> SEQ ID NO 91
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
caagcagaca uuuaucuuuu u                                           21

<210> SEQ ID NO 92
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
aaaaagauaa augucugcuu gcu                                         23

<210> SEQ ID NO 93
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
caagcagaca uuuaucuuuu u                                           21

<210> SEQ ID NO 94
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 94
aaaaagauaa augucugcuu gcu                                            23

<210> SEQ ID NO 95
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
caagcagaca uuuaucuuuu u                                              21

<210> SEQ ID NO 96
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
aaaaagauaa augucugcuu gcu                                            23

<210> SEQ ID NO 97
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
caagcagaca uuuaucuuuu u                                              21

<210> SEQ ID NO 98
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
aaaaagauaa augucugcuu gcu                                            23

<210> SEQ ID NO 99
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
caagcagaca uuuaucuuuu u                                              21

<210> SEQ ID NO 100
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
aaaaagauaa augucugcuu gcu                                            23

<210> SEQ ID NO 101
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
caagcagaca uuuaucuuuu u                                              21

<210> SEQ ID NO 102
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
aaaaagauaa augucugcuu gcu                                            23

<210> SEQ ID NO 103
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 103
caagcagaca uuuaucuuuu u                                              21

<210> SEQ ID NO 104
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
aaaaagauaa augucugcuu gcu                                            23

<210> SEQ ID NO 105
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
```

```
caagcagaca uuuaucuuuu u                                              21

<210> SEQ ID NO 106
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
aaaaagauaa augucugcuu gcu                                            23

<210> SEQ ID NO 107
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
caagcagaca uuuaucuuuu u                                              21

<210> SEQ ID NO 108
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
aaaaagauaa augucugcuu gcu                                            23

<210> SEQ ID NO 109
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
caagcagaca uuuaucuuuu u                                              21

<210> SEQ ID NO 110
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
aaaaagauaa augucugcuu gcu                                            23

<210> SEQ ID NO 111
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 111
caagcagaca uuuaucuuuu u                                              21

<210> SEQ ID NO 112
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
aaaaagauaa augucugcuu gcu                                            23

<210> SEQ ID NO 113
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
caagcagaca uuuaucuuuu u                                              21

<210> SEQ ID NO 114
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
aaaaagauaa augucugcuu gcu                                            23

<210> SEQ ID NO 115
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
caagcagaca uuuaucuuuu u                                              21

<210> SEQ ID NO 116
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
aaaaagauaa augucugcuu gcu                                            23
```

```
<210> SEQ ID NO 117
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
caagcagaca uuuaucuuuu u                                              21

<210> SEQ ID NO 118
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
aaaaagauaa augucugcuu gcu                                            23

<210> SEQ ID NO 119
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
caagcagaca uuuaucuuuu u                                              21

<210> SEQ ID NO 120
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 120
aaaaagauaa augucugcuu gcu                                            23

<210> SEQ ID NO 121
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
caagcagaca uuuaucuuuu u                                              21

<210> SEQ ID NO 122
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 122
aaaaagauaa augucugcuu gcu                                           23

<210> SEQ ID NO 123
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
caagcagaca uuuaucuuuu u                                             21

<210> SEQ ID NO 124
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
aaaaagauaa augucugcuu gcu                                           23

<210> SEQ ID NO 125
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
caagcagaca uuuaucuuuu u                                             21

<210> SEQ ID NO 126
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
aaaaagauaa augucugcuu gcu                                           23

<210> SEQ ID NO 127
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
caagcagaca uuuaucuuuu u                                             21

<210> SEQ ID NO 128
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 128
aaaaagauaa augucugcuu gcu                                            23

<210> SEQ ID NO 129
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
caagcagaca uuuaucuuuu u                                              21

<210> SEQ ID NO 130
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
aaaaagauaa augucugcuu gcu                                            23

<210> SEQ ID NO 131
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
caagcagaca uuuaucuuuu u                                              21

<210> SEQ ID NO 132
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
aaaaagauaa augucugcuu gcu                                            23

<210> SEQ ID NO 133
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
caagcagaca uuuaucuuuu u                                              21
```

<210> SEQ ID NO 134
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
aaaaagauaa augucugcuu gcu                                           23

<210> SEQ ID NO 135
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
caagcagaca uuuaucuuuu u                                             21

<210> SEQ ID NO 136
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
aaaaagauaa augucugcuu gcu                                           23

<210> SEQ ID NO 137
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 137
caagcagaca uuuaucuuuu u                                             21

<210> SEQ ID NO 138
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
aaaaagauaa augucugcuu gcu                                           23

<210> SEQ ID NO 139
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

-continued

<400> SEQUENCE: 139
caagcagaca uuuaucuuuu u                                     21

<210> SEQ ID NO 140
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
aaaaagauaa augucugcuu gcu                                   23

<210> SEQ ID NO 141
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
caagcagaca uuuaucuuuu u                                     21

<210> SEQ ID NO 142
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
aaaaagauaa augucugcuu gcu                                   23

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
caagcagaca uuuaucuuuu u                                     21

<210> SEQ ID NO 144
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
aaaaagauaa augucugcuu gcu                                   23

<210> SEQ ID NO 145
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
caagcagaca uuuaucuuuu u                                                    21

<210> SEQ ID NO 146
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
aaaaagauaa augucugcuu gcu                                                  23

<210> SEQ ID NO 147
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
caagcagaca uuuaucuuuu u                                                    21

<210> SEQ ID NO 148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
aaaaagauaa augucugcuu gcu                                                  23

<210> SEQ ID NO 149
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
caagcagaca uuuaucuuuu u                                                    21

<210> SEQ ID NO 150
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
aaaaagauaa augucugcuu gcu                                                  23
```

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 151
caagcagaca uuuaucuuuu u                                              21

<210> SEQ ID NO 152
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 152
aaaaagauaa augucugcuu gcu                                            23

<210> SEQ ID NO 153
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 153
caagcagaca uuuaucuuuu u                                              21

<210> SEQ ID NO 154
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 154
aaaaagauaa augucugcuu gcu                                            23

<210> SEQ ID NO 155
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 155
caagcagaca uuuaucuuuu u                                              21

<210> SEQ ID NO 156
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
          Synthetic oligonucleotide"

<400> SEQUENCE: 156
aaaaagauaa augucugcuu gcu                                            23

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
caagcagaca uuuaucuuuu u                                              21

<210> SEQ ID NO 158
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
aaaaagauaa augucugcuu gcu                                            23

<210> SEQ ID NO 159
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
caagcagaca uuuaucuuuu u                                              21

<210> SEQ ID NO 160
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
aaaaagauaa augucugcuu gcu                                            23

<210> SEQ ID NO 161
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
caagcagaca uuuaucuuuu u                                              21

<210> SEQ ID NO 162
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
aaaaagauaa augucugcuu gcu                                           23

<210> SEQ ID NO 163
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
caagcagaca uuuaucuuuu u                                             21

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
aaaaagauaa augucugcuu gcu                                           23

<210> SEQ ID NO 165
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
caagcagaca uuuaucuuuu u                                             21

<210> SEQ ID NO 166
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
aaaaagauaa augucugcuu gcu                                           23

<210> SEQ ID NO 167
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
```
caagcagaca uuuaucuuuu u                                              21

<210> SEQ ID NO 168
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
aaaaagauaa augucugcuu gcu                                            23

<210> SEQ ID NO 169
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
caagcagaca uuuaucuuuu u                                              21

<210> SEQ ID NO 170
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
aaaaagauaa augucugcuu gcu                                            23

<210> SEQ ID NO 171
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171
caagcagaca uuuaucuuuu u                                              21

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
aaaaagauaa augucugcuu gcu                                            23

<210> SEQ ID NO 173
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 173
caagcagaca uuuaucuuuu u                                              21

<210> SEQ ID NO 174
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
aaaaagauaa augucugcuu gcu                                            23

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
caagcagaca uuuaucuuuu u                                              21

<210> SEQ ID NO 176
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
aaaaagauaa augucugcuu gcu                                            23

<210> SEQ ID NO 177
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
caagcagaca uuuaucuuuu u                                              21

<210> SEQ ID NO 178
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
aaaaagauaa augucugcuu gcu                                            23

<210> SEQ ID NO 179
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
caagcagaca uuuaucuuuu u                                              21

<210> SEQ ID NO 180
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
aaaaagauaa augucugcuu gcu                                            23

<210> SEQ ID NO 181
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
caagcagaca uuuaucuuuu u                                              21

<210> SEQ ID NO 182
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 182
aaaaagauaa augucugcuu gcu                                            23

<210> SEQ ID NO 183
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
caagcagaca uuuaucuuuu u                                              21

<210> SEQ ID NO 184
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
```
aaaaagauaa augucugcuu gcu                                            23

<210> SEQ ID NO 185
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
caagcagaca uuuaucuuuu u                                              21

<210> SEQ ID NO 186
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
aaaaagauaa augucugcuu gcu                                            23

<210> SEQ ID NO 187
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
caagcagaca uuuaucuuuu u                                              21

<210> SEQ ID NO 188
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188
aaaaagauaa augucugcuu gcu                                            23

<210> SEQ ID NO 189
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aagcagacau uuaucuuuug a                                              21

<210> SEQ ID NO 190
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 190
ucaaaagaua aaugucugcu ugc                                              23

<210> SEQ ID NO 191
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
agcagacauu uaucuuuugg a                                                21

<210> SEQ ID NO 192
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
uccaaaagau aaaugucugc uug                                              23

<210> SEQ ID NO 193
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
gcagacauuu aucuuuuggg u                                                21

<210> SEQ ID NO 194
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
acccaaaaga uaaaugucug cuu                                              23

<210> SEQ ID NO 195
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
agacauuuau cuuuuggguc u                                                21
```

```
<210> SEQ ID NO 196
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
agacccaaaa gauaaauguc ugc                                              23

<210> SEQ ID NO 197
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
gacauuuauc uuuugggucu u                                                21

<210> SEQ ID NO 198
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
aagacccaaa agauaaaugu cug                                              23

<210> SEQ ID NO 199
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 199
acauuuaucu uuugggucug u                                                21

<210> SEQ ID NO 200
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200
acagacccaa aagauaaaug ucu                                              23

<210> SEQ ID NO 201
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 201
uuuaucuuuu gggucugucc u                                               21

<210> SEQ ID NO 202
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aggacagacc caaaagauaa aug                                             23

<210> SEQ ID NO 203
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
uuaucuuuug ggucuguccu u                                               21

<210> SEQ ID NO 204
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
aaggacagac ccaaaagaua aau                                             23

<210> SEQ ID NO 205
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
uaucuuuugg gucuguccuc u                                               21

<210> SEQ ID NO 206
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
agaggacaga cccaaaagau aaa                                             23

<210> SEQ ID NO 207
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 207
aucuuuuggg ucguccucu u                                              21

<210> SEQ ID NO 208
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
aagaggacag acccaaaaga uaa                                           23

<210> SEQ ID NO 209
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
ucuuuugggu cuguccucuc u                                             21

<210> SEQ ID NO 210
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
agagaggaca gacccaaaag aua                                           23

<210> SEQ ID NO 211
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
uuuugggucu guccucucug u                                             21

<210> SEQ ID NO 212
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
acagagagga cagacccaaa aga                                           23
```

```
<210> SEQ ID NO 213
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
uuugggucug uccucucugu u                                              21

<210> SEQ ID NO 214
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
aacagagagg acagacccaa aag                                            23

<210> SEQ ID NO 215
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
uugggucugu ccucucuguu u                                              21

<210> SEQ ID NO 216
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
aaacagagag gacagaccca aaa                                            23

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
ugggucuguc cucucuguug a                                              21

<210> SEQ ID NO 218
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 218
ucaacagaga ggacagaccc aaa                                              23

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
gggucugucc ucucuguugc a                                                21

<210> SEQ ID NO 220
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
ugcaacagag aggacagacc caa                                              23

<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ggucuguccu cucuguugcc u                                                21

<210> SEQ ID NO 222
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aggcaacaga gaggacagac cca                                              23

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
gucuguccuc ucuguugccu u                                                21

<210> SEQ ID NO 224
<211> LENGTH: 23
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
aaggcaacag agaggacaga ccc                                            23

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225 ucguccucu cguugccuu u                                                21

<210> SEQ ID NO 226
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226 aaagcaaca gagaggacag acc                                             23

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227 cguccucuc uguugccuuu u                                               21

<210> SEQ ID NO 228
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
aaaaggcaac agagaggaca gac                                            23

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uguccucucu guugccuuuu u                                              21
```

<210> SEQ ID NO 230
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
aaaaaggcaa cagagaggac aga                                            23

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
guccucucug uugccuuuuu a                                              21

<210> SEQ ID NO 232
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
uaaaaaggca acagagagga cag                                            23

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
uuuucuagac cuguuuugcu u                                              21

<210> SEQ ID NO 234
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
aagcaaaaca ggucuagaaa agu                                            23

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 235
uuucuagacc uguuuugcuu u                                        21

<210> SEQ ID NO 236
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
aaagcaaaac aggucuagaa aag                                      23

<210> SEQ ID NO 237
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
cuagaccugu uuugcuuuug u                                        21

<210> SEQ ID NO 238
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
acaaaagcaa aacaggucua gaa                                      23

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
cuagaccugu uuugcuuuug u                                        21

<210> SEQ ID NO 240
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
acaaaagcaa aacaggucua gaa                                      23

<210> SEQ ID NO 241
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
uucuagaccu guuuugcuuu u                                              21

<210> SEQ ID NO 242
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
aaaagcaaaa caggucuaga aaa                                            23

<210> SEQ ID NO 243
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
cuagaccugu uuugcuuuug u                                              21

<210> SEQ ID NO 244
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
acaaaagcaa aacaggucua gaa                                            23

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
cuagaccugu uuugcuuuug u                                              21

<210> SEQ ID NO 246
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
```

```
acaaaagcaa aacaggucua gaa                                          23
```

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247

```
cuagaccugu uuugcuuuug u                                            21
```

<210> SEQ ID NO 248
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248

```
acaaaagcaa aacaggucua gaa                                          23
```

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249

```
cuagaccugu uuugcuuuug u                                            21
```

<210> SEQ ID NO 250
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250

```
acaaaagcaa aacaggucua gaa                                          23
```

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251

```
cuagaccugu uuugcuuuug u                                            21
```

<210> SEQ ID NO 252
<211> LENGTH: 23
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 252
acaaaagcaa aacaggucua gaa                                              23

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
cuagaccugu uuugcuuuug u                                                21

<210> SEQ ID NO 254
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
acaaaagcaa aacaggucua gaa                                              23

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
cuagaccugu uuugcuuuug u                                                21

<210> SEQ ID NO 256
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
acaaaagcaa aacaggucua gaa                                              23

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
cuagaccugu uuugcuuuug u                                                21

<210> SEQ ID NO 258
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
acaaaagcaa aacaggucua gaa                                              23

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
cuagaccugu uuugcuuuug u                                                21

<210> SEQ ID NO 260
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
acaaaagcaa aacaggucua gaa                                              23

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
cuagaccugu uuugcuuuug u                                                21

<210> SEQ ID NO 262
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
acaaaagcaa aacaggucua gaa                                              23

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
```

-continued cuagaccugu uuugcuuuug u                                              21

<210> SEQ ID NO 264
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
acaaaagcaa aacaggucua gaa                                            23

<210> SEQ ID NO 265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
cuagaccugu uuugcuuuug u                                              21

<210> SEQ ID NO 266
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
acaaaagcaa aacaggucua gaa                                            23

<210> SEQ ID NO 267
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
cuagaccugu uuugcuuuug u                                              21

<210> SEQ ID NO 268
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
acaaaagcaa aacaggucua gaa                                            23

<210> SEQ ID NO 269
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 269
cuagaccugu uuugcuuuug u                                                  21

<210> SEQ ID NO 270
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
acaaaagcaa aacaggucua gaa                                                23

<210> SEQ ID NO 271
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
cuagaccugu uuugcuuuug u                                                  21

<210> SEQ ID NO 272
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
acaaaagcaa aacaggucua gaa                                                23

<210> SEQ ID NO 273
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
cuagaccugu uuugcuuuug u                                                  21

<210> SEQ ID NO 274
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
acaaaagcaa aacaggucua gaa                                                23

```
<210> SEQ ID NO 275
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
cuagaccugu uuugcuuuug u                                              21

<210> SEQ ID NO 276
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
acaaaagcaa aacaggucua gaa                                            23

<210> SEQ ID NO 277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
cuagaccugu uuugcuuuug u                                              21

<210> SEQ ID NO 278
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
acaaaagcaa aacaggucua gaa                                            23

<210> SEQ ID NO 279
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
cuagaccugu uuugcuuuug u                                              21

<210> SEQ ID NO 280
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 280
acaaaagcaa aacaggucua gaa                                               23

<210> SEQ ID NO 281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281
cuagaccugu uuugcuuuug u                                                 21

<210> SEQ ID NO 282
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282
acaaaagcaa aacaggucua gaa                                               23

<210> SEQ ID NO 283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
cuagaccugu uuugcuuuug u                                                 21

<210> SEQ ID NO 284
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
acaaaagcaa aacaggucua gaa                                               23

<210> SEQ ID NO 285
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
cuagaccugu uuugcuuuug u                                                 21

<210> SEQ ID NO 286
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 286
acaaaagcaa aacaggucua gaa                                              23

<210> SEQ ID NO 287
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
cuagaccugu uuugcuuuug u                                                21

<210> SEQ ID NO 288
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
acaaaagcaa aacaggucua gaa                                              23

<210> SEQ ID NO 289
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
cuagaccugu uuugcuuuug u                                                21

<210> SEQ ID NO 290
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
acaaaagcaa aacaggucua gaa                                              23

<210> SEQ ID NO 291
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
cuagaccugu uuugcuuuug u                                                21
```

```
<210> SEQ ID NO 292
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
acaaaagcaa aacaggucua gaa                                              23

<210> SEQ ID NO 293
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
cuagaccugu uuugcuuuug u                                                21

<210> SEQ ID NO 294
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
acaaaagcaa aacaggucua gaa                                              23

<210> SEQ ID NO 295
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
cuagaccugu uuugcuuuug u                                                21

<210> SEQ ID NO 296
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
acaaaagcaa aacaggucua gaa                                              23

<210> SEQ ID NO 297
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 297
cuagaccugu uuugcuuuug u                                          21

<210> SEQ ID NO 298
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
acaaaagcaa aacaggucua gaa                                        23

<210> SEQ ID NO 299
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
cuagaccugu uuugcuuuug u                                          21

<210> SEQ ID NO 300
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
acaaaagcaa aacaggucua gaa                                        23

<210> SEQ ID NO 301
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
cuagaccugu uuugcuuuug u                                          21

<210> SEQ ID NO 302
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
acaaaagcaa aacaggucua gaa                                        23

<210> SEQ ID NO 303
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
cuagaccugu uuugcuuuug u                                               21

<210> SEQ ID NO 304
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
acaaaagcaa aacaggucua gaa                                             23

<210> SEQ ID NO 305
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
cuagaccugu uuugcuuuug u                                               21

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
acaaaagcaa aacaggucua gaa                                             23

<210> SEQ ID NO 307
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
cuagaccugu uuugcuuuug u                                               21

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
acaaaagcaa aacaggucua gaa                                             23
```

```
<210> SEQ ID NO 309
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
cuagaccugu uuugcuuuug u                                                    21

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
acaaaagcaa aacaggucua gaa                                                  23

<210> SEQ ID NO 311
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
cuagaccugu uuugcuuuug u                                                    21

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
acaaaagcaa aacaggucua gaa                                                  23

<210> SEQ ID NO 313
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
cuagaccugu uuugcuuuug u                                                    21

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 314
acaaaagcaa aacaggucua gaa         23

<210> SEQ ID NO 315
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
cuagaccugu uuugcuuuug u         21

<210> SEQ ID NO 316
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 316
acaaaagcaa aacaggucua gaa         23

<210> SEQ ID NO 317
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
cuagaccugu uuugcuuuug u         21

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
acaaaagcaa aacaggucua gaa         23

<210> SEQ ID NO 319
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
cuagaccugu uuugcuuuug u         21

<210> SEQ ID NO 320
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
acaaaagcaa aacaggucua gaa                                           23

<210> SEQ ID NO 321
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
cuagaccugu uuugcuuuug u                                             21

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
acaaaagcaa aacaggucua gaa                                           23

<210> SEQ ID NO 323
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
cuagaccugu uuugcuuuug u                                             21

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
acaaaagcaa aacaggucua gaa                                           23

<210> SEQ ID NO 325
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
```
cuagaccugu uuugcuuuug u                                              21

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
acaaaagcaa aacaggucua gaa                                            23

<210> SEQ ID NO 327
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 327
ctagaccugu uuugcuuuug u                                              21

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
acaaaagcaa aacaggucua gaa                                            23

<210> SEQ ID NO 329
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329
ctagaccugu uuugcuuuug u                                              21

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
acaaaagcaa aacaggucua gaa                                            23

-continued

```
<210> SEQ ID NO 331
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
cuagaccugu uuugcuuuug u                                              21

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
acaaaagcaa aacaggucua gaa                                            23

<210> SEQ ID NO 333
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
cuagaccugu uuugcuuuug u                                              21

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
acaaaagcaa aacaggucua gaa                                            23

<210> SEQ ID NO 335
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
cuagaccugu uuugcuuuug u                                              21

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 336
acaaaagcaa aacaggucua gaa                                              23

<210> SEQ ID NO 337
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
cuagaccugu uuugcuuuug u                                                21

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
acaaaagcaa aacaggucua gaa                                              23

<210> SEQ ID NO 339
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
cuagaccugu uuugcuuuug u                                                21

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
acaaaagcaa aacaggucua gaa                                              23

<210> SEQ ID NO 341
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
cuagaccugu uuugcuuuug u                                                21

<210> SEQ ID NO 342
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
acaaaagcaa aacaggucua gaa                                            23

<210> SEQ ID NO 343
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
cuagaccugu uuugcuuuug u                                              21

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
acaaaagcaa aacaggucua gaa                                            23

<210> SEQ ID NO 345
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
cuagaccugu uuugcuuuug u                                              21

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
acaaaagcaa aacaggucua gaa                                            23

<210> SEQ ID NO 347
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
```
cuagaccugu uuugcuuuug u                                              21

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
acaaaagcaa aacaggucua gaa                                            23

<210> SEQ ID NO 349
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
cuagaccugu uuugcuuuug u                                              21

<210> SEQ ID NO 350
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
acaaaagcaa aacaggucua gaa                                            23

<210> SEQ ID NO 351
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
cuagaccugu uuugcuuuug u                                              21

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
acaaaagcaa aacaggucua gaa                                            23

<210> SEQ ID NO 353
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 353
uagaccuguu uugcuuuugu                                              20

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
acaaaagcaa aacaggucua gaa                                          23

<210> SEQ ID NO 355
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
agaccuguuu ugcuuuugu                                               19

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
acaaaagcaa aacaggucua gaa                                          23

<210> SEQ ID NO 357
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
ucuagaccug uuuugcuuuu gu                                           22

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
acaaaagcaa aacaggucua gaa                                          23

<210> SEQ ID NO 359
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
uucuagaccu guuuugcuuu ugu                                              23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
acaaaagcaa aacaggucua gaa                                              23

<210> SEQ ID NO 361
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
cuagaccugu uuugcuuuug u                                                21

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
acaaaagcaa aacaggucua gaa                                              23

<210> SEQ ID NO 363
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
cuagaccugu uuugcuuuug u                                                21

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
```
acaaaagcaa aacaggucua gaa                                          23

<210> SEQ ID NO 365
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
cuagaccugu uuugcuuuug u                                            21

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 366
acaaaagcaa aacaggucua gaa                                          23

<210> SEQ ID NO 367
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
cuagaccugu uuugcuuuug u                                            21

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
acaaaagcaa aacaggucua gaa                                          23

<210> SEQ ID NO 369
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
cuagaccugu uuugcuuuug u                                            21

<210> SEQ ID NO 370
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 370
acaaaagcaa aacaggucua gaa                                           23

<210> SEQ ID NO 371
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
cuagaccugu uuugcuuuug u                                             21

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
acaaaagcaa aacaggucua gaa                                           23

<210> SEQ ID NO 373
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
cuagaccugu uuugcuuuug u                                             21

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
acaaaagcaa aacaggucua gaa                                           23

<210> SEQ ID NO 375
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
cuagaccugu uuugcuuuug u                                             21
```

```
<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
acaaaagcaa aacaggucua gaa                                              23

<210> SEQ ID NO 377
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
cuagaccugu uuugcuuuug u                                                21

<210> SEQ ID NO 378
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
acaaaagcaa aacaggucua gaa                                              23

<210> SEQ ID NO 379
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
cuagaccugu uuugcuuuug u                                                21

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
acaaaagcaa aacaggucua gaa                                              23

<210> SEQ ID NO 381
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 381
cuagaccugu uuugcuuuug u                                              21

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
acaaaagcaa aacaggucua gaa                                            23

<210> SEQ ID NO 383
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
cuagaccugu uuugcuuuug u                                              21

<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
acaaaagcaa aacaggucua gaa                                            23

<210> SEQ ID NO 385
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
cuagaccugu uuugcuuuug u                                              21

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
acaaaagcaa aacaggucua gaa                                            23

<210> SEQ ID NO 387
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 387
cuagaccugu uuugcuuuug u                                              21

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
acaaaagcaa aacaggucua gaa                                            23

<210> SEQ ID NO 389
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
cuagaccugu uuugcuuuug u                                              21

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
acaaaagcaa aacaggucua gaa                                            23

<210> SEQ ID NO 391
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
cuagaccugu uuugcuuuug u                                              21

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
acaaaagcaa aacaggucua gaa                                            23
```

```
<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
cuagaccugu uuugcuuuug u                                             21

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
acaaaagcaa aacaggucua gaa                                           23

<210> SEQ ID NO 395
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
cuagaccugu uuugcuuuug u                                             21

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
acaaaagcaa aacaggucua gaa                                           23

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
ucuagaccug uuuugcuuuu u                                             21

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 398
aaaaagcaaa acaggucuag aaa                                              23

<210> SEQ ID NO 399
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
cuagaccugu uuugcuuuug u                                                21

<210> SEQ ID NO 400
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
acaaaagcaa aacaggucua ga                                               22

<210> SEQ ID NO 401
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
uagaccuguu uugcuuuugu                                                  20

<210> SEQ ID NO 402
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
acaaaagcaa aacaggucua ga                                               22

<210> SEQ ID NO 403
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
agaccuguuu ugcuuuugu                                                   19

<210> SEQ ID NO 404
<211> LENGTH: 22
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
acaaaagcaa aacaggucua ga                                              22

<210> SEQ ID NO 405
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
uagaccuguu uugcuuuugu                                                 20

<210> SEQ ID NO 406
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
acaaaagcaa aacaggucua ga                                              22

<210> SEQ ID NO 407
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
uagaccuguu uugcuuuugu                                                 20

<210> SEQ ID NO 408
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
acaaaagcaa aacaggucua ga                                              22

<210> SEQ ID NO 409
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
cuagaccugu uuugcuuuug u                                               21
```

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
acaaaagcaa aacaggucua gaa                                           23

<210> SEQ ID NO 411
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
cuagaccugu uuugcuuuug u                                             21

<210> SEQ ID NO 412
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
acaaaagcaa aacaggucua gaa                                           23

<210> SEQ ID NO 413
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
cuagaccugu uuugcuuuug u                                             21

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
acaaaagcaa aacaggucua gaa                                           23

<210> SEQ ID NO 415
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 415
cuagaccugu uuugcuuuug u                                              21

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
acaaaagcaa aacaggucua gaa                                            23

<210> SEQ ID NO 417
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
cuagaccugu uuugcuuuug u                                              21

<210> SEQ ID NO 418
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
acaaaagcaa aacaggucua gaa                                            23

<210> SEQ ID NO 419
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
cuagaccugu uuugcuuuug u                                              21

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
acaaaagcaa aacaggucua gaa                                            23

<210> SEQ ID NO 421
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cuagaccugu uuugcuuuug u                                              21

<210> SEQ ID NO 422
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 422
acaaaagcaa aacaggucua gaa                                            23

<210> SEQ ID NO 423
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
cuagaccugu uuugcuuuug u                                              21

<210> SEQ ID NO 424
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
acaaaagcaa aacaggucua gaa                                            23

<210> SEQ ID NO 425
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
cuagaccugu uuugcuuuug u                                              21

<210> SEQ ID NO 426
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
```
acaaaagcaa aacaggucua gaa                                            23

<210> SEQ ID NO 427
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
cuagaccugu uuugcuuuug u                                              21

<210> SEQ ID NO 428
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
acaaaagcaa aacaggucua gaa                                            23

<210> SEQ ID NO 429
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
cuagaccugu uuugcuuuug u                                              21

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
acaaaagcaa aacaggucua gaa                                            23

<210> SEQ ID NO 431
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
cuagaccugu uuugcuuuug u                                              21

<210> SEQ ID NO 432
<211> LENGTH: 23
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 432
acaaaagcaa aacaggucua gaa                                        23

<210> SEQ ID NO 433
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
cuagaccugu uuugcuuuug u                                          21

<210> SEQ ID NO 434
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
acaaaagcaa aacaggucua gaa                                        23

<210> SEQ ID NO 435
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
cuagaccugu uuugcuuuug u                                          21

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
acaaaagcaa aacaggucua gaa                                        23

<210> SEQ ID NO 437
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
cuagaccugu uuugcuuuug u                                          21

<210> SEQ ID NO 438
```

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
acaaaagcaa aacaggucua gaa                                          23

<210> SEQ ID NO 439
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 439
cuagaccugu uuugcuuuug u                                            21

<210> SEQ ID NO 440
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
acaaaagcaa aacaggucua gaa                                          23

<210> SEQ ID NO 441
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
cuagaccugu uuugcuuuug u                                            21

<210> SEQ ID NO 442
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
acaaaagcaa aacaggucua gaa                                          23

<210> SEQ ID NO 443
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
```

```
cuagaccugu uuugcuuuug u                                                  21

<210> SEQ ID NO 444
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
acaaaagcaa aacaggucua gaa                                                23

<210> SEQ ID NO 445
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 445
cuagaccugu uuugcuuuug u                                                  21

<210> SEQ ID NO 446
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
acaaaagcaa aacaggucua gaa                                                23

<210> SEQ ID NO 447
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
cuagaccugu uuugcuuuug u                                                  21

<210> SEQ ID NO 448
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
acaaaagcaa aacaggucua gaa                                                23

<210> SEQ ID NO 449
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 449
cuagaccugu uuugcuuuug u                                              21

<210> SEQ ID NO 450
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
acaaaagcaa aacaggucua gaa                                            23

<210> SEQ ID NO 451
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
cuagaccugu uuugcuuuug u                                              21

<210> SEQ ID NO 452
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
acaaaagcaa aacaggucua gaa                                            23

<210> SEQ ID NO 453
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
cuagaccugu uuugcuuuug u                                              21

<210> SEQ ID NO 454
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
acaaaagcaa aacaggucua gaa                                            23
```

```
<210> SEQ ID NO 455
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
cuagaccugu uuugcuuuug u                                              21

<210> SEQ ID NO 456
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 456
acaaaagcaa aacaggucua gaa                                            23

<210> SEQ ID NO 457
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
cuagaccugu uuugcuuuug u                                              21

<210> SEQ ID NO 458
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
acaaaagcaa aacaggucua gaa                                            23

<210> SEQ ID NO 459
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
cuagaccugu uuugcuuuug u                                              21

<210> SEQ ID NO 460
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 460
acaaaagcaa aacaggucua gaa                                              23

<210> SEQ ID NO 461
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
cuagaccugu uuugcuuuug u                                                21

<210> SEQ ID NO 462
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
acaaaagcaa aacaggucua gaa                                              23

<210> SEQ ID NO 463
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
cuagaccugu uuugcuuuug u                                                21

<210> SEQ ID NO 464
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
acaaaagcaa aacaggucua gaa                                              23

<210> SEQ ID NO 465
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
cuagaccugu uuugcuuuug u                                                21

<210> SEQ ID NO 466
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 466
acaaaagcaa aacaggucua gaa                                            23

<210> SEQ ID NO 467
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
cuagaccugu uuugcuuuug u                                              21

<210> SEQ ID NO 468
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
acaaaagcaa aacaggucua gaa                                            23

<210> SEQ ID NO 469
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
cuagaccugu uuugcuuuug u                                              21

<210> SEQ ID NO 470
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
acaaaagcaa aacaggucua gaa                                            23

<210> SEQ ID NO 471
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
cuagaccugu uuugcuuuug u                                              21
```

<210> SEQ ID NO 472
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 472
acaaaagcaa aacaggucua gaa                                           23

<210> SEQ ID NO 473
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 473
cuagaccugu uuugcuuuug u                                             21

<210> SEQ ID NO 474
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 474
acaaaagcaa aacaggucua gaa                                           23

<210> SEQ ID NO 475
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 475
cuagaccugu uuugcuuuug u                                             21

<210> SEQ ID NO 476
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 476
acaaaagcaa aacaggucua gaa                                           23

<210> SEQ ID NO 477
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 477
cuagaccugu uuugcuuuug u                                              21

<210> SEQ ID NO 478
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
acaaaagcaa aacaggucua gaa                                            23

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
cuagaccugu uuugcuuuug u                                              21

<210> SEQ ID NO 480
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
acaaaagcaa aacaggucua gaa                                            23

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
cuagaccugu uuugcuuuug u                                              21

<210> SEQ ID NO 482
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
acaaaagcaa aacaggucua gaa                                            23

<210> SEQ ID NO 483
<211> LENGTH: 21
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
cuagaccugu uuugcuuuug u                                             21

<210> SEQ ID NO 484
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
acaaaagcaa aacaggucua gaa                                           23

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
cuagaccugu uuugcuuuug u                                             21

<210> SEQ ID NO 486
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
acaaaagcaa aacaggucua gaa                                           23

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
cuagaccugu uuugcuuuug u                                             21

<210> SEQ ID NO 488
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
acaaaagcaa aacaggucua gaa                                           23
```

<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
cuagaccugu uuugcuuuug u                                              21

<210> SEQ ID NO 490
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
acaaaagcaa aacaggucua gaa                                            23

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
cuagaccugu uuugcuuuug u                                              21

<210> SEQ ID NO 492
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
acaaaagcaa aacaggucua gaa                                            23

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
cuagaccugu uuugcuuuug u                                              21

<210> SEQ ID NO 494
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

```
                            Synthetic oligonucleotide"

<400> SEQUENCE: 494
acaaaagcaa aacaggucua gaa                                          23

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
cuagaccugu uuugcuuuug u                                            21

<210> SEQ ID NO 496
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
acaaaagcaa aacaggucua gaa                                          23

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
cuagaccugu uuugcuuuug u                                            21

<210> SEQ ID NO 498
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
acaaaagcaa aacaggucua gaa                                          23

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
cuagaccugu uuugcuuuug u                                            21

<210> SEQ ID NO 500
<211> LENGTH: 23
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
acaaaagcaa aacaggucua gaa                                              23

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
cuagaccugu uuugcuuuug u                                                21

<210> SEQ ID NO 502
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
acaaaagcaa aacaggucua gaa                                              23

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
cuagaccugu uuugcuuuug u                                                21

<210> SEQ ID NO 504
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
acaaaagcaa aacaggucua gaa                                              23

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
```
cuagaccugu uuugcuuuug u                                                21

<210> SEQ ID NO 506
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
acaaaagcaa aacaggucua gaa                                              23

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
cuagaccugu uuugcuuuug u                                                21

<210> SEQ ID NO 508
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
acaaaagcaa aacaggucua gaa                                              23

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
cuagaccugu uuugcuuuug u                                                21

<210> SEQ ID NO 510
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
acaaaagcaa aacaggucua gaa                                              23

<210> SEQ ID NO 511
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 511
cuagaccugu uuugcuuuug u                                              21

<210> SEQ ID NO 512
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
acaaaagcaa aacaggucua gaa                                            23

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
cuagaccugu uuugcuuuug u                                              21

<210> SEQ ID NO 514
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
acaaaagcaa aacaggucua gaa                                            23

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
cuagaccugu uuugcuuuug u                                              21

<210> SEQ ID NO 516
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
acaaaagcaa aacaggucua gaa                                            23

<210> SEQ ID NO 517
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
cuagaccugu uuugcuuuug u                                              21

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
acaaaagcaa aacaggucua gaa                                            23

<210> SEQ ID NO 519
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
cuagaccugu uuugcuuuug u                                              21

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
acaaaagcaa aacaggucua gaa                                            23

<210> SEQ ID NO 521
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
cuagaccugu uuugcuuuug u                                              21

<210> SEQ ID NO 522
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
```
acaaaagcaa aacaggucua gaa          23

<210> SEQ ID NO 523
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
cuagaccugu uuugcuuuug u          21

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
acaaaagcaa aacaggucua gaa          23

<210> SEQ ID NO 525
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
cuagaccugu uuugcuuuug u          21

<210> SEQ ID NO 526
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
acaaaagcaa aacaggucua gaa          23

<210> SEQ ID NO 527
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
cuagaccugu uuugcuuuug u          21

<210> SEQ ID NO 528
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 528
acaaaagcaa aacaggucua gaa                                          23

<210> SEQ ID NO 529
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
cuagaccugu uuugcuuuug u                                            21

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
acaaaagcaa aacaggucua gaa                                          23

<210> SEQ ID NO 531
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
cuagaccugu uuugcuuuug u                                            21

<210> SEQ ID NO 532
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
acaaaagcaa aacaggucua gaa                                          23

<210> SEQ ID NO 533
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
cuagaccugu uuugcuuuug u                                            21
```

```
<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 534
acaaaagcaa aacaggucua gaa                                              23

<210> SEQ ID NO 535
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 535
cuagaccugu uuugcuuuug u                                                21

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
acaaaagcaa aacaggucua gaa                                              23

<210> SEQ ID NO 537
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
cuagaccugu uuugcuuuug u                                                21

<210> SEQ ID NO 538
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
acaaaagcaa aacaggucua gaa                                              23

<210> SEQ ID NO 539
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 539
cuagaccugu uuugcuuuug u                                              21

<210> SEQ ID NO 540
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
acaaaagcaa aacaggucua gaa                                            23

<210> SEQ ID NO 541
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
cuagaccugu uuugcuuuug u                                              21

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
acaaaagcaa aacaggucua gaa                                            23

<210> SEQ ID NO 543
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
cuagaccugu uuugcuuuug u                                              21

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
acaaaagcaa aacaggucua gaa                                            23

<210> SEQ ID NO 545
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 545
cuagaccugu uuugcuuuug u                                             21

<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
acaaaagcaa aacaggucua gaa                                           23

<210> SEQ ID NO 547
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
cuagaccugu uuugcuuuug u                                             21

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
acaaaagcaa aacaggucua gaa                                           23

<210> SEQ ID NO 549
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
cuagaccugu uuugcuuuug u                                             21

<210> SEQ ID NO 550
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
acaaaagcaa aacaggucua gaa                                           23
```

<210> SEQ ID NO 551
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 551
cuagaccugu uuugcuuuug u                                             21

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 552
acaaaagcaa aacaggucua gaa                                           23

<210> SEQ ID NO 553
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 553
agaccuguuu ugcuuuugu                                                19

<210> SEQ ID NO 554
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 554
acaaaagcaa aacaggucua g                                             21

<210> SEQ ID NO 555
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 555
cuagaccugu uuugcuuuug u                                             21

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

-continued

<400> SEQUENCE: 556
acaaaagcaa aacaggucua g                                          21

<210> SEQ ID NO 557
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
agaccuguuu ugcuuuugu                                             19

<210> SEQ ID NO 558
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
acaaaagcaa aacaggucua g                                          21

<210> SEQ ID NO 559
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
uagaccuguu uugcuuuugu                                            20

<210> SEQ ID NO 560
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
acaaaagcaa aacaggucua g                                          21

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
cuagaccugu uuugcuuuug u                                          21

<210> SEQ ID NO 562
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
acaaaagcaa aacaggucua g                                              21

<210> SEQ ID NO 563
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
uagaccuguu uugcuuuugu a                                              21

<210> SEQ ID NO 564
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
uacaaaagca aaacaggucu aga                                            23

<210> SEQ ID NO 565
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
uagaccuguu uugcuuuugu                                                20

<210> SEQ ID NO 566
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
acaaaagcaa aacaggucua                                                20

<210> SEQ ID NO 567
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
gaccuguuuu gcuuuugu                                                  18
```

```
<210> SEQ ID NO 568
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
acaaaagcaa aacaggucua                                                    20

<210> SEQ ID NO 569
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
agaccuguuu ugcuuuugu                                                     19

<210> SEQ ID NO 570
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
acaaaagcaa aacaggucua                                                    20

<210> SEQ ID NO 571
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
uagaccuguu uugcuuuugu                                                    20

<210> SEQ ID NO 572
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
acaaaagcaa aacaggucua                                                    20

<210> SEQ ID NO 573
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

```
            Synthetic oligonucleotide"

<400> SEQUENCE: 573
agaccuguuu ugcuuuugu                                                19

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
acaaaagcaa aacaggucua g                                             21

<210> SEQ ID NO 575
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
agaccuguuu ugcuuuugu                                                19

<210> SEQ ID NO 576
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
acaaaagcaa aacaggucua g                                             21

<210> SEQ ID NO 577
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
agaccuguuu ugcuuuugu                                                19

<210> SEQ ID NO 578
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
acaaaagcaa aacaggucua g                                             21

<210> SEQ ID NO 579
<211> LENGTH: 19
```

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
agaccuguuu ugcuuuugu                                                   19

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
acaaaagcaa aacaggucua g                                                21

<210> SEQ ID NO 581
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
agaccuguuu ugcuuuugu                                                   19

<210> SEQ ID NO 582
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
acaaaagcaa aacaggucua g                                                21

<210> SEQ ID NO 583
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
agaccuguuu ugcuuuugu                                                   19

<210> SEQ ID NO 584
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
```
acaaaagcaa aacaggucua g                                      21

<210> SEQ ID NO 585
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
agaccuguuu ugcuuuugu                                         19

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
acaaaagcaa aacaggucua g                                      21

<210> SEQ ID NO 587
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
agaccuguuu ugcuuuugu                                         19

<210> SEQ ID NO 588
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
acaaaagcaa aacaggucua g                                      21

<210> SEQ ID NO 589
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
agaccuguuu ugcuuuugu                                         19

<210> SEQ ID NO 590
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
acaaaagcaa aacaggucua g                                          21

<210> SEQ ID NO 591
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
agaccuguuu ugcuuuugu                                             19

<210> SEQ ID NO 592
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
acaaaagcaa aacaggucua g                                          21

<210> SEQ ID NO 593
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
agaccuguuu ugcuuuugu                                             19

<210> SEQ ID NO 594
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
acaaaagcaa aacaggucua g                                          21

<210> SEQ ID NO 595
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
agaccuguuu ugcuuuugu                                             19

<210> SEQ ID NO 596

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
acaaaagcaa aacaggucua g                                        21

<210> SEQ ID NO 597
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
agaccuguuu ugcuuuugu                                           19

<210> SEQ ID NO 598
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
acaaaagcaa aacaggucua g                                        21

<210> SEQ ID NO 599
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
agaccuguuu ugcuuuugu                                           19

<210> SEQ ID NO 600
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
acaaaagcaa aacaggucua g                                        21

<210> SEQ ID NO 601
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
```
agaccuguuu ugcuuuugu         19

<210> SEQ ID NO 602
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
acaaaagcaa aacaggucua g         21

<210> SEQ ID NO 603
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
agaccuguuu ugcuuuugu         19

<210> SEQ ID NO 604
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
acaaaagcaa aacaggucua g         21

<210> SEQ ID NO 605
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
gaccuguuuu gcuuuugu         18

<210> SEQ ID NO 606
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
acaaaagcaa aacaggucau a         21

<210> SEQ ID NO 607
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 607
agaccuguuu ugcuuuugu                                                19

<210> SEQ ID NO 608
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
acaaaagcaa aacaggucu                                                19

<210> SEQ ID NO 609
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
gaccuguuuu gcuuuugu                                                 18

<210> SEQ ID NO 610
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
acaaaagcaa aacaggucu                                                19

<210> SEQ ID NO 611
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
uuuuguaacu ugaagauauu u                                             21

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
aaauaucuuc aaguuacaaa agc                                           23
```

```
<210> SEQ ID NO 613
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
uuuguaacuu gaagauauuu a                                              21

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
uaaauaucuu caaguuacaa aag                                            23

<210> SEQ ID NO 615
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
uuguaacuug aagauauuua u                                              21

<210> SEQ ID NO 616
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
auaaauaucu ucaaguuaca aaa                                            23

<210> SEQ ID NO 617
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
uguaacuuga agauauuuau u                                              21

<210> SEQ ID NO 618
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 618
aauaaauauc uucaaguuac aaa                                          23

<210> SEQ ID NO 619
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
guaacuugaa gauauuuauu u                                            21

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
aaauaaauau cuucaaguua caa                                          23

<210> SEQ ID NO 621
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
cuagaccugu uuugcuuuug u                                            21

<210> SEQ ID NO 622
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
acaaaagcaa aacaggucua gaa                                          23

<210> SEQ ID NO 623
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
cuagaccugu uuugcuuuug a                                            21

<210> SEQ ID NO 624
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 624
ucaaaagcaa aacaggucua gaa                                               23

<210> SEQ ID NO 625
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
guagaccugu uuugcuuuug u                                                 21

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
acaaaagcaa aacaggucua cuu                                               23

<210> SEQ ID NO 627
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
gaagaccugu uuugcuuuug u                                                 21

<210> SEQ ID NO 628
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
acaaaagcaa aacaggucuu cuu                                               23

<210> SEQ ID NO 629
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
gaugaccugu uuugcuuuug u                                                 21
```

```
<210> SEQ ID NO 630
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
acaaaagcaa aacaggucau cuu                                          23

<210> SEQ ID NO 631
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
gaugaccugu uuugcuuuug u                                            21

<210> SEQ ID NO 632
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
acaaaagcaa aacaggucau caa                                          23

<210> SEQ ID NO 633
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
caucaccugu uuugcuuuug u                                            21

<210> SEQ ID NO 634
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
acaaaagcaa aacaggugau gaa                                          23

<210> SEQ ID NO 635
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 635
cuucuccugu uuugcuuuug u                                           21

<210> SEQ ID NO 636
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
acaaaagcaa aacaggagaa gaa                                         23

<210> SEQ ID NO 637
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
cuacugcugu uuugcuuuug u                                           21

<210> SEQ ID NO 638
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
acaaaagcaa aacagcagua gaa                                         23

<210> SEQ ID NO 639
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
cuagaccugu uuugcuuuug u                                           21

<210> SEQ ID NO 640
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
acaaaagcaa aacaggucua gaa                                         23

<210> SEQ ID NO 641
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
cuagaccugu uuugcuuuug u                                            21

<210> SEQ ID NO 642
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
acaaaagcaa aacaggucua gaa                                          23

<210> SEQ ID NO 643
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
cuagaccugu uuugcuuuug u                                            21

<210> SEQ ID NO 644
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
acaaaagcaa aacaggucua gaa                                          23

<210> SEQ ID NO 645
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
cuagaccugu uuugcuuuug u                                            21

<210> SEQ ID NO 646
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
acaaaagcaa aacaggucua gaa                                          23
```

<210> SEQ ID NO 647
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
cuagaccugu uuugcuuuug u                                              21

<210> SEQ ID NO 648
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
acaaaagcaa aacaggucua gaa                                            23

<210> SEQ ID NO 649
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
cuagaccugu uuugcuuuug u                                              21

<210> SEQ ID NO 650
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
acaaaagcaa aacaggucua gaa                                            23

<210> SEQ ID NO 651
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
cuagaccugu uuugcuuuug u                                              21

<210> SEQ ID NO 652
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 652
acaaaagcaa aacaggucua gaa                                              23

<210> SEQ ID NO 653
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
cuagaccugu uuugcuuuug u                                                21

<210> SEQ ID NO 654
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
acaaaagcaa aacaggucua gaa                                              23

<210> SEQ ID NO 655
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
cuagaccugu uuugcuuuug u                                                21

<210> SEQ ID NO 656
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
acaaaagcaa aacaggucua gaa                                              23

<210> SEQ ID NO 657
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
cuagaccugu uuugcuuuug u                                                21

<210> SEQ ID NO 658
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
acaaaagcaa aacaggucua gaa                                           23

<210> SEQ ID NO 659
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
cuagaccugu uuugcuuuug u                                             21

<210> SEQ ID NO 660
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
acaaaagcaa aacaggucua gaa                                           23

<210> SEQ ID NO 661
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
cuagaccugu uuugcuuuug u                                             21

<210> SEQ ID NO 662
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
acaaaagcaa aacaggucua gaa                                           23

<210> SEQ ID NO 663
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
```
cuagaccugu uuugcuuuug u                                            21

<210> SEQ ID NO 664
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
acaaaagcaa aacaggucua gaa                                          23

<210> SEQ ID NO 665
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665
cuagaccugu uuugcuuuug u                                            21

<210> SEQ ID NO 666
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
acaaaagcaa aacaggucua gaa                                          23

<210> SEQ ID NO 667
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
cuagaccugu uuugcuuuug u                                            21

<210> SEQ ID NO 668
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
acaaaagcaa aacaggucua gaa                                          23

<210> SEQ ID NO 669
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 669
cuagaccugu uuugcuuuug u                                                  21

<210> SEQ ID NO 670
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
acaaaagcaa aacaggucua gaa                                                23

<210> SEQ ID NO 671
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
cuagaccugu uuugcuuuug u                                                  21

<210> SEQ ID NO 672
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
acaaaagcaa aacaggucua gaa                                                23

<210> SEQ ID NO 673
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
cuagaccugu uuugcuuuug u                                                  21

<210> SEQ ID NO 674
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
acaaaagcaa aacaggucua gaa                                                23

<210> SEQ ID NO 675
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
cuagaccugu uuugcuuuug u                                              21

<210> SEQ ID NO 676
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
acaaaagcaa aacaggucua gaa                                            23

<210> SEQ ID NO 677
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
caagcagaca uuuaucuuuu u                                              21

<210> SEQ ID NO 678
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
aaaaagauaa augucugcuu gcu                                            23

<210> SEQ ID NO 679
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
cuagaccugu uuugcuuuug u                                              21

<210> SEQ ID NO 680
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
```

-continued acaaaagcaa aacaggucua gaa                                              23

<210> SEQ ID NO 681
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
cuagaccugu uuugcuuuug u                                                21

<210> SEQ ID NO 682
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
acaaaagcaa aacaggucua gaa                                              23

<210> SEQ ID NO 683
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 683
cuagaccugu tuugcuuuug u                                                21

<210> SEQ ID NO 684
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
acaaaagcaa aacaggucua gaa                                              23

<210> SEQ ID NO 685
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
acaaaagcaa aacaggucua gaa                                              23

<210> SEQ ID NO 686

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 686
cuagaccugu uugcuuuug u                                              21

<210> SEQ ID NO 687
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 687
cuagaccugu tuugcuuuug u                                             21

<210> SEQ ID NO 688
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
acaaaagcaa aacaggucua gaa                                           23
```